US008916575B2

(12) United States Patent
McGowan et al.

(10) Patent No.: US 8,916,575 B2
(45) Date of Patent: Dec. 23, 2014

(54) QUINAZOLINE DERIVATIVES FOR THE TREATMENT OF VIRAL INFECTIONS AND FURTHER DISEASES

(75) Inventors: David McGowan, Brussels (BE); Pierre Jean-Marie Bernard Raboisson, Rosieres (BE); Tim Hugo Maria Jonckers, Heist-op-den-Berg (BE); Stefaan Julien Last, Lint (BE); Werner Embrechts, Beerse (BE); Serge Maria Aloysius Pieters, Hulst (NL)

(73) Assignee: Janssen R&D Ireland, Little Island, Co Cork (IE)

( * ) Notice: Subject to any disclaimer, the term of this patent is extended or adjusted under 35 U.S.C. 154(b) by 0 days.

(21) Appl. No.: 14/118,527

(22) PCT Filed: May 18, 2012

(86) PCT No.: PCT/EP2012/059234
§ 371 (c)(1),
(2), (4) Date: Nov. 18, 2013

(87) PCT Pub. No.: WO2012/156498
PCT Pub. Date: Nov. 22, 2012

(65) Prior Publication Data
US 2014/0073642 A1   Mar. 13, 2014

(30) Foreign Application Priority Data

May 18, 2011 (EP) .................................... 11166538

(51) Int. Cl.
*A01N 43/54* (2006.01)
*C07D 239/72* (2006.01)
*C07D 401/00* (2006.01)

(52) U.S. Cl.
USPC .................. 514/266.2; 514/266.1; 544/283; 544/284

(58) Field of Classification Search
USPC .................. 544/283, 284; 514/266.1, 266.2
See application file for complete search history.

(56) References Cited

U.S. PATENT DOCUMENTS 7,498,409 B2   3/2009   Vlach et al.

FOREIGN PATENT DOCUMENTS

| JP | 2000 053653 A | 2/2000 |
|---|---|---|
| JP | 2000 053654 A | 2/2000 |
| WO | WO 98 01448 A1 | 9/1998 |
| WO | WO 98 50370 A1 | 11/1998 |
| WO | WO 99/28321 A1 | 10/1999 |
| WO | WO 2005 007672 A2 | 1/2005 |
| WO | WO 2006 050843 A1 | 5/2006 |
| WO | WO 2006 117670 A1 | 11/2006 |
| WO | WO 2008 009078 A2 | 1/2008 |
| WO | WO 2009 067081 A1 | 5/2009 |

OTHER PUBLICATIONS

Vippagunta et at (2001).*
Wolff et al. (1978).*
Banker et al (1976).*
Takeda et al "Toll-Like Receptors" Annu Rev Immunol 2003 vol. 21 pp. 355-376.
De Clercq Erik "(S)-9-(2,3-Dihydroxypropyl)Adenine: An Aliphatic Nucleoside Analog With Broad-Spectrum Antiviral Activity" Science 1978 vol. 200 pp. 563-565.
Fried et al "Peginterferon Alpha-2$_A$ Plus Ribavirin for Chronic Hepatitis C Virus Infection" N Engl J Med 2002 vol. 347(13) pp. 975-982.
Grimm et al "Toll-Like Receptor (TLR) 7 and TLR8 Expression on CD133+Cells in Colorectal Cancer Points to a Specific Role for Inflammation-Induced TLRS in Tumourigenesis and Tumour Progression" European Journal of Cancer 2010 vol. 46 pp. 2849-2857.
Hoffmann Jules A. "The Immune Response of *Drosophila*" Nature 2003 vol. 226 pp. 33-38.
Krieger et al "Enhancement of Hepatitis C Virus RNA Replication by Cell Culture-Adaptive Mutations" Journal of Virology 2001 vol. 75(10) pp. 4614-4624.
Lohmann et al "Replication of Subgenomic Hepatitis C. Virus RNAs in a Hepatoma Cell Line" Science 1999 vol. 285 pp. 110-113.
Lohmann et al "Viral and Cellular Determinants of Hepatitis C Virus RNA Replication in Cell Culture" Journal of Virology 2003 vol. 77(5) pp. 3007-3019.
Ulevitch et al "Therapeutics Targeting the Innate Immune System" Nature 2004 vol. 4 pp. 512-520.
Vedantham et al "Mechanism of Interferon Action in Hairy Cell Leukemia: A Model of Effective Cancer Biotherapy" Cancer Research 1992 vol. 52 pp. 1056-1066.
Bruns et al "Solubilities of Adenosine Antagonists Determined by Radioreceptor Assay" J of Pharmacy and Pharmacology Royal Pharmaceutical Society of Great Britain 1989 vol. 41(9) pp. 590-594.
O'Hara et al Regioselective Synthesis of Imidazo[4,5-G]Quinazoline Quinone Nucleosides and Quinazoline Amino Nucleosides. Studies of Their Xanthine Oxidase and Purine Nucleoside Phosphorylase Substrate Activity JOC 1991 vol. 56 pp. 776-785.

* cited by examiner

*Primary Examiner* — Paul V. Ward

(57) ABSTRACT

This invention relates to quinazoline derivatives, processes for their preparation, pharmaceutical compositions, and their use in therapy of disorders in which the modulation of toll-like-receptors is involved.

5 Claims, No Drawings

QUINAZOLINE DERIVATIVES FOR THE TREATMENT OF VIRAL INFECTIONS AND FURTHER DISEASES

CROSS-REFERENCE TO RELATED APPLICATIONS

This application is a national phase of International Application No. PCT/EP2012/059234 filed on May 18, 2012, which application claims priority from European Patent Application No. 11166538.6 filed on May 18, 2011, the entire disclosures of which are hereby incorporated by reference in their entirety.

This invention relates to quinazoline derivatives, processes for their preparation, pharmaceutical compositions, and their use in therapy.

The present invention relates to the use of quinazoline derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behavior.

It has been estimated that most mammalian species have between ten and fifteen types of Toll-like receptors. Thirteen TLRs (named simply TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For detailed reviews on toll-like receptors see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as purine derivatives in WO 2006 117670, adenine derivatives in WO 98/01448 and WO 99/28321, and pyrimidines in WO 2009/067081.

However, there exists a strong need for novel Toll-Like receptor modulators having preferred selectivity, higher potency, higher metabolic stability, and an improved safety profile compared to the compounds of the prior art.

In the treatment of certain viral infections, regular injections of interferon (IFNα) can be administered, as is the case for hepatitis C virus (HCV), (Fried et. al. Peginterferon-alfa plus ribavirin for chronic hepatitis C virus infection, *N Engl J Med* 2002; 347: 975-82). Orally available small molecule IFN inducers offer the potential advantages of reduced immunogenicity and convenience of administration. Thus, novel IFN inducers are potentially effective new class of drugs for treating virus infections. For an example in the literature of a small molecule IFN inducer having antiviral effect see De Clercq, E.; Descamps, J.; De Somer, P. *Science* 1978, 200, 563-565.

IFNα is also given in combination with other drugs in the treatment of certain types of cancer (refer to Eur. J. Cancer 46, 2849-57, and Cancer Res. 1992, 52, 1056 for examples). TLR 7/8 agonists are also of interest as vaccine adjuvants because of their ability to induce pronounced Th1 response.

In accordance with the present invention a compound of formula (I) is provided

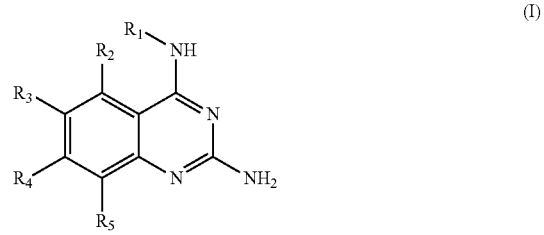

or a pharmaceutically acceptable salt, solvate or polymorph thereof, wherein $R_1$ is $C_{3-8}$alkyl, $C_{3-8}$alkoxy, $C_{2-6}$alkenyl or $C_{2-6}$alkynyl, each of which is optionally substituted by one or more substituents independently selected from halogen, hydroxyl, amino, nitrile, ester, amide, $C_{1-3}$alkyl, $C_{1-3}$alkoxy or $C_{3-6}$cycloalkyl, $R_2$ is hydrogen, halogen, hydroxyl, amine, $C_{1-7}$alkyl, $C_{1-7}$alkylamino, $C_{1-6}$alkoxy, $(C_{1-4})$alkoxy-$(C_{1-4})$alkyl, $C_{3-6}$cycloalkyl, $C_{4-7}$heterocycle, aromatic, bicyclic heterocycle, arylalkyl, heteroaryl, heteroarylalkyl, carboxylic amide, carboxylic ester each of which is optionally substituted by one or more substituents independently selected from halogen, hydroxyl, amino, $C_{1-6}$alkyl, di-$(C_{1-6})$alkylamino, $C_{1-6}$alkylamino, $C_{1-6}$alkyl, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl, or nitrile, $R_3$ is hydrogen, halogen, hydroxyl, amine, $C_{1-7}$alkyl, $C_{1-7}$alkenyl, $C_{1-7}$alkynyl, $C_{1-7}$alkylamino, $C_{1-6}$alkoxy, $(C_{1-4})$alkoxy-$(C_{1-4})$alkyl, $C_{3-6}$cycloalkyl, $C_{4-7}$heterocycle, aromatic, bicyclic heterocycle, arylalkyl, heteroaryl, heteroarylalkyl, aryloxy, heteroaryloxy, ketone, nitrile each of which is optionally substituted by one or more substituents independently selected from halogen, hydroxyl, amino, $C_{1-6}$alkyl, di-$(C_{1-6})$alkylamino, $C_{1-6}$alkylamino, $C_{1-6}$alkyl, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl, or nitrile.

$R_4$ is hydrogen, halogen, hydroxyl, amine, $C_{1-7}$alkyl, $C_{1-7}$alkylamino, $C_{1-6}$alkoxy, $(C_{1-4})$alkoxy-$(C_{1-4})$alkyl, $C_{3-6}$cycloalkyl, $C_{4-7}$heterocycle, bicyclic heterocycle, arylalkyl, heteroarylalkyl, aryloxy, heteroaryloxy each of which is optionally substituted by one or more substituents independently selected from halogen, hydroxyl, amino, $C_{1-6}$alkyl, di-$(C_{1-6})$alkylamino, $C_{1-6}$alkylamino, $C_{1-6}$alkyl, $C_{1-6}$alkoxy, $C_{3-6}$cycloalkyl, carboxylic acid, carboxylic ester, carboxylic amide, heterocycle, aryl, alkenyl, alkynyl, arylalkyl, heteroaryl, heteroarylalkyl, or nitrile, and $R_5$ is hydrogen, fluorine, chlorine or methyl with the proviso that $R_2$, $R_3$, $R_4$, and $R_5$ cannot all be H.

In a first embodiment the present invention provides compounds of formula (I) wherein $R_1$ is butyl, pentyl or 2-pentyl and wherein $R_2$, $R_3$, $R_4$ and $R_5$ are as specified above.

In a further embodiment the current invention relates to compounds of formula (I) wherein $R_1$ is $C_{4-8}$ alkyl substituted with a hydroxyl, and wherein $R_2$, $R_3$, $R_4$ and $R_5$ are as specified above.

Another embodiment relates to compounds of formula (I) wherein $R_1$, when being $C_{4-8}$ alkyl substituted with hydroxyl, is one of the following:

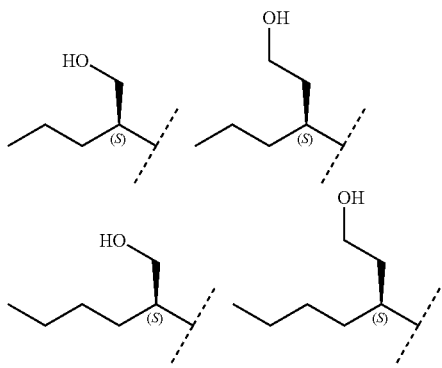

In another embodiment the present invention provides compounds of formula (I) wherein $R_5$ is preferably hydrogen or fluorine and $R_1$, $R_2$, $R_3$, and $R_4$ are as described above.

The compounds of formula (I) and their pharmaceutically acceptable salt, solvate or polymorph thereof have activity as pharmaceuticals, in particular as modulators of Toll-Like Receptor (especially TLR7 and/or TLR8) activity.

So, in a further aspect the present invention provides a pharmaceutical composition comprising a compound of formula (I) or a pharmaceutically acceptable salt, solvate or polymorph thereof together with one or more pharmaceutically acceptable excipients, diluents or carriers.

Furthermore a compound of formula (I) or a pharmaceutically acceptable salt, solvate or polymorph thereof according to the current invention, or a pharmaceutical composition comprising said compound of formula (I) or a pharmaceutically acceptable salt, solvate or polymorph thereof can be used as a medicament.

Another aspect of the invention is that a compound of formula (I) or a pharmaceutically acceptable salt, solvate or polymorph thereof, or said pharmaceutical composition comprising said compound of formula (I) or a pharmaceutically acceptable salt, solvate or polymorph thereof can be used accordingly in the treatment of a disorder in which the modulation of TLR7 and/or TLR8 is involved.

The term "alkyl" refers to a straight-chain or branched-chain saturated aliphatic hydrocarbon containing the specified number of carbon atoms.

The term "halogen" refers to fluorine, chlorine, bromine or iodine.

The term "alkenyl" refers to an alkyl as defined above consisting of at least two carbon atoms and at least one carbon-carbon double bond.

The term "alkynyl" refers to an alkyl as defined above consisting of at least two carbon atoms and at least one carbon-carbon triple bond.

The term "cycloalkyl" refers to a carbocyclic ring containing the specified number of carbon atoms.

The term "alkoxy" refers to an alkyl (carbon and hydrogen chain) group singular bonded to oxygen like for instance a methoxy group or ethoxy group.

The term "aryl" means an aromatic ring structure optionally comprising one or two heteroatoms selected from N, O and S, in particular from N and O. Said aromatic ring structure may have 5, 6 or 7 ring atoms. In particular, said aromatic ring structure may have 5 or 6 ring atoms.

The term "aryloxy" refers to an aromatic ring structure. Said aromatic group is singularly bonded to oxygen, like for instance phenol.

The term "heteroaryloxy" refers to an aromatic ring structure optionally comprising one or two heteroatoms selected from N, O and S. Said aromatic group, containing 5 to 7 ring atoms, one of which is singularly bonded to oxygen like for instance hydroxypyridine.

The term "bicyclic heterocycle" means an aromatic ring structure, as defined for the term "aryl" comprised of two fused aromatic rings. Each ring is optionally comprised of heteroatoms selected from N, O and S, in particular from N and O.

The term arylalkyl" means an aromatic ring structure as defined for the term "aryl" optionally substituted with an alkyl group.

The term "heteroarylalkyl" means an aromatic ring structure as defined for the term "heteroaryl" optionally substituted by an alkyl group.

Heterocycle refers to molecules that are saturated or partially saturated and include ethyloxide, tetrahydrofuran, dioxane or other cyclic ethers. Heterocycles containing nitrogen include, for example azetidine, morpholine, piperidine, piperazine, pyrrolidine, and the like. Other heterocycles include, for example, thiomorpholine, dioxolinyl, and cyclic sulfones.

Heteroaryl groups are heterocyclic groups which are aromatic in nature. These are monocyclic, bicyclic, or polycyclic containing one or more heteroatoms selected from N, O or S. Heteroaryl groups can be, for example, imidazolyl, isoxazolyl, furyl, oxazolyl, pyrrolyl, pyridonyl, pyridyl, pyridazinyl, pyrazinyl, Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

Preparation of Compounds

Compounds of formula (I) are prepared according to scheme 1. The 2,4-dichloroquinazolines can be reacted in separate steps to afford the 2,4-diaminoquinazolines in acceptable yield. In the first step the 2,4-dichloro-quinazoline is mixed or heated with an amine with or without a transition metal catalyst to afford the 2-chloro-4-aminoquinazoline. After workup of the crude 2-chloro-4-aminoquinazoline, the intermediate is heated in a pressure vessel with an ammonia source (for example, ammonia in methanol) and optionally with CuO.

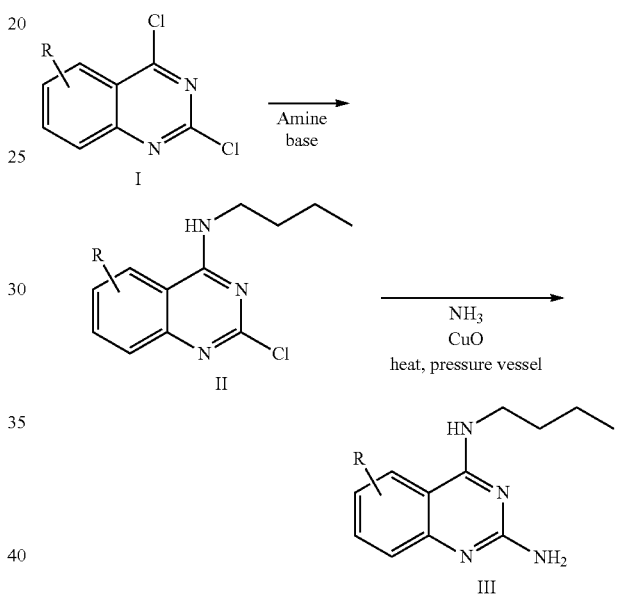

Scheme 1

Compounds of formula (I) can also be prepared according to scheme 2. Substituted anthranilic esters (IV) were heated under acidic conditions in the presence of excess cyanamide, using an alcoholic solvent (e.g. ethanol) or diglyme according to the method described in the literature (O'Hara et. al. JOC (1991) 56, p 776). Subsequent amine substitution of the 2-amino-4-hydroxyquinazolines (V) can proceed via several different pathways. In one example, intermediates V can be heated in the presence of phosphorous oxychloride ($POCl_3$) with or without solvent. After removal of solvents, the amine can be added neat, or in the presence of a polar solvent (e.g. acetonitrile) to afford VI at room temperature or by heating. A second approach is to react intermediates V with a coupling agent such as BOP or PyBOP in the presence of DBU and the amine. The reaction takes place in a polar solvent (e.g. DMF). A third method is to protect the 2-amino group in intermediate V with an acyl group. Intermediate V is reacted with anhydride (e.g. acetic anhydride), typically at reflux for several hours. The solvents can be removed under reduced pressure and the crude can undergo subsequent reaction with $POCl_3$ as described above. Facile removal of the protecting acyl group is done via reaction in a basic solvent (e.g. sodium methoxide in methanol).

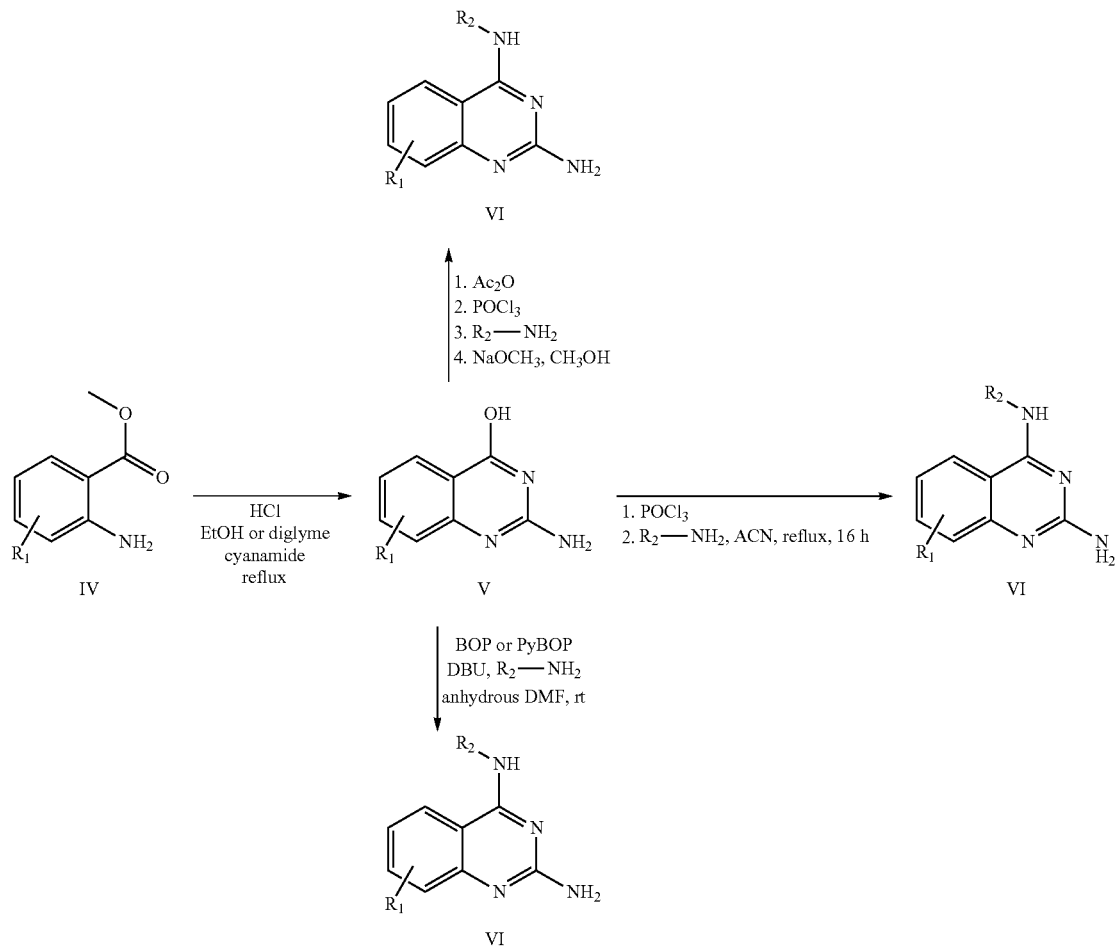

EXPERIMENTAL SECTION

Preparation of Intermediate A

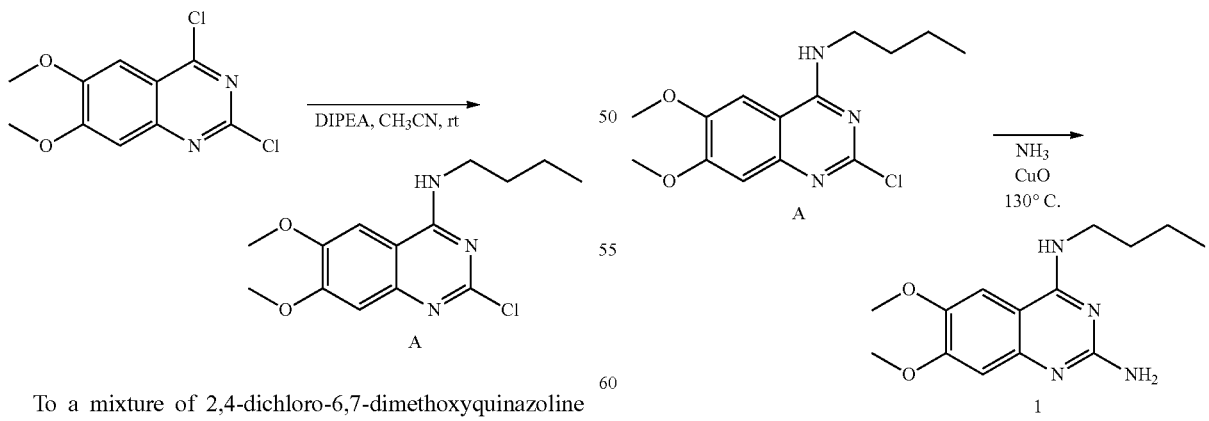

To a mixture of 2,4-dichloro-6,7-dimethoxyquinazoline (500 mg, 1.9 mmol), diisopropylethylamine (0.73 mL, 4.2 mmol), and acetonitrile (0.1 mL) was added a solution of n-butylamine (0.19 mL, 1.9 mmol) in acetonitrile (5 mL) dropwise while stirring. The mixture was allowed to stir for one day at ambient temperature. Ethyl acetate was added, the organic layer was washed with sat. aq ammonium chloride. The organic layer was removed, dried over magnesium sulfate. The solids were removed via filtration to afford crude A, used as such in the next step.

Preparation of Compound 1

Intermediate A (0.5 g, 1.7 mmol) was placed into a 20 mL pressure vessel with 7N ammonia in methanol (15 mL) and to this was added CuO (242 mg, 1.7 mmol). The vessel was sealed and the mixture was heated to 130° C. with stirring for 18 hours. The reaction was allowed to cool to room temperature. The solids were removed via filtration and the solvents of the filtrate were removed under reduced pressure. The crude material was purified via reverse phase column chromatography (Vydac Denali C18 column 10 μm, 250 g, 5 cm). Mobile phase (0.25% NH₄HCO₃ solution in water, CH₃CN).

Preparation of 9

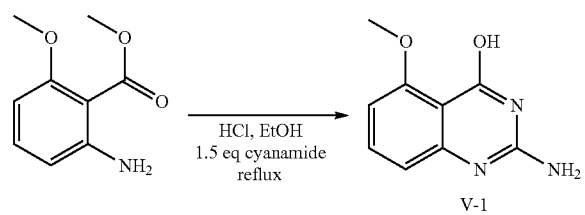

Step 1. Into a 500 mL round bottom flask equipped with a magnetic stir bar was placed methyl 2-amino-6-methoxybenzoate (25 g, 149.6 mmol), ethanol (200 mL), cyanamide (9.43 g, 224 mmol), and concentrated HCl (6 mL). The mixture was allowed to stir at reflux for 6 hours. At one hour intervals, concentrated HCl (0.5 mL) was added. The reaction mixture was allowed to cool to room temperature and the solid, V-1, was isolated via filtration and washed with ethanol.

LC-MS m/z=192 (M+H).

$^1$H NMR (400 MHz, DMSO-d$_6$) δ ppm 3.88 (s, 3H), 6.96 (dd, J=8.2, 3.1 Hz, 2H), 7.69 (t, J=8.3 Hz, 1H), 8.28 (br. s., 2H), 12.67 (br. s., 1H)

Step 2.

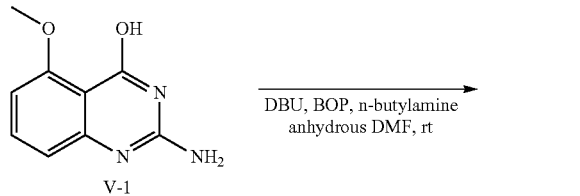

Into a 50 mL vial was placed V-1 (250 mg, 1.24 mmol), anhydrous DMF (5 mL), DBU (0.6 g, 3.73 mmol), and BOP (659 mg, 1.49 mmol). The mixture stirred at room temperature for 2 hours, n-butylamine (287 mg, 3.73 mmol) was added and the reaction was allowed to stir at room temperature for 15 hours. The solvent was reduced in volume and the residue purified via silica column chromatography using a dichloromethane to 10% methanol in dichloromethane gradient. The best fractions were pooled, the solvents were removed under reduced pressure to afford 9.

The following intermediates were prepared according to the method to prepare V-1.

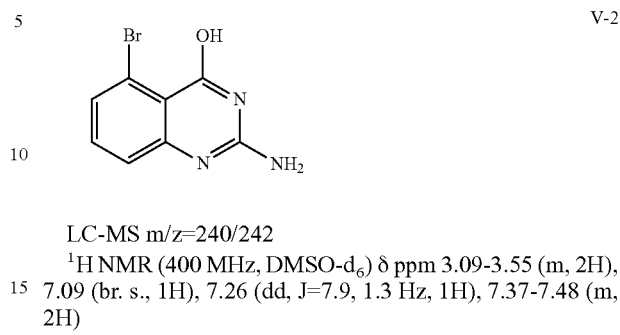

LC-MS m/z=240/242

$^1$H NMR (400 MHz, DMSO-d$_6$) δ ppm 3.09-3.55 (m, 2H), 7.09 (br. s., 1H), 7.26 (dd, J=7.9, 1.3 Hz, 1H), 7.37-7.48 (m, 2H)

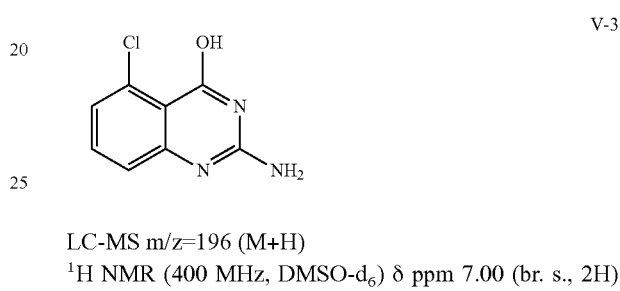

LC-MS m/z=196 (M+H)

$^1$H NMR (400 MHz, DMSO-d$_6$) δ ppm 7.00 (br. s., 2H) 7.13 (d, J=7.78 Hz, 1H) 7.18 (d, J=8.28 Hz, 1H) 7.50 (t, J=8.03 Hz, 1H), phenol proton not observed.

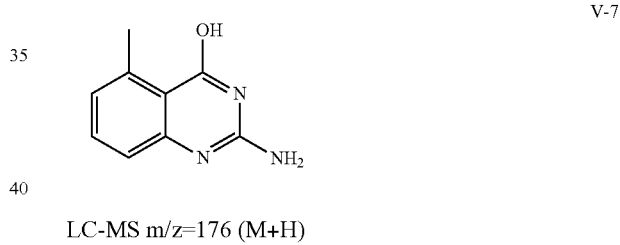

LC-MS m/z=176 (M+H)

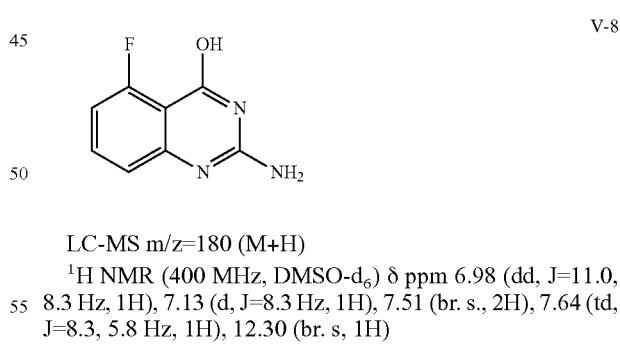

LC-MS m/z=180 (M+H)

$^1$H NMR (400 MHz, DMSO-d$_6$) δ ppm 6.98 (dd, J=11.0, 8.3 Hz, 1H), 7.13 (d, J=8.3 Hz, 1H), 7.51 (br. s., 2H), 7.64 (td, J=8.3, 5.8 Hz, 1H), 12.30 (br. s, 1H)

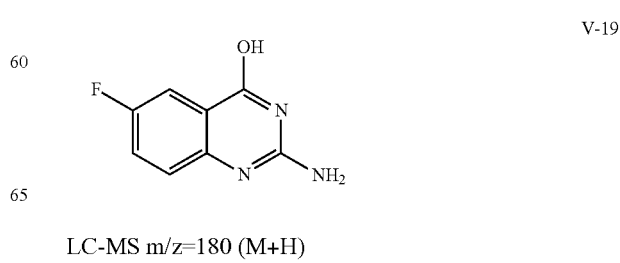

LC-MS m/z=180 (M+H)

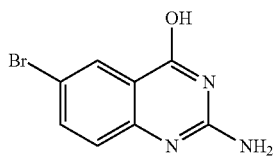
V-14

LC-MS m/z=239/241 (M+H)

$^1$H NMR (400 MHz, DMSO-d$_6$) δ ppm 7.32 (d, J=8.8 Hz, 1H), 7.49 (s, 2H), 7.71 (br. s., 1H), 7.81 (dd, J=8.6, 2.4 Hz, 1H), 8.00 (d, J=2.4 Hz, 1H)

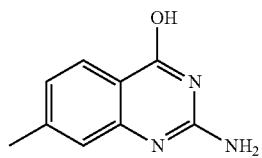
V-5

LC-MS m/z=176 (M+H)

$^1$H NMR (400 MHz, DMSO-d$_6$) δ ppm 2.43 (s, 3H), 7.22 (d, J=1.0 Hz, 1H), 7.24 (s, 1H), 7.89 (d, J=8.0 Hz, 1H), 8.29 (br. s., 2H), 12.65 (br. s, 1H)

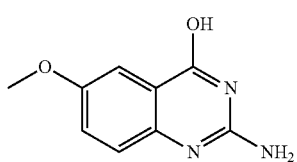
V-20

LC-MS m/z=192 (M+H)

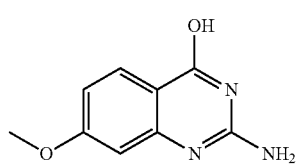
V-24

LC-MS m/z=192 (M+H)

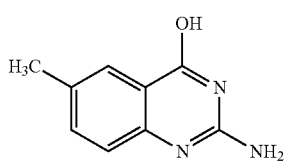
V-21

LC-MS m/z=176 (M+H)

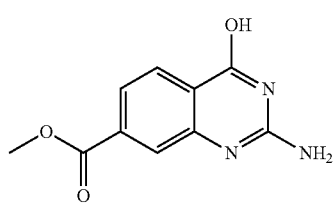
V-25

LC-MS m/z=220 (M+H)

$^1$H NMR (400 MHz, DMSO-d$_6$) δ ppm 3.87-3.95 (m, 3H), 7.12-7.47 (m, 1H), 7.83 (dd, J=8.3, 1.4 Hz, 1H), 7.99 (d, J=1.3 Hz, 1H), 8.07-8.13 (m, 1H), 8.43 (br. s., 2H)

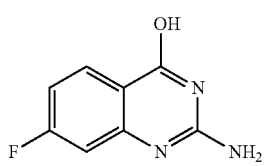
V-4

LC-MS m/z=180 (M+H)

$^1$H NMR (400 MHz, DMSO-d$_6$) δ ppm 7.01-7.16 (m, 2H), 7.56 (br. s., 2H), 7.99 (t, J=7.7 Hz, 1H), 10.38-13.48 (m, 1H)

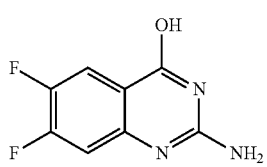
V-22

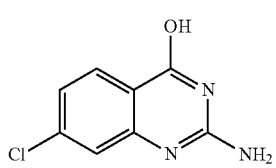
V-23

LC-MS m/z=196 (M+H)

$^1$H NMR (400 MHz, DMSO-d$_6$) δ ppm 7.41 (dd, J=8.5, 2.0 Hz, 1H), 7.55 (d, J=2.0 Hz, 1H), 7.98 (d, J=8.5 Hz, 1H), 8.49 (br. s., 2H), 10.79-13.69 (m, 1H)

V-26

LC-MS m/z=198 (M+H)

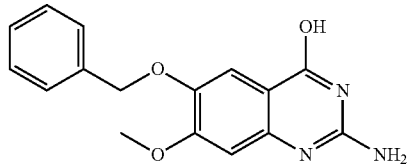
V-27

LC-MS m/z=298 (M+H)

$^1$H NMR (400 MHz, DMSO-d$_6$) δ ppm 3.85 (s, 3H), 5.10 (s, 2H), 6.17 (br. s., 2H), 6.70 (s, 1H), 7.30-7.36 (m, 2H), 7.40 (t, J=7.4 Hz, 2H), 7.44-7.48 (m, 2H), 10.82 (br. s., 1H)

V-28

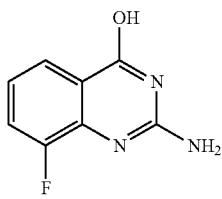

LC-MS m/z=180 (M+H)
$^1$H NMR (400 MHz, DMSO-d$_6$) δ ppm 6.51-6.67 (m, 2H), 7.00-7.08 (m, 1H), 7.42 (ddd, J=11.2, 7.9 1.3 Hz, 1H), 7.69 (dd, J=7.9, 0.6 Hz, 1H), 11.08 (br. s., 1H)

V-29

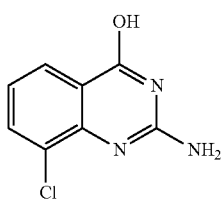

LC-MS m/z=196 (M+H)

V-30

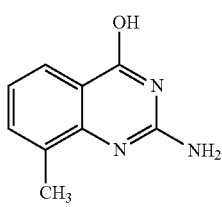

LC-MS m/z=176 (M+H)
$^1$H NMR (400 MHz, DMSO-d$_6$) δ ppm 2.41 (s, 3H), 7.15 (t, J=7.5 Hz, 1H), 7.43 (br. s., 2H), 7.55 (d, J=7.0 Hz, 1H), 7.80 (d, J=7.8 Hz, 1H), 11.17-12.49 (m, 1H)
Preparation of 10

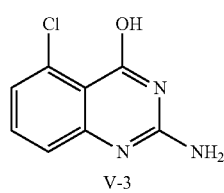

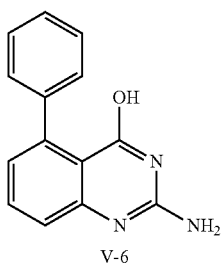

Step 1. Preparation of V-6. Into a 50 mL vial equipped with a magnetic stir bar was placed V-3 (500 mg, 2.16 mmol), phenylboronic acid (342 mg, 2.8 mmol), potassium carbonate (1.19 g, 8.62 mmol), dioxane (5.5 mL), water (1.8 mL), and tetrakis(triphenylphosphine)palladium (249 mg, 0.215 mmol). Nitrogen gas was bubbled through the reaction mixture for 10 minutes. The vial was sealed and heated to 130° C. The reaction cooled to room temperature and the solvents were removed under reduced pressure. The crude was purified via reverse phase column chromatography (RP Vydac Denali C18-10 μm, 200 g, 5 cm. Mobile phase 0.25% NH$_4$HCO$_3$ solution in water, CH$_3$CN) to afford V-6.
LC-MS m/z=238 (M+H)

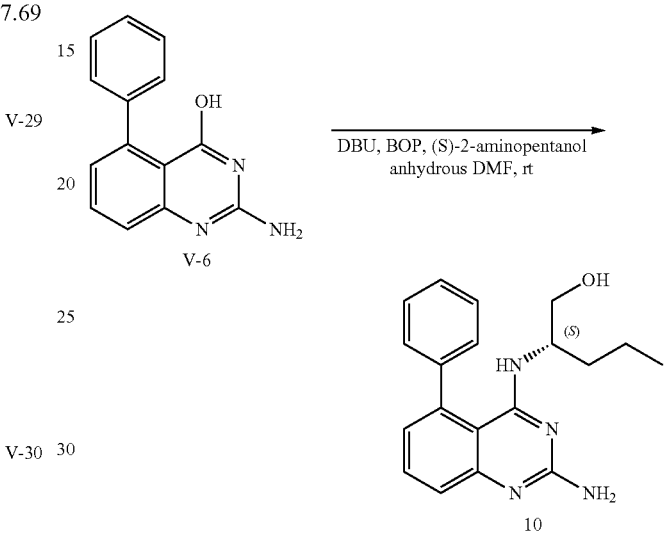

Step 2. Into a 50 mL vial equipped with a magnetic stir bar was placed V-6 (148 mg, 0.624 mmol), anhydrous DMF (3.5 mL), DBU (0.373 mL, 2.5 mmol), BOP (345 mg, 0.78 mmol), then (S)-2-aminopentanol (322 mg, 3.12 mmol). The reaction mixture was allowed to stir at room temperature for 3 days. The volatiles were removed under reduced pressure and the crude was partitioned between water and ethyl acetate. The organic layers were combined, dried (magnesium sulfate), the solids were removed by filtration, and the solvents of to the filtrate were removed under reduced pressure. The crude was purified via reverse phase column chromatography (RP SunFire Prep C18 OBD-10 μm, 30×150 mm). Mobile phase (0.25% NH$_4$HCO$_3$ solution in water, CH$_3$CN) to afford 10.
Preparation of 11

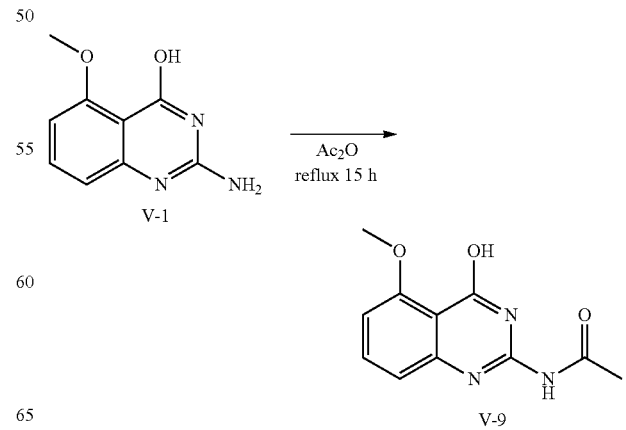

Step 1. Into a 1 L round bottom flask equipped with a magnetic stir bar was placed V-1 (8.8 g, 46.03 mmol) and acetic anhydride (150 mL). The flask was equipped with a reflux condenser and the mixture was heated to reflux with stirring for 15 hours. The precipitate was isolated by filtration and washed with diisopropylether then dried in vacuo to afford a white solid, V-9.

LC-MS m/z=234 (M+H)

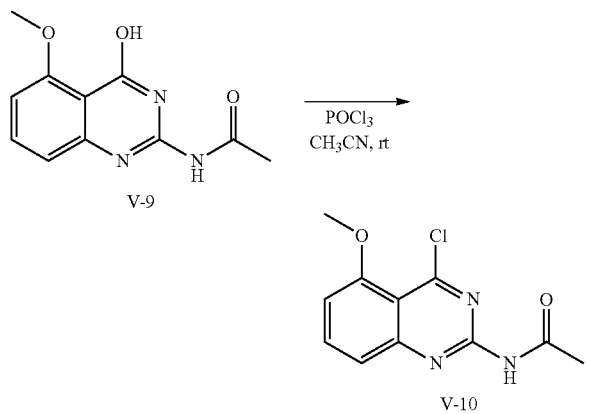

Step 2. Into a 250 mL round bottom flask equipped with a magnetic stir bar was added V-9 (4.5 g, 19.3 mmol), and acetonitrile (100 mL). POCl$_3$ (5.56 mL, 59.8 mmol) was added dropwise over 30 minutes, followed by the addition of DIPEA (10.3 mL, 59.8 mmol). The reaction mixture became a brown solution and stirred for 2 hours at room temperature. The reaction mixture was poured into 1M NaOH (100 mL) and extracted with ethyl acetate (2×100 mL). The combined organic layers were dried over MgSO$_4$, the solids were removed via filtration and the filtrate was used as such in the next step.

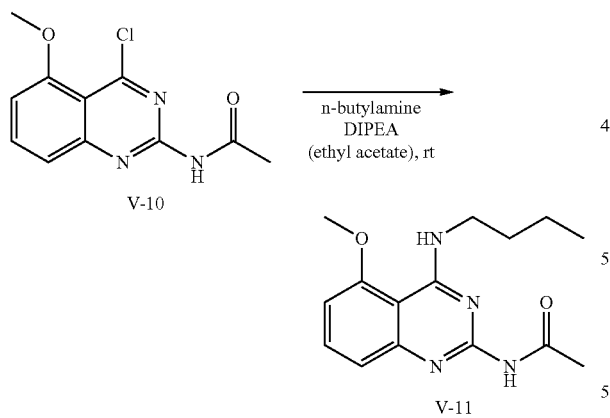

Step 3. The filtrate solution from step 2 in ethyl acetate was treated with DIPEA (9.2 mL, 53.6 mmol) and n-butylamine (3.5 mL, 35.8 mmol). The reaction mixture was stirred for 16 hours at ambient temperature. The solvent was removed under reduced pressure and the crude was reconstituted in dichloromethane and washed with water. The organic layer was dried (MgSO$_4$), the solids were removed by filtration, and the solvents of the filtrate were evaporated to dryness to obtain an orange solid, V-11.

LC-MS m/z=289 (M+H)

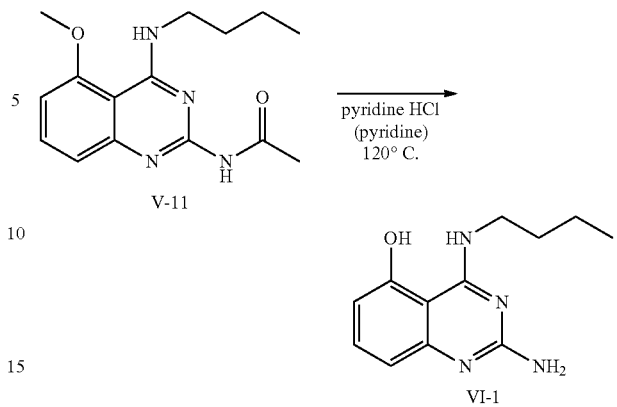

Step 4. Into a 30 mL pressure tube was placed V-11 (2.8 g, 9.71 mmol), pyridine hydrochloride (6.73 g, 58.26 mmol), and pyridine (50 mL) and the mixture was heated to 120° C. for 16 hours. The pyridine was removed under reduced pressure. The crude was dissolved in a mixture of dichloromethane/methanol: 95/5 and washed with a 1N HCl solution and water. The organic layer was dried (MgSO$_4$), the solids were removed via filtration and the solvents of the filtrate were removed under reduced pressure to afford VI-1.

LC-MS m/z=231 (M–H)

$^1$H NMR (400 MHz, DMSO-d$_6$) δ ppm 0.92 (t, J=7.37 Hz, 3H) 1.33-1.43 (m, 2H) 1.50-1.59 (m, 2H) 3.41-3.49 (m, 2H) 5.79-5.88 (m, 1H) 6.02 (d, J=8.14 Hz, 1H) 6.91 (br. s., 2H) 6.99-7.04 (m, 1H) 10.78 (br. s., 1H) 13.35 (br. s., 1H)

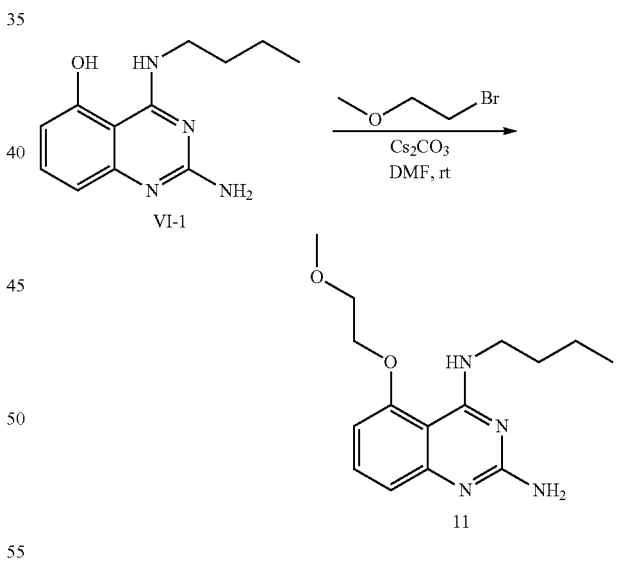

Step 5. Into a 100 mL flask was placed VI-1 (175 mg, 0.753 mmol), cesium carbonate (0.74 g, 2.26 mmol) and DMF (15 mL). The mixture was stirred at ambient temperature for 30 minutes. 2-bromoethyl methyl ether (0.089 mL, 0.94 mmol) was added and the mixture was stirred for 16 hours at room temperature. The solvent was removed under reduced pressure and the crude residue was purified by HPLC (RP Vydac Denali C18-10 µm, 250 g, 5 cm. Mobile phase (0.25% NH$_4$HCO$_3$ solution in water, methanol), the best fractions were collected and the solvents were removed under reduced pressure to obtain 11 as a solid.

Preparation of 12

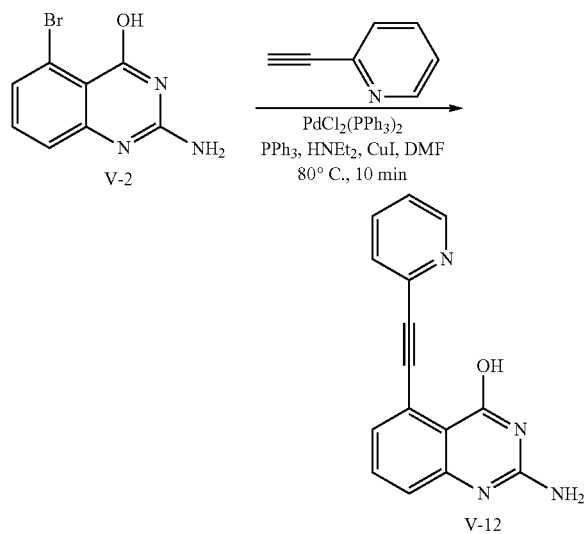

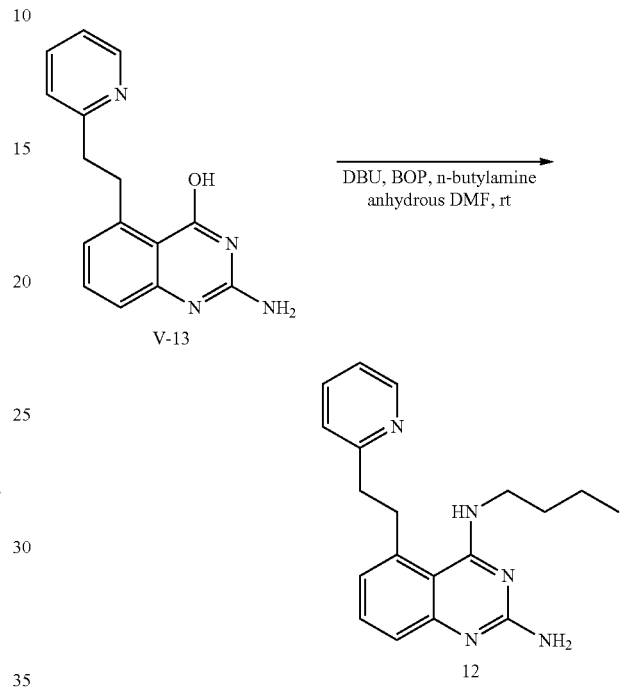

Step 1. V-2 was dissolved in DMF (15 mL) and purged with N$_2$ on an oil bath at 80° C. for 10 minutes. Then bis(triphenylphosphine)palladium(II) dichloride (69 mg, 0.098 mmol), triphenylphosphine (57.6 mg, 0.22 mmol) and copper iodide (42.5 mg, 0.22 mmol) were added. After 5 minutes of purging with N$_2$, diethylamine (3.15 mL, 30.31 mmol) was added followed by the addition of 2-pyridylethyne (168 mg, 1.63 mmol). The vessel was closed and the reaction stirred at 80° C. for 16 hours. The reaction mixture was poured into ice water, and the precipitate was isolated by filtration, washed with water and dried under vacuum. The product was stirred in dichloromethane for 30 minutes. The precipitate was isolated by filtration, washed with dichloromethane and diisopropyl ether and dried under vacuo at 50° C. to obtain V-12.

LC-MS m/z=263 (M−H)

Step 2. To a solution of V-12 (300 mg, 1.15 mmol) in THF (50 mL) was placed 10% Pd/C (100 mg) under an N$_2$ (g) atmosphere. The reaction mixture stirred for 16 hours at room temperature, and subsequently filtered over packed decalite. The solvent of the filtrate was removed under reduced pressure to afford crude V-13, used as such in the next step.

LC-MS m/z=267 (M−H)

Step 3. Example 12 was prepared according to the method to prepare 9.

Preparation of 14

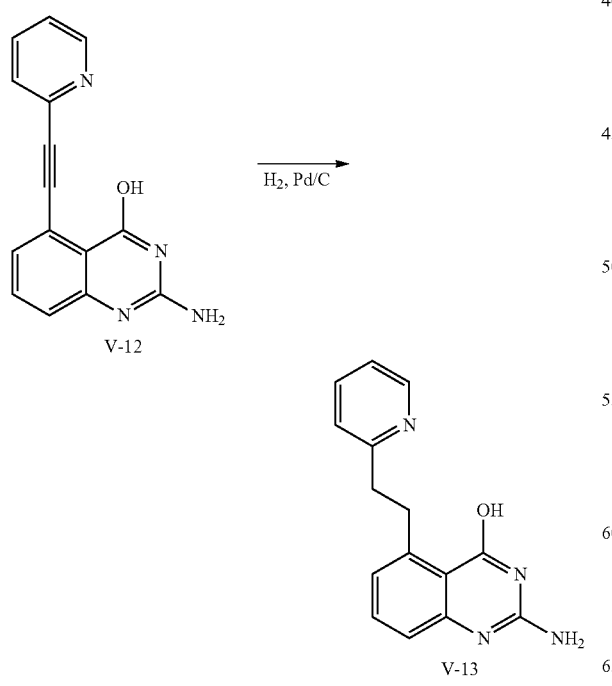

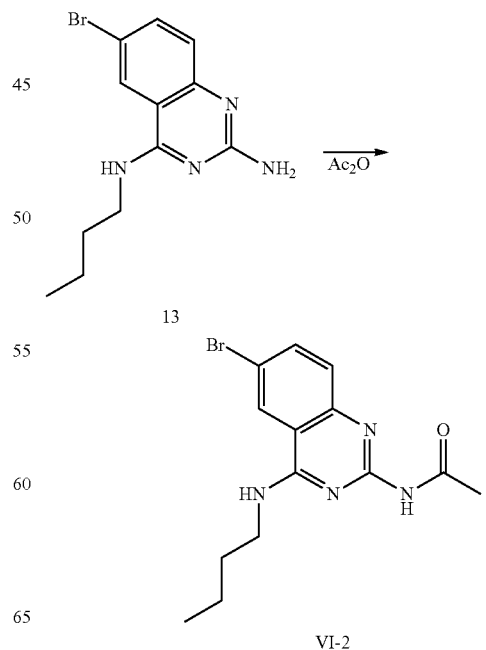

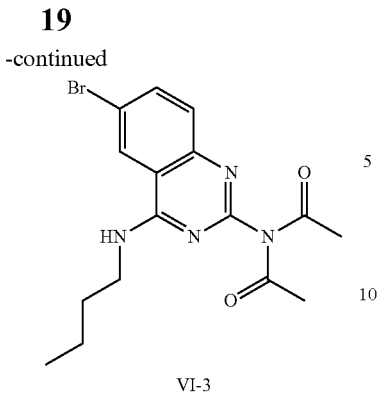

VI-3

Step 1. Intermediates VI-2 and VI-3 was prepared according to the method to prepare VI-1. VI-3 was isolated after stirring with diisopropylether at room temperature.

VI-2: LC-MS m/z=337 (M+H)
VI-3: LC-MS m/z=379 (M+H)

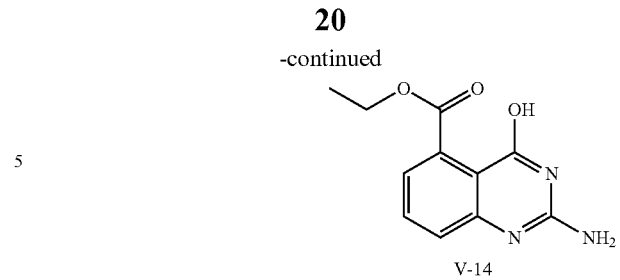

V-14

Step 1. Into a 500 mL round bottom flask equipped with a magnetic stir bar was placed 3-aminophthalic acid hydrochloride (25 g, 115 mmol), ethanol (250 mL), cyanamide (7.25 g, 172 mmol), and concentrated HCl (6 mL). The flask was equipped with a reflux condenser and the mixture was allowed to stir at reflux for 6 hours. At one hour intervals, concentrated HCl (0.5 mL) was added via glass pipette. The reaction was allowed to cool to room temperature, the solvents were removed under reduced pressure to afford a yellow oil. The crude was dried over silica gel then partially purified via silica gel column chromatography using a dichloromethane to 10% methanol in dichloromethane gradient. The crude, yellow solid, V-14, was used as such in the next step.

LC-MS m/z=234 (M+H).

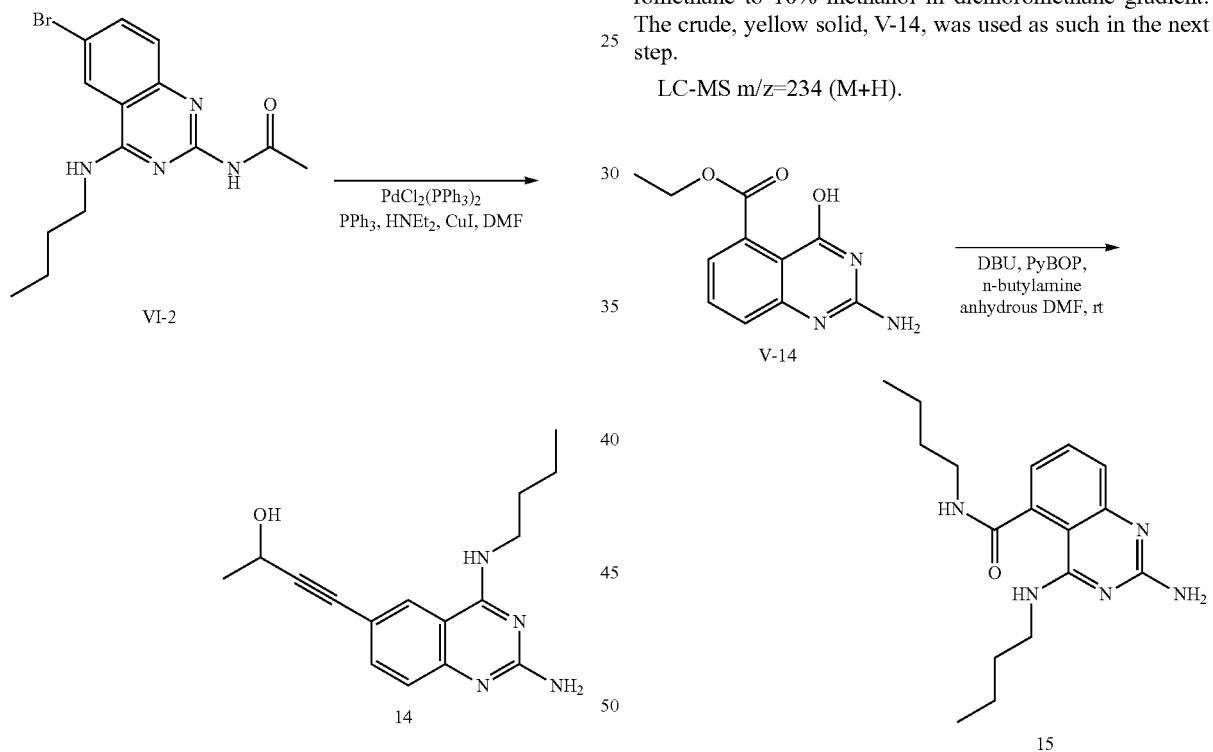

Step 2. Compound 14 was prepared according to the method to prepare intermediate V-12.

Preparation of 15

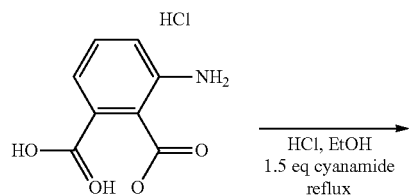

Step 2. Into a 100 mL round bottom flask equipped with a magnetic stir bar was placed V-14 (1.7 g, 7.29 mmol), anhydrous DMF (25 mL), DBU (3.3 g, 21.87 mmol), and PyBOP (4.55 g, 8.75 mmol). The reaction mixture was allowed to stir for 1 hour at room temperature. Then n-butylamine (2.1 g, 29.2 mmol) was added and the mixture was allowed to stir for 15 hours at room temperature. The solvent was removed under reduced pressure and the crude was filtered through silica gel using 20% methanol in dichloromethane. The solvents of the filtrate were removed under reduced pressure and the crude oil (15, 4 g) was purified via reverse phase column chromatography (RP Vydac Denali C18-10 μm, 200 g, 5 cm). Mobile phase (0.25% NH$_4$HCO$_3$ solution in water, CH$_3$CN).

Preparation of 16

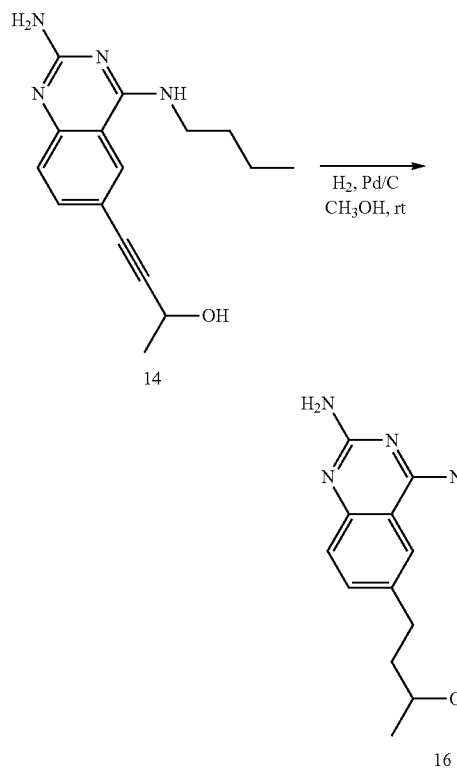

To a suspension of 10% Pd/C in methanol (25 mL) under a N₂ atmosphere was added compound 14 (111 mg, 0.39 mmol). The nitrogen atmosphere was removed and replaced by hydrogen gas. The mixture was allowed to stir at room temperature until 2 equivalents of hydrogen gas were consumed. The reaction mixture was filtered over packed decalite. The solvent of the filtrate was removed under reduced pressure. The crude was purified via silica gel column chromatography using a dichloromethane to 10% methanol in dichloromethane gradient to afford 16.

Preparation of 18

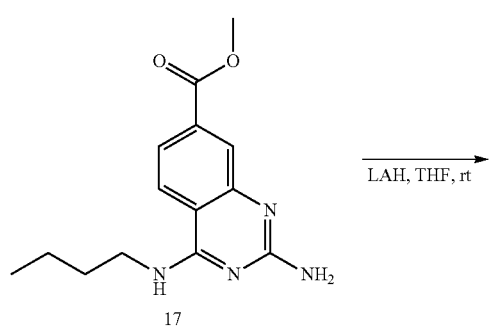

17 (625 mg, 2.28 mmol) was dissolved in anhydrous THF (10 mL). LAH (1M in THF, 3.42 mL, 3.42 mmol) was added dropwise and the reaction mixture was stirred for 3 hours at room temperature. LC-MS showed complete conversion to the desired product. The reaction mixture was quenched with sat., aq. NH₄Cl, the solids were removed by filtration and the solvents of the filtrate were removed under reduced pressure. The residue was purified via prep. HPLC yielding the product as a white solid.

Preparation of 19

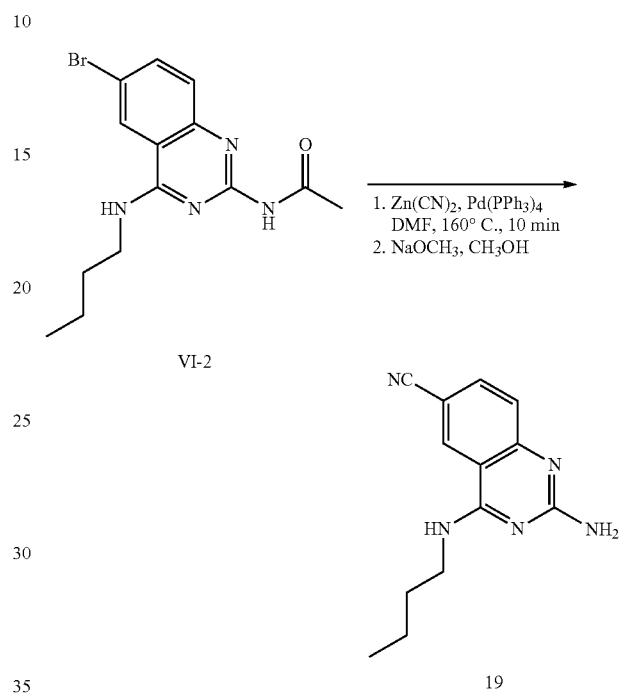

A mixture of VI-2 (500 mg, 1.48 mmol), tetrakis(triphenylphosphine)palladium (86 mg, 0.074 mmol), and zinc cyanide (106 mg, 0.89 mmol) in DMF (5 mL) in a 10 mL tube was placed under microwave irradiation at 160° C. for 10 minutes. The mixture was cooled to room temperature and concentrated in vacuo. The residue was partioned between water and dichloromethane. The organic layer was separated, dried (MgSO₄), the solvents were removed by filtration and the solvents of the filtrate were concentrated in vacuo. The product was triturated in CH₃CN, the solid was isolated by filtration. Acyl deprotection was afforded after treatment with sodium methoxide in methanol at 60° C. for one hour. The mixture was cooled and the product precipitated. The white solid, 19, was isolated by filtration and dried under vacuum.

Preparation of 20

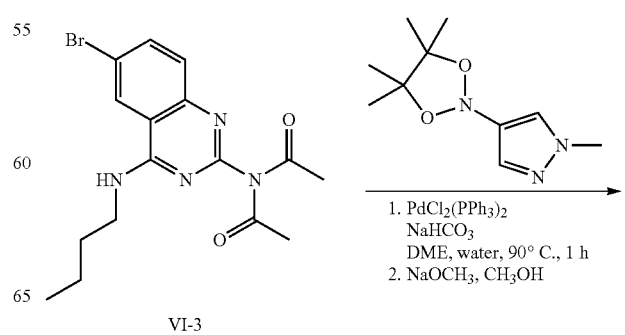

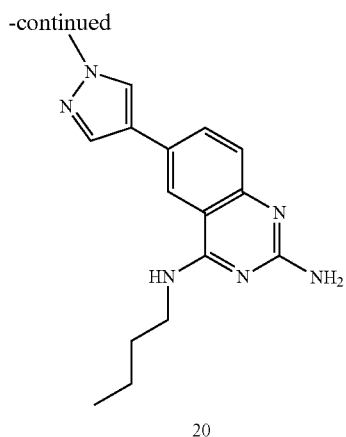

20

Into a 50 mL vial equipped with a magnetic stir bar and sparged with nitrogen gas was placed VI-3 (300 mg, 0.79 mmol), the boronic ester (198 mg, 0.95 mmol), water (3 mL, degassed) and DME (6 mL, degassed), sodium bicarbonate (199 mg, 2.37 mmol) and PdCl$_2$(PPh$_3$)$_2$ (55 mg, 0.079 mmol) was added and the mixture was heated to 90° C. for 1 hour. The mixture was cooled and ethyl acetate was added. The organic layer was separated, dried (MgSO$_4$), the solids were removed by filtration and the solvents of the filtrate were removed in vacuo. The residue was purified via silica gel column chromatography using a gradient of dichloromethane to 10% methanol in dichloromethane (containing ammonia). The product fractions were collected and concentrated in vacuo. Acyl deprotection was afforded after treatment with sodium methoxide in methanol at 60° C. for one hour. The solvents were removed under reduced pressure and the residue was partitioned between water and dichloromethane. The organic layer was separated, dried (MgSO$_4$), the solvents were removed via filtration and the solvents of the filtrate were removed in vacuo. The product was crystallized from CH$_3$CN, isolated by filtration and dried in vacuo to obtain a white solid, 20.

Preparation of 21

In a first vial equipped with a magnetic stir bar and a screw cap septum, a solution of Pd$_2$(dba)$_3$ (6 mg, 0.007 mmol) and 2-di-tert-butylphosphino-3,4,5,6-tetramethyl-2',4',6'-triisopropyl-1,1'-biphenyl (6 mg, 0.013 mmol) in toluene (0.5 mL) was flushed with N$_2$ gas then stirred at 120° C. for 3 minutes. A second vial, equipped with a magnetic stir bar and a screw cap septum, was charged with 2-methylimidazole (104 mg, 1.26 mmol) and K$_3$PO$_4$ (224 mg, 1.05 mmol), then VI-3 (200 mg, 0.53 mmol) and also flushed with N$_2$ (g). The premixed catalyst solution followed by anhydrous toluene (0.5 mL) and t-butanol (1.0 mL) were added via syringe to the second vial (total 2 mL of toluene: t-BuOH 1:1 solution). The reaction was heated to 120° C. for 12 hours. The mixture was cooled and sodium methoxide (30% in methanol) was added. The mixture was heated at 60° C. for 1 hour. The mixture was cooled to room temperature and concentrated in vacuo. The residue was partioned between water and dichloromethane. The organic layer was separated, dried (MgSO$_4$), the solids were removed by filtration and the solvents of the filtrate were concentrated in vacuo. The crude was purified by Prep HPLC (RP SunFire Prep C18 OBD-10 µm, 30×150 mm). Mobile phase (0.25% NH$_4$HCO$_3$ solution in water, CH$_3$CN). The product fractions were collected and concentrated in vacuo to afford compound 21.

Preparation of 22

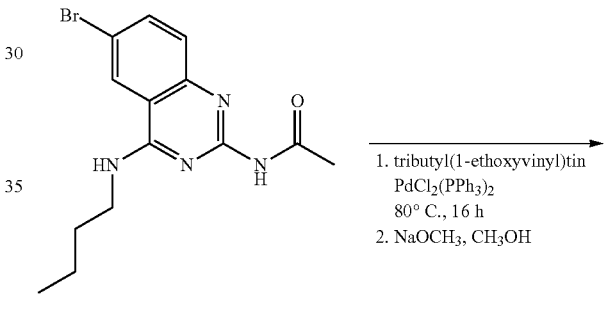

A mixture of VI-2 (500 mg, 1.48 mmol), tributyl(1-ethoxyvinyl)tin (0.626 mL, 1.85 mmol), PdCl$_2$(PPh$_3$)$_2$ (220 mg, 0.31 mmol) in DMF (10 mL) was heated to 80° C. for 16 hours. The reaction mixture was cooled and HCl (1N, 2 mL) was added. The mixture was stirred at room temperature for 2 hours then was poured into sat. aq. NaHCO$_3$ (100 mL) and the precipitate was isolated by filtration, reconstituted in dichloromethane, dried (MgSO$_4$), the solids were removed by filtration and the solvents of the filtrate were concentrated in vacuo. The product was purified via silica gel column chromatography using a gradient of dichloromethane to 5% methanol in dichloromethane, the product fractions were collected and concentrated in vacuo. The product was triturated in DIPE, filtered and dried under vacuum to become a pale yellow solid. To the mixture was added methanol (6 mL) and sodium methoxide (0.716 mL) and was stirred at 60° C. for 1 hour. The mixture was cooled and concentrated in vacuo. The residue was partioned between water and dichloromethane. The organic layer was separated, dried (MgSO₄), the solids were removed by filtration and solvents of the filtrate were concentrated in vacuo. The product was triturated in DIPE, isolated by filtration and dried under vacuum to become a yellow solid, 22.

Preparation of 23

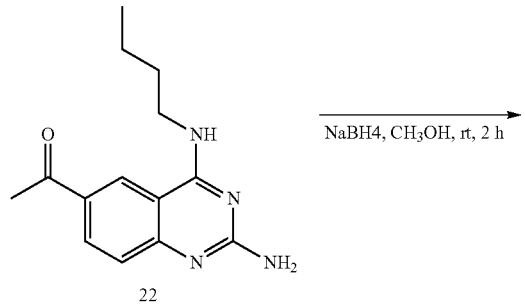

22 (59 mg, 0.23 mmol) was suspended in methanol (2 mL) and sodium borohydride (9 mg, 0.23 mmol) was added. The mixture was stirred under N₂ (g) at room temperature for two hours. The mixture was diluted with dichloromethane (5 mL), then sat., aq. NH₄Cl (0.5 mL) was added followed by addition of NaHCO₃. The organic layer was dried (MgSO₄), the solids were removed via filtration and the solvents of the filtrate were concentrated in vacuo. The product was triturated in DIPE, isolated by filtration and dried under vacuum to become a pale yellow solid, 23.

Preparation of 24

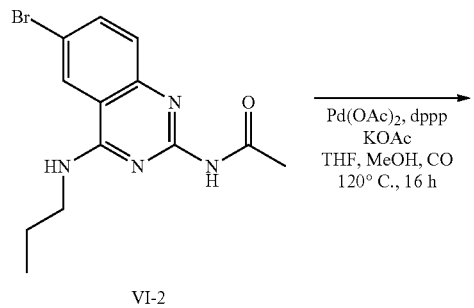

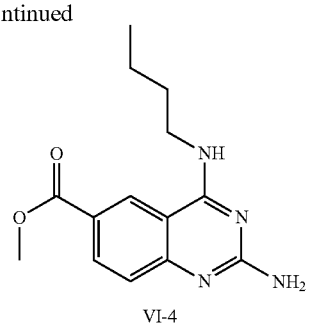

Step 1. A 75 mL stainless steel autoclave was charged under nitrogen atmosphere with VI-2 (626 mg, 1.87 mmol), Pd(OAc)₂ (8 mg, 0.037 mmol), 1,3-bis(diphenylphosphino)propane (31 mg, 0.074 mmol), potassium acetate (364 mg, 3.71 mmol), THF (20 mL), and methanol (20 mL). The autoclave was closed and pressurized to 30 bar CO (g). The reaction mixture was stirred for 16 hours at 120° C. The reaction mixture was allowed to cool to room temperature then concentrated in vacuo. The residue was dissolved in water and extracted with dichloromethane. The organic layer was dried (MgSO₄), the solids were removed by filtration and the solvent of the filtrate was concentrated in vacuo. The product was purified on a silica column using a dichloromethane to 5% methanol in dichloromethane gradient. The product fractions were collected and concentrated in vacuo to obtain an off-white solid, VI-4.

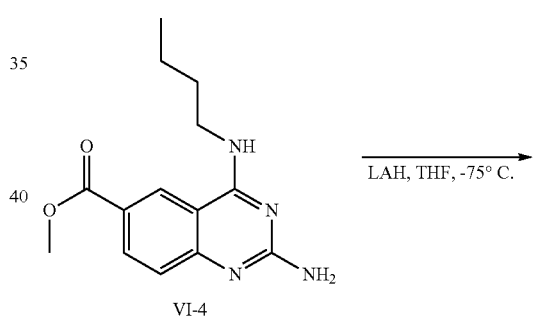

Step 2. To a solution of VI-4 (190 mg, 0.69 mmol) in anhydrous THF (20 mL) was added LAH (1M in THF, 1.04 mL, 1.04 mmol) at −75° C. under a nitrogen atmosphere. The reaction was allowed to stir for two hours while it slowly warmed to 0° C. Then the mixture was cooled on a ice-ethanol bath and carefully quenched by adding 15 mL ethyl acetate followed by Na₂SO₄ 10H₂O (2 g). The mixture was stirred for one hour and then dried over MgSO₄, the solids were removed by filtration and the solvent of the filtrate was removed under reduced pressure. The residue was purified by prep. HPLC (RP Vydac Denali C18-10 μm, 200 g, 5 cm). Mobile phase (0.25% NH₄HCO₃ solution in water, CH₃CN), followed by SFC purification (Chiralpak Diacel AD 30×250 mm). Mobile phase (CO₂, methanol with 0.2% isopropylamine), the desired fractions were collected, and the solvents were removed under reduced pressure to afford 24.

Preparation of 25

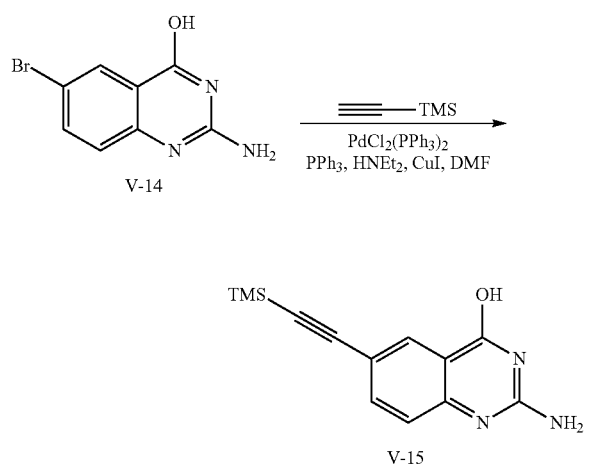

Step 1. V-14 was reacted with trimethylacetylene according to the method to prepare compound 14, to afford V-15.

LC-MS m/z=258 (M+H)

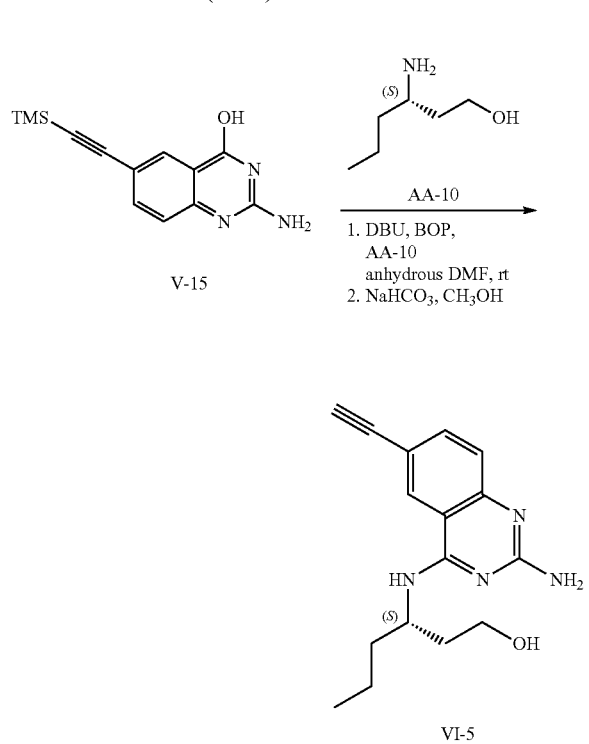

Step 2. VI-5 was prepared according to the method to prepare compound 9. Deprotection of the TMS group was performed in a NaHCO3, water, methanol mixture.

LC-MS m/z=357 (M+H)

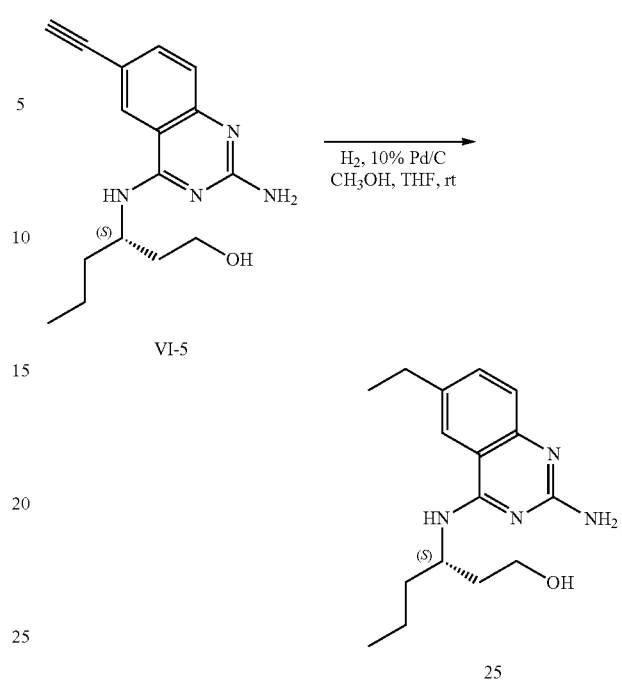

Step 3. The hydrogenation was performed according to the method to prepare 16.

Preparation of 26

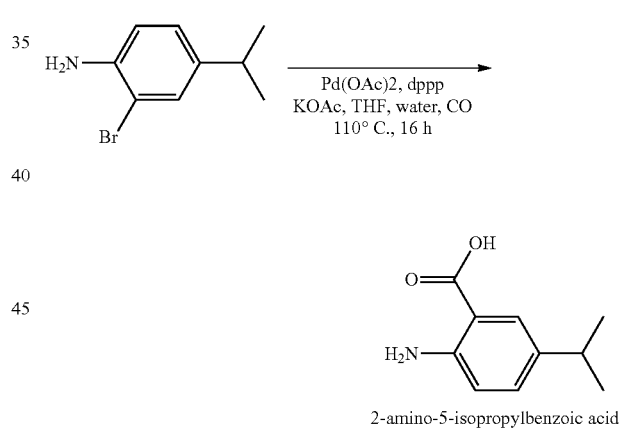

Step 1. Palladium catalyzed carbonylation of 2-bromo-4-isopropylaniline was performed according to the procedure to prepare VI-4 with the exception that the reaction was run at 110° C. to afford 2-amino-5-isopropylbenzoic acid.

LC-MS m/z=180 (M+H)

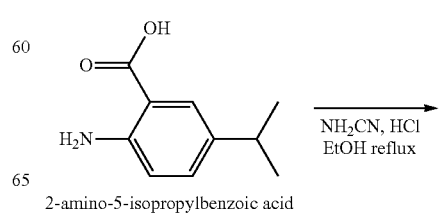

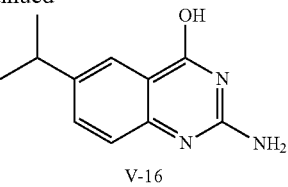

Step 2. V-16 was prepared according to the method to prepare V-1.

LC-MS m/z=204 (M+H)

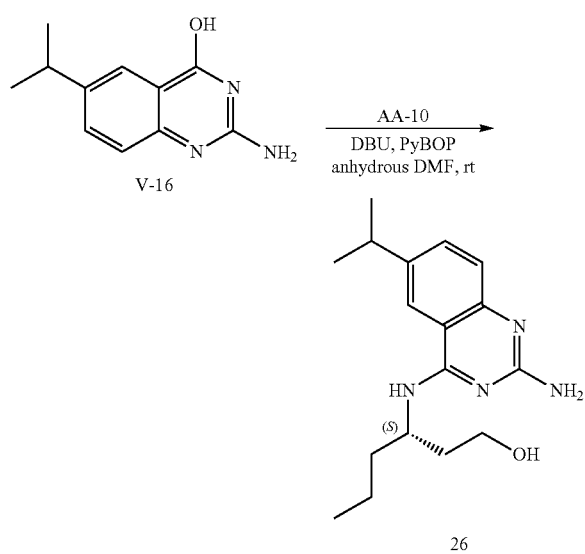

Step 3. Example 26 was prepared according to the method to prepare 15.

Preparation of 27

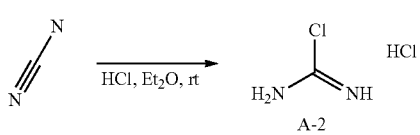

Step 1. Cyanamide was dissolved in ether and the mixture was stirred under nitrogen gas. HCl (2M in ether) was added dropwise to the reaction mixture at ambient temperature and stirring continued for 2 hours at room temperature. The precipitate, A-2 was isolated by filtration and dried in vacuo at 50° C.

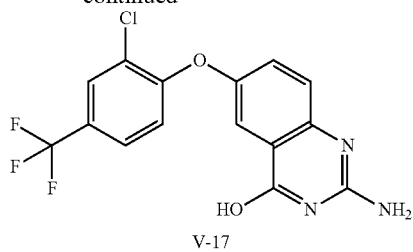

Step 2. $SO_2(CH_3)_2$ (20.4 g, 217 mmol) was heated to melting. A-2 (3.3 g, 29 mmol) was added and the resulting mixture was stirred and heated to 120° C. to dissolve completely. Methyl 5-(2-chloro-4-trifluoromethylphenoxy)-anthranilate (5 g, 14.5 mmol) was added in one part to the reaction mixture. Stirring was continued for 30 minutes. The reaction mixture was treated with water (10 mL) and stirred for 10 minutes. The precipitate, V-17, a white solid, was isolated by filtration and dried in the vacuum oven.

LC-MS m/z=356 (M+H)

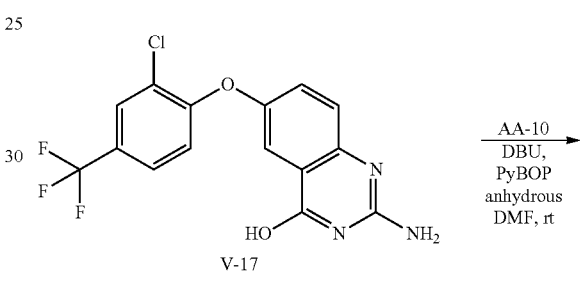

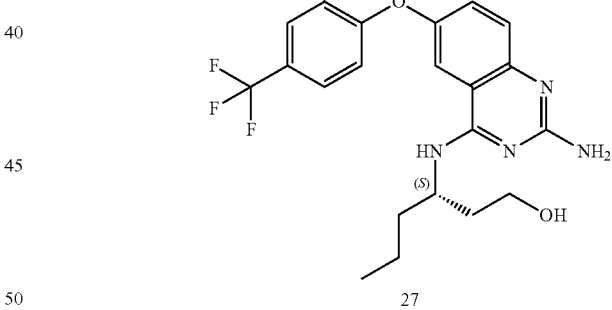

Step 3. Compound 27 was formed according to the method to prepare 15.

Preparation of 28

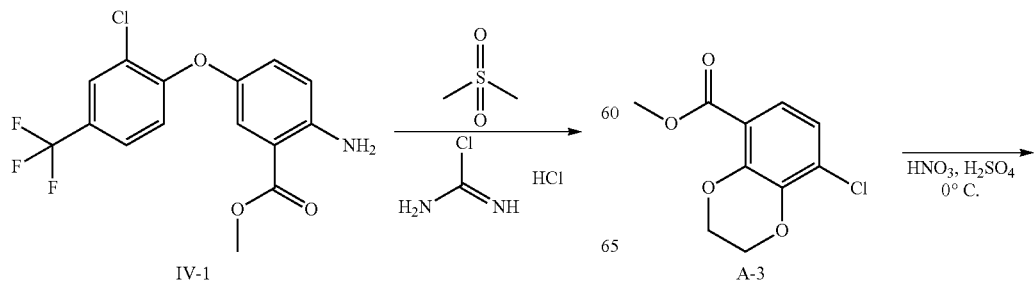

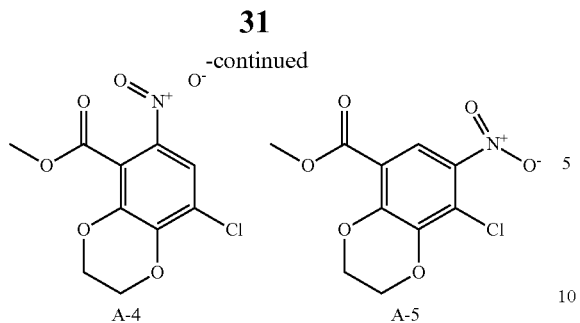

Step 1. A-3 (101 g, 0.44 mol) was dissolved in sulfuric acid (850 mL). This solution was cooled to 0° C. HNO₃ (18.3 mL, 0.44 mol) in sulfuric acid (200 mL) was added dropwise over 2 hours. The reaction mixture was stirred for 45 minutes at −10° C., then poured into ice-water (6 L). The solvents were decanted and the residue was dissolved in dichloromethane (1.5 L). The aqueous layer was extracted with dichloromethane (1 L). The combined organic layers were dried (MgSO₄), the solids were removed by filtration and the solvent was removed under reduced pressure to afford A-4, and the side product isomer A-5, separated via silica gel column chromatography using a heptane to ethyl acetate gradient.

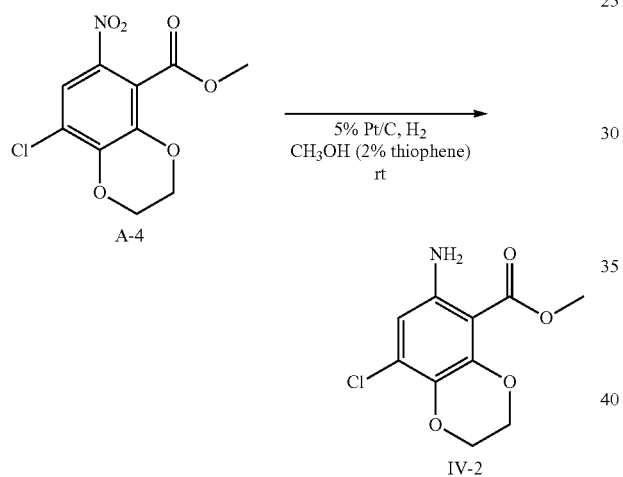

Step 2. Into a 500 mL erlenmeyer flask equipped with a magnetic stir bar and sparged with nitrogen gas was placed methanol (100 mL, containing 2% thiophene), 5% Pt/C (2 g, 0.513 mmol) then placed under a hydrogen atmosphere. The reaction mixture was stirred for 16 hours at room temperature. The catalyst was removed by filtration and the volatiles of the filtrate were removed under reduced pressure. The residue was purified on silica using a dichloromethane to dichloromethane:methanol 9:1 gradient yielding a yellow oil, IV-2.

LC-MS m/z=244 (M+H)

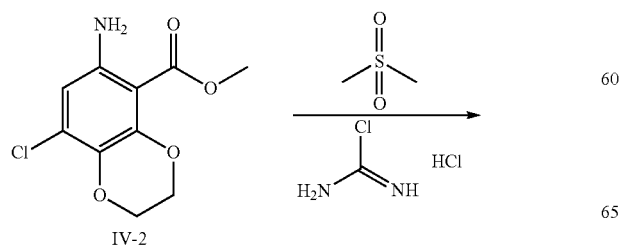

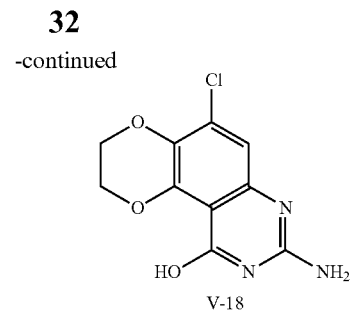

Step 3. Intermediate V-18 was prepared according to the method to prepare V-17.

LC-MS m/z=254 (M+H)

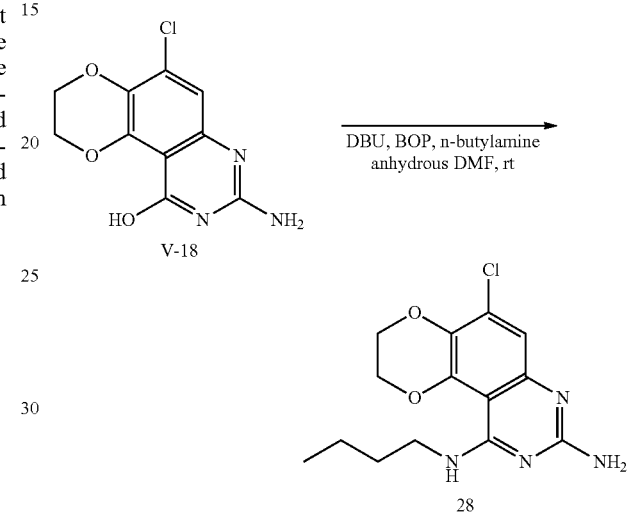

Step 4. The procedure to prepare compound 9 was applied in the synthesis of 28 from V-18.

Preparation of Compound 29

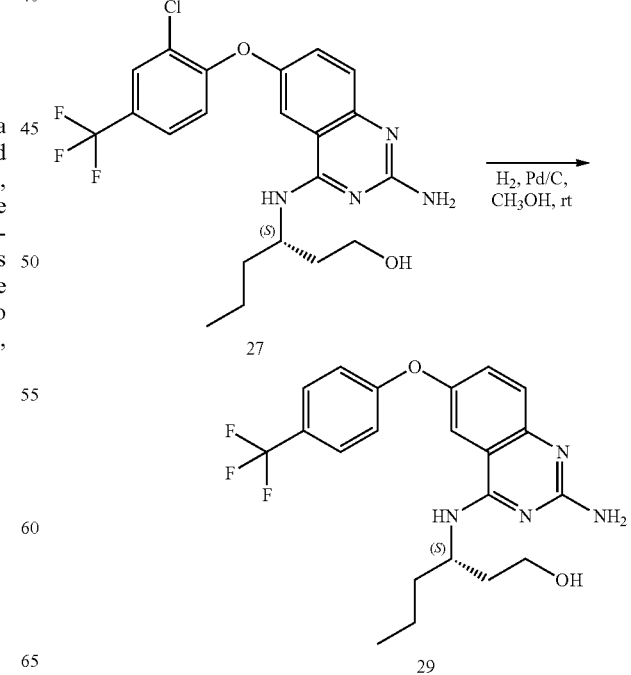

Step 1. Example 29 was afforded after catalytic hydrogenation of 27, according to the method described in the preparation of 25.

Preparation of 90

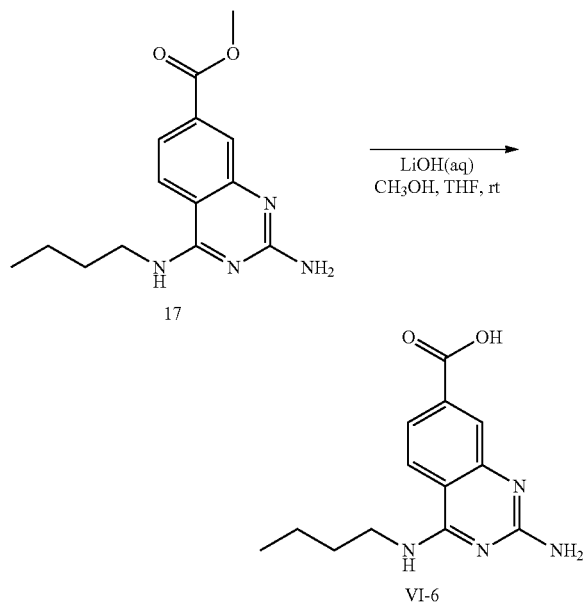

Step 1. 17 (12.515 g, 45.62 mmol) was dissolved in THF (100 mL). LiOH (3.83 g, 91.2 mmol) dissolved in water (20 mL) was added, followed by methanol (50 mL). The reaction mixture was stirred overnight at room temperature. The volatiles were removed under reduced pressure, the solid was washed with water and triturated with DIPE to afford VI-6 as off-white solid.

$^1$H NMR (400 MHz, DMSO-$d_6$) δ ppm 0.95 (t, J=7.4 Hz, 3H), 1.40 (dq, J=14.9, 7.3 Hz, 2H), 1.68 (quin, J=7.3 Hz, 2H), 3.54-3.65 (m, 2H), 7.89-8.05 (m, 2H), 8.14-8.31 (m, 2H), 9.11 (br. s., 1H), 11.10 (br. s., 1H), 16.37 (br. s., 1H)

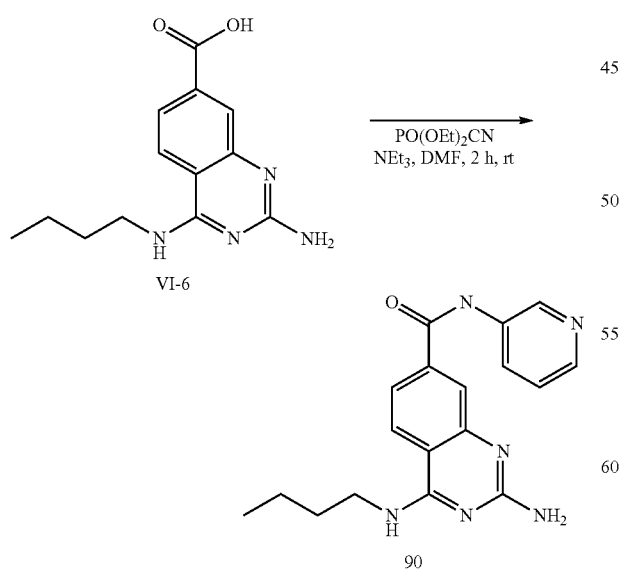

Step 2. Into a 50 mL vial was placed VI-6 (200 mg, 0.768 mmol), DMF (10 mL), triethylamine (0.641 mL, 4.61 mmol), 3-aminopyridine (181 mg, 1.92 mmol) and diethyl cyanophosphonate (0.233 mL, 1.54 mmol). The reaction was allowed to stir for 2 hours at room temperature. The solvent was removed under reduced pressure and the crude was purified via reverse phase column chromatography (Sunfire Prep C18, OBD 10 μm, 30×150 mm. Mobile phase (0.25% NH$_4$HCO$_3$ solution in water, methanol) to afford 90.

Synthetic Scheme for the Preparation of AA-9

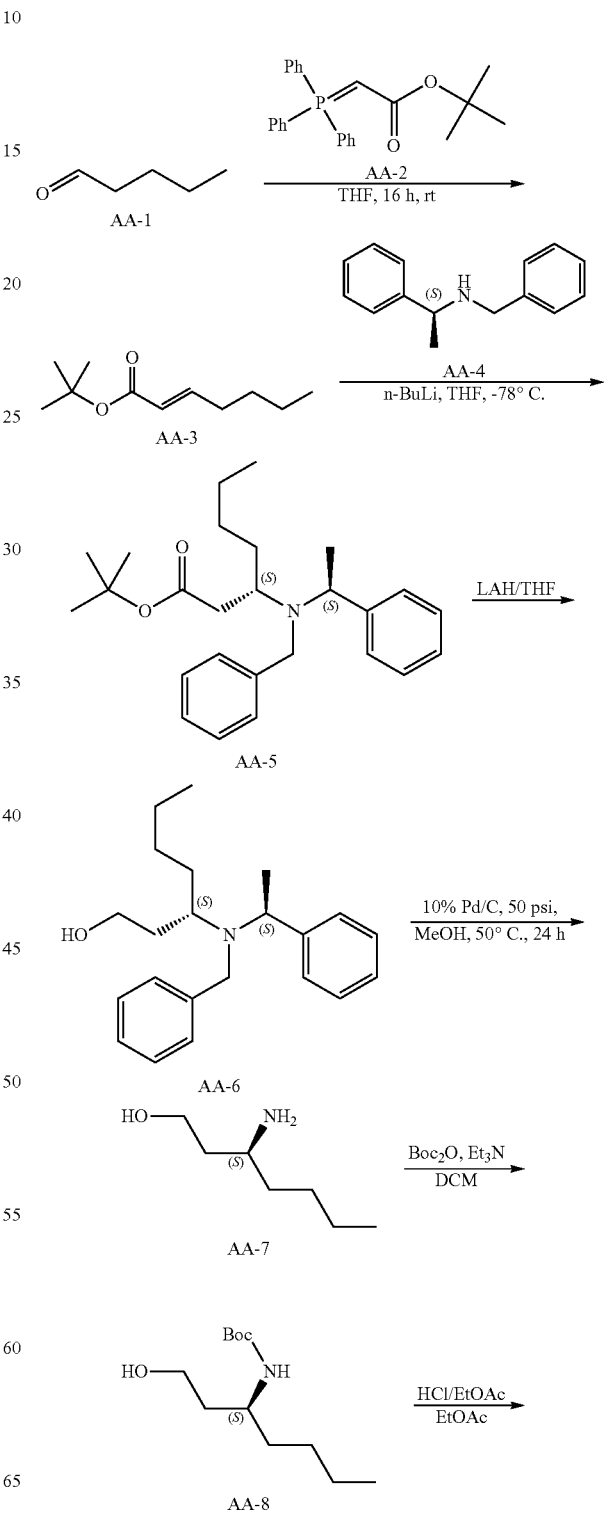

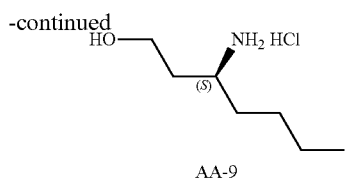

Synthesis of Intermediate AA-3

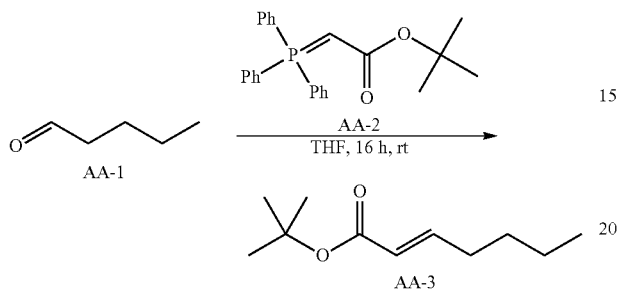

To a solution of valeraldehyde (43 g, 500 mmol) in THF (1 L) was added AA-2 (200 g, 532 mmol) and the reaction mixture was stirred for 16 hours at room temperature. The solvents were evaporated and the residue was diluted in petroleum ether and filtered. The solvents of the filtrate were removed under reduced pressure and the residue was purified by silica chromatography using a petroleum ether to 3% ethyl acetate in petroleum ether gradient to give AA-3 (90 g) as a colorless oil.

$^1$H NMR (400 MHz, CDCl$_3$): δ ppm 6.81-6.77 (m, 1H), 5.68-5.64 (td, J=1.2 Hz, 15.6 Hz, 1H), 2.11-2.09 (m, 2H), 1.406 (s, 9H), 1.38-1.26 (m, 4H), 0.85-0.81 (t, J=7.2 Hz, 3H).

Synthesis of Compound AA-5

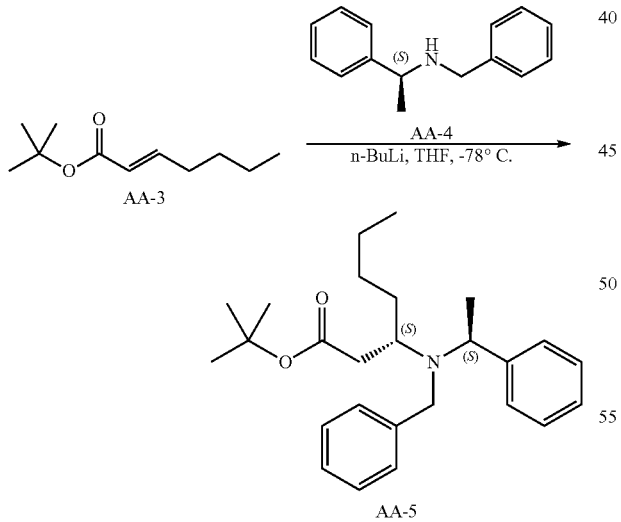

n-butyl lithium (290 mL, 725 mmol, 1.5 eq.) was added to a stirred solution of AA-4 (165 g, 781 mmol) in THF (800 mL) at −78° C. The reaction mixture was stirred for 30 minutes then AA-3 (90 g, 488.4 mmol) in THF (400 mL) was added and the reaction was stirred for 2 hours at −78° C. The mixture was quenched with sat., aq. NH$_4$Cl solution and warmed to room temperature. The product was partitioned between ethyl acetate and water. The organic phase was washed with brine, dried and evaporated. The residue was purified by column chromatography eluting with 5% ethyl acetate in petroleum ether to afford a colorless oil, AA-5 (132 g).

$^1$H NMR (400 MHz, CDCl$_3$): δ ppm 7.36-7.16 (m, 10H), 3.75-3.70 (m, 2H), 3.43-3.39 (d, J=15.2 Hz, 1H), 3.33-3.15 (m, 1H), 1.86-1.80 (m, 2H), 1.47-1.37 (m, 2H), 1.32 (s, 9H), 1.26-1.17 (m, 7H), 0.83-0.79 (t, J=7.2 Hz, 3H).

Synthesis of AA-6

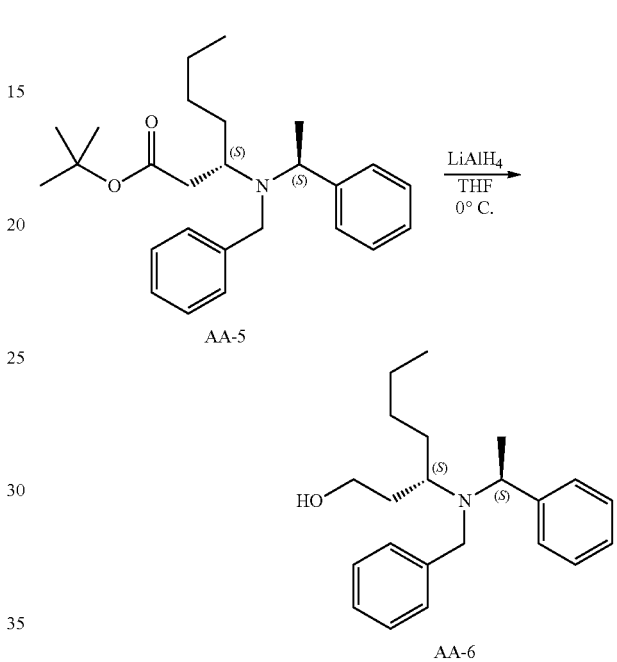

AA-5 (130 g, 328 mmol) was dissolved in THF (1.5 L) and LAH (20 g, 526 mmol) was added at 0° C. in small portions. The resulting mixture was stirred at the same temperature for 2 hours and then allowed to warm to room temperature. The mixture was quenched with a sat. aq. NH$_4$Cl solution. The product was partitioned between ethyl acetate and water. The organic phase was washed with brine, dried and evaporated. The combined organic layers were dried over sodium sulfate, the solids were removed via filtration and concentrated to afford crude AA-6 (100 g), which was used in the next step without further purification.

$^1$H NMR (400 MHz, CDCl$_3$): δ ppm 7.33-7.14 (m, 10H), 3.91-3.86 (m, 1H), 3.80-3.77 (d, J=13.6 Hz, 1H), 3.63-3.60 (d, J=13.6 Hz, 1H), 3.43-3.42 (m, 1H), 3.15-3.10 (m, 1H), 2.70-2.63 (m, 2H), 1.65-1.28 (m, 10H), 0.89-0.81 (m, 3H).

Synthesis of AA-9

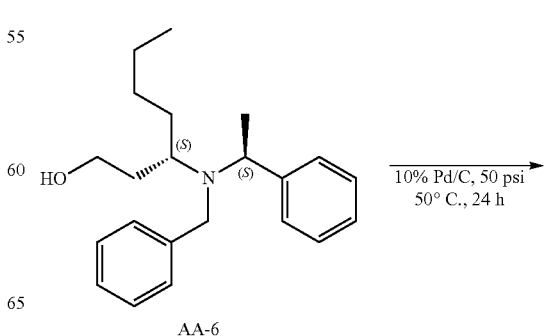

-continued

HO—CH2CH2—C(S)(NH2)—CH2CH2CH2CH3
AA-7

(Boc)₂O, Et₃N, DCM →

HO—CH2CH2—C(S)(NHBoc)—CH2CH2CH2CH3
AA-8

HCl/EtOAc
EtOAc ↓

HO—CH2CH2—C(S)(NH2·HCl)—CH2CH2CH2CH3
AA-9

A solution of AA-6 (38 g, 116.75 mmol) and 10% Pd/C in methanol (200 mL) was hydrogenated under 50 PSI hydrogen at 50° C. for 24 hours. The reaction mixture was filtered and the solvent was evaporated to give crude product AA-7 (17 g).

The crude product was dissolved in dichloromethane (200 mL), triethylamine (26.17 g, 259.1 mmol) and di-tert-butyl dicarbonate (84.7 g, 194.4 mmol) was added at 0° C. The resulting mixture was stirred at room temperature for 16 hours. The mixture was partitioned between dichloromethane and water. The organic phase was washed with brine, dried and evaporated. The residue was purified by silica gel chromatography eluting with 20% ethyl acetate in petroleum ether to give AA-8 (13 g) as colorless oil.

¹H NMR (400 MHz, CDCl₃): δ ppm 4.08-4.03 (br, 1H), 3.68 (m, 1H), 3.58-3.55 (m, 2H), 3.20-2.90 (br, 1H), 1.80-1.73 (m, 1H), 1.42-1.17 (m, 15H), 0.85-0.82 (t, J=6.8 Hz, 3H).

AA-8 (42 g, 0.182 mol) was dissolved in dioxane (200 mL) and dioxane/HCl (4M, 200 mL) was added at 0° C. The resulting mixture was stirred at room temperature for 2 h. The solvent was evaporated to afford the crude product. A dichloromethane/petroleum ether mixture (50 mL, 1:1, v/v) was added to the crude product, and the supernatant was decanted. This procedure was repeated two times to obtain an oil, AA-9 (26.6 g).

¹H NMR (400 MHz, DMSO-d₆): δ ppm 8.04 (s, 3H), 3.60-3.49 (m, 2H), 3.16-3.15 (m, 1H), 1.71-1.67 (m, 2H), 1.60-1.55 (m, 2H), 1.33-1.26 (m, 4H), 0.90-0.87 (t, J=6.8 Hz, 3H).

Preparation of AA-10

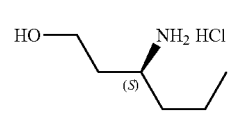
AA-10

AA-10 was prepared according to the preparation of AA-9, using butyraldehyde instead of valeraldehyde.

¹H NMR (400 MHz, DMSO-d₆): δ ppm 8.07 (s, 3H), 4.85 (br, 1H), 3.57-3.45 (m, 2H), 3.14-3.12 (m, 1H), 1.70-1.64 (m, 2H), 1.56-1.49 (m, 2H), 1.38-1.30 (m, 2H), 0.90-0.80 (t, J=6.8 Hz, 3H).

TABLE 1

Compounds of formula (I).

| # | STRUCTURE | H NMR | Method, Rt | Synthetic Method |
|---|---|---|---|---|
| 1 | (quinazoline structure with dimethoxy and N-butyl amino substituents) | ¹H NMR (360 MHz, DMSO-d₆) δ ppm 0.93 (t, J = 7.3 Hz, 3 H), 1.31-1.43 (m, 2 H), 1.60 (t, J = 7.1 Hz, 2 H), 3.40-3.48 (m, 2 H), 3.79 (s, 3 H), 3.79 (s, 3 H), 5.67 (s, 2 H), 6.63 (s, 1 H), 7.40 (s, 1 H), 7.44-7.50 (m, 1 H) | A, 0.67 | |
| 2 | (quinazoline structure with dimethoxy and N-pentyl amino substituents) | ¹H NMR (360 MHz, DMSO-d₆) δ ppm 0.85-0.93 (m, 3 H), 1.27-1.37 (m, 4 H), 1.57-1.68 (m, 2 H), 3.39-3.49 (m, 2 H), 3.78 (s, 3 H), 3.79 (s, 3 H), 5.67 (s, 2 H), 6.63 (s, 1 H), 7.40 (s, 1 H), 7.47 (t, J = 5.7 Hz, 1 H) | A, 0.86 | Same method as to prepare 1. |

TABLE 1-continued

Compounds of formula (I).

| # | STRUCTURE | H NMR | Method, Rt | Synthetic Method |
|---|---|---|---|---|
| 3 | 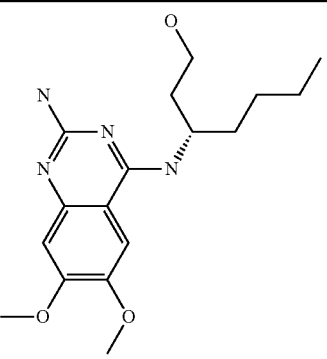 | $^1$H NMR (360 MHz, DMSO-d$_6$) δ ppm 0.79-0.91 (m, 3 H), 1.29 (m, J = 3.3 Hz, 4 H), 1.59 (m, J = 6.6 Hz, 2 H), 1.64-1.70 (m, 1 H), 1.72-1.79 (m, 1 H), 3.40-3.50 (m, 2 H), 3.80 (s, 3 H), 3.80 (s, 3 H), 4.33-4.43 (m, 1 H), 4.48 (t, J = 5.1 Hz, 1 H), 5.68 (s, 2 H), 6.63 (s, 1 H), 7.09 (d, J = 8.4 Hz, 1 H), 7.44 (s, 1 H) | A, 0.74 | Same method as to prepare 1. |
| 4 | 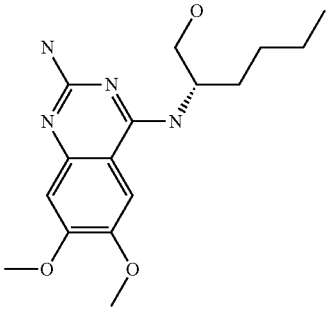 [SMILES: CCCC[C@@H](CO)Nc1nc(N)nc2cc(OC)c(OC)cc12] | $^1$H NMR (400 MHz, CHLOROFORM-d) δ ppm 0.91 (t, J = 7.0 Hz, 3 H), 1.28-1.48 (m, 5 H), 1.58-1.77 (m, 2 H), 3.48 (s, 1 H), 3.72 (dd, J = 11.0, 6.3 Hz, 1 H), 3.88 (s, 3 H), 3.91 (s, 3 H), 4.34 (td, J = 6.8, 2.8 Hz, 1 H), 4.78 (br. s., 2 H), 5.64 (d, J = 7.0 Hz, 1 H), 6.81 (s, 1 H), 6.81 (s, 1 H) | A, 0.68 | Same method as to prepare 1. |
| 5 | 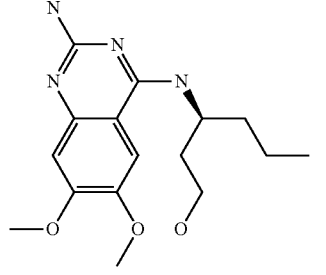 [SMILES: CCC[C@@H](CCO)Nc1nc(N)nc2cc(OC)c(OC)cc12] | $^1$H NMR (360 MHz, DMSO-d$_6$) δ ppm 0.88 (t, J = 7.3 Hz, 3 H), 1.23-1.42 (m, 2 H), 1.48-1.81 (m, 4 H), 3.39-3.48 (m, 2 H), 3.79 (s, 3 H), 3.80 (s, 3 H), 4.38-4.46 (m, 1 H), 4.49 (t, J = 5.3 Hz, 1 H), 5.68 (s, 2 H), 6.63 (s, 1 H), 7.08 (d, J = 8.4 Hz, 1 H), 7.44 (s, 1 H) | A, 0.69 | Same method as to prepare 1. |
| 6 | 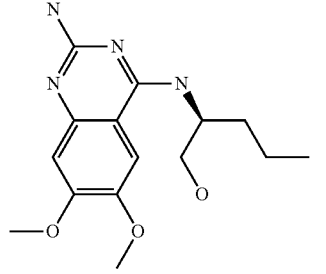 [SMILES: CCC[C@@H](CO)Nc1nc(N)nc2cc(OC)c(OC)cc12] | $^1$H NMR (400 MHz, CHLOROFORM-d) δ ppm 0.95 (t, J = 7.3 Hz, 3 H), 1.35-1.52 (m, 2 H), 1.60-1.71 (m, 2 H), 3.48 (s, 1 H), 3.71 (dd, J = 11.0, 6.3 Hz, 1 H), 3.85 (s, 3 H), 3.85-3.88 (m, 1 H), 3.90 (s, 3 H), 4.37 (td, J = 6.7, 3.3 Hz, 1 H), 4.85 (br. s., 2 H), 5.82 (d, J = 7.3 Hz, 1 H), 6.78 (s, 1 H), 6.85 (s, 1 H) | A, 0.69 | Same method as to prepare 1. |
| 7 | 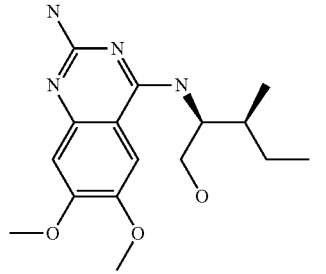 [SMILES: CC[C@H](C)[C@@H](CO)Nc1nc(N)nc2cc(OC)c(OC)cc12] | $^1$H NMR (400 MHz, CHLOROFORM-d) δ ppm 0.89-0.96 (m, 4 H), 1.01 (d, J = 1.0 Hz, 4 H), 1.25 (ddd, J = 13.7, 8.5, 7.4 Hz, 1 H), 1.47-1.65 (m, 1 H), 1.77-1.92 (m, 1 H), 3.48 (s, 0 H), 3.81-3.84 (m, 1 H), 3.87 (s, 3 H), 3.87 (s, 3 H), 4.21-4.31 (m, 1 H), 5.15 (br. s., 2 H), 6.04-6.11 (m, 1 H), 6.74 (s, 1 H), 6.86 (s, 1 H) | | Same method as to prepare 1. |

TABLE 1-continued

Compounds of formula (I).

| # | STRUCTURE | H NMR | Method, Rt | Synthetic Method |
|---|---|---|---|---|
| 8 | 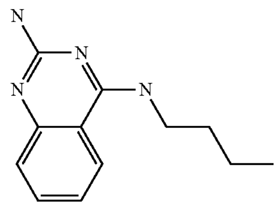 [SMILES: CCCCNc1nc(N)nc2ccccc12] | $^1$H NMR (400 MHz, DMSO-$d_6$) δ ppm 0.89-0.96 (m, 3 H), 1.31-1.43 (m, 2 H), 1.57-1.67 (m, 2 H), 3.44-3.52 (m, 2 H), 6.04 (s, 2 H), 7.01 (ddd, J = 8.1, 7.0, 1.0 Hz, 1 H), 7.20 (dd, J = 8.4, 0.9 Hz, 1 H), 7.46 (ddd, J = 8.3, 6.9, 1.4 Hz, 1 H), 7.75 (t, J = 5.4 Hz, 1 H), 7.98 (dd, J = 8.2, 0.9 Hz, 1 H) | A, 0.64 | Same method as to prepare 1. |
| 9 | 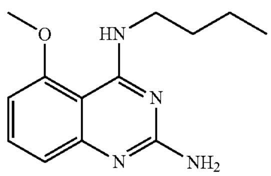 [SMILES: CCCCNc1nc(N)nc2cccc(OC)c12] | $^1$H NMR (400 MHz, DMSO-$d_6$) δ ppm 0.94 (t, J = 7.4 Hz, 3 H), 1.29-1.44 (m, 2 H), 1.63 (t, J = 7.3 Hz, 2 H), 3.55-3.64 (m, 2 H), 4.02 (s, 3 H), 6.99 (dd, J = 8.3, 1.8 Hz, 2 H), 7.69 (t, J = 8.3 Hz, 1 H), 7.81-8.29 (m, 2 H), 9.10 (s, 1 H), 12.49 (s, 1 H) | C, 0.83 | |
| 10 | 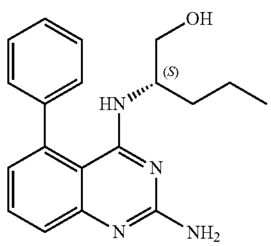 | $^1$H NMR (360 MHz, DMSO-$d_6$) δ ppm 0.80 (t, J = 1.00 Hz, 3 H) 0.83-0.93 (m, 1 H) 0.96-1.17 (m, 2 H) 1.20-1.35 (m, 1 H) 3.10-3.26 (m, 2 H), 3.36 (br. s., 2 H) 4.12 (td, J = 8.23, 4.39 Hz, 1 H) 4.56-4.74 (m, 1 H) 5.96 (d, J = 8.42 Hz, 1 H) 7.18 (d, J = 1.00 Hz, 1 H) 7.37-7.64 (m, 6 H) 7.81 (t, J = 1.00 Hz, 1 H) | C, 0.88 | |
| 11 | 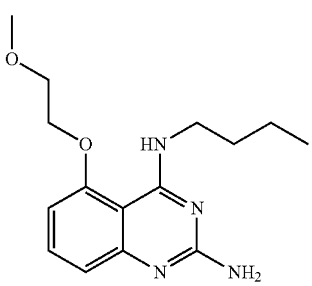 [SMILES: CCCCNc1nc(N)nc2cccc(OCCOC)c12] | $^1$H NMR (400 MHz, DMSO-$d_6$) δ ppm 0.94 (t, J = 7.28 Hz, 3 H) 1.36-1.46 (m, 2 H) 1.55-1.63 (m, 2 H) 3.37 (s, 3 H) 3.44 (td, J = 6.96, 5.14 Hz, 2 H) 3.74-3.80 (m, 2 H) 4.24 (dd, J = 5.27, 3.76 Hz, 2 H) 6.04 (br. s, 2 H) 6.57 (d, J = 7.53 Hz, 1 H) 6.77-6.81 (m, 1 H) 7.34 (t, J = 8.16 Hz, 1 H) 7.97 (t, J = 5.02 Hz, 1 H) | C, 0.85 | See experimental section |
| 12 | 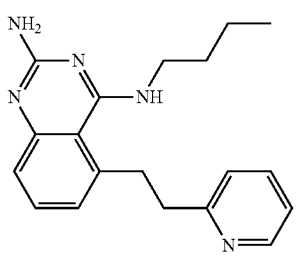 [SMILES: CCCCNc1nc(N)nc2cccc(CCc3ccccn3)c12] | $^1$H NMR (400 MHz, DMSO-$d_6$) δ ppm 0.90 (t, J = 7.37 Hz, 3 H) 1.32-1.42 (m, 2 H) 1.63-1.71 (m, 2 H) 3.05-3.12 (m, 2 H) 3.38-3.48 (m, 2 H) 3.52-3.59 (m, 2 H) 5.93 (s, 2 H) 6.88 (dd, J = 7.15, 1.21 Hz, 1 H) 7.07 (dd, J = 8.25, 1.21 Hz, 1 H) 7.23-7.34 (m, 4 H) 7.71-7.76 (m, 1 H) 8.53-8.56 (m, 1 H) | C, 0.99 | See experimental section |
| 13 | 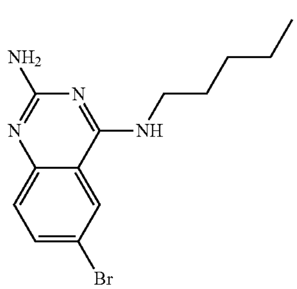 [SMILES: CCCCCNc1nc(N)nc2ccc(Br)cc12] | $^1$H NMR (400 MHz, DMSO-$d_6$) δ ppm 0.85-0.93 (m, 3 H), 1.25-1.40 (m, 4 H), 1.61 (t, J = 6.9 Hz, 2 H), 3.39-3.48 (m, 2 H), 6.13 (s, 2 H), 7.11 (d, J = 9.0 Hz, 1 H), 7.55 (dd, J = 8.8, 2.3 Hz, 1 H), 7.79-7.90 (m, 1 H), 8.25 (d, J = 2.3 Hz, 1 H) | C, 0.99 | Same method as to prepare 9 |

TABLE 1-continued

Compounds of formula (I).

| # | STRUCTURE | H NMR | Method, Rt | Synthetic Method |
|---|-----------|-------|------------|------------------|
| 14 | 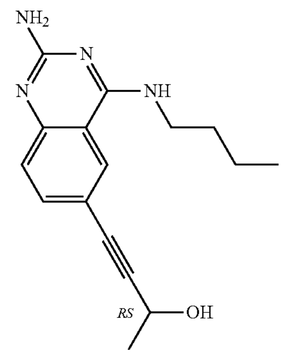 [SMILES: CCCCNc1nc(N)nc2ccc(C#CC(C)O)cc12] | $^1$H NMR (400 MHz, DMSO-$d_6$) δ ppm 0.92 (t, J = 7.15 Hz, 3 H) 1.29-1.45 (m, 5 H) 1.51-1.67 (m, 2 H) 3.40-3.51 (m, 2 H) 4.60 (br. s., 1 H) 5.41 (br. s., 1 H) 6.18 (br. s., 2 H) 7.11 (d, J = 8.58 Hz, 1 H) 7.41 (d, J = 8.36 Hz, 1 H) 7.83-7.96 (m, 1 H) 8.14 (br. s., 1 H) | C, 0.74 | See experimental section |
| 15 | 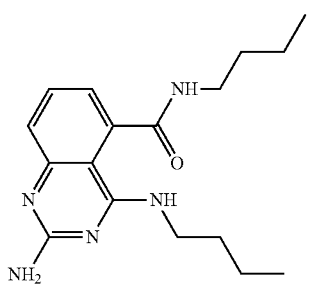 [SMILES: CCCCNC(=O)c1cccc2nc(N)nc(NCCCC)c12] | $^1$H NMR (400 MHz, DMSO-$d_6$) δ ppm 0.92 (m, J = 7.3, 7.3, 2.3 Hz, 6 H), 1.29-1.45 (m, 4 H), 1.47-1.60 (m, 4 H), 3.24-3.30 (m, 2 H), 3.39 (td, J = 6.8, 5.0 Hz, 2 H), 6.10 (s, 2 H), 6.96 (dd, J = 7.0, 1.3 Hz, 1 H), 7.29 (dd, J = 8.4, 1.4 Hz, 1 H), 7.46 (t, J = 8.4 Hz, 1 H), 7.95 (t, J = 4.8 Hz, 1 H), 8.88 (t, J = 5.6 Hz, 1 H) | C, 0.97 | See experimental section |
| 16 | 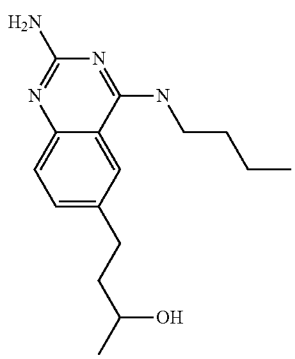 [SMILES: CCCCNc1nc(N)nc2ccc(CCC(C)O)cc12] | $^1$H NMR (400 MHz, DMSO-$d_6$) δ ppm 0.93 (t, J = 7.37 Hz, 3 H) 1.10 (d, J = 6.16 Hz, 3 H) 1.30-1.42 (m, 2 H) 1.56-1.72 (m, 4 H) 2.53-2.75 (m, 2 H) 3.40-3.50 (m, 2 H) 3.57-3.66 (m, 1 H) 4.46 (d, J = 4.62 Hz, 1 H) 5.83 (s, 2 H) 7.10 (d, J = 8.58 Hz, 1 H) 7.31 (dd, J = 8.58, 1.76 Hz, 1 H) 7.65 (t, J = 5.39 Hz, 1 H) 7.76-7.84 (m, 1 H) | C, 0.75 | See experimental section |
| 17 | 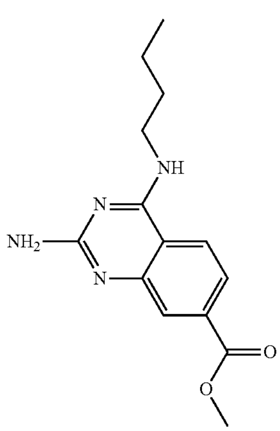 [SMILES: CCCCNc1nc(N)nc2cc(C(=O)OC)ccc12] | $^1$H NMR (400 MHz, DMSO-$d_6$) δ ppm 0.94 (t, J = 7.4 Hz, 3 H), 1.37 (dq, J = 14.9, 7.4 Hz, 2 H), 1.66 (quin, J = 7.3 Hz, 2 H), 3.52-3.63 (m, 2 H), 3.71 (br. s, 2 H), 3.93 (s, 3 H), 7.88 (dd, J = 8.5, 1.5 Hz, 1 H), 8.01 (d, J = 1.5 Hz, 1 H), 8.46 (d, J = 8.5 Hz, 1 H), 9.67 (t, J = 5.4 Hz, 1 H), 12.84 (s, 1 H) (HCl salt) | C, 0.78 | Same method as to prepare 9 from V-25 |

TABLE 1-continued

Compounds of formula (I).

| # | STRUCTURE | H NMR | Method, Rt | Synthetic Method |
|---|---|---|---|---|
| 18 | 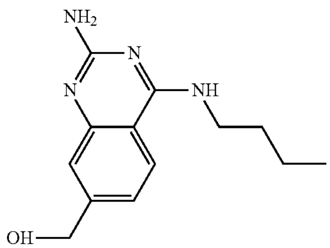 [SMILES: CCCCNc1nc(N)nc2cc(CO)ccc12] | $^1$H NMR (400 MHz, DMSO-$d_6$) δ ppm 0.92 (t, J = 7.3 Hz, 3 H), 1.36 (dq, J = 14.9, 7.4 Hz, 2 H) 1.60 (quin, J = 7.3 Hz, 2 H), 3.41-3.49 (m, 2 H), 4.53 (s, 2 H), 65.24 (br. s., 1 H), 5.98 (s, 2 H), 6.96 (dd, J = 8.3, 1.5 Hz, 1 H), 7.13 (s, 1 H), 7.69 (t, J = 5.4 Hz, 1 H), 7.92 (d, J = 8.5 Hz, 1 H) | C, 0.58 | See experimental section |
| 19 | 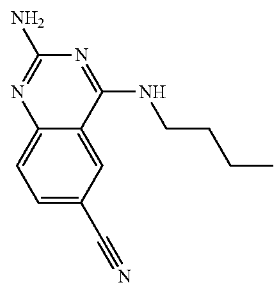 [SMILES: CCCCNc1nc(N)nc2ccc(C#N)cc12] | $^1$H NMR (400 MHz, DMSO-$d_6$) δ ppm 0.93 (t, J = 7.37 Hz, 3 H) 1.31-1.44 (m, 2 H) 1.55-1.65 (m, 2 H) 3.42-3.51 (m, 2 H) 6.57 (br. s., 2 H) 7.20 (d, J = 8.80 Hz, 1 H) 7.71 (dd, J = 8.58, 1.76 Hz, 1 H) 8.02 (br. s., 1 H) 8.55 (d, J = 1.76 Hz, 1 H) | C, 0.83 | See experimental section |
| 20 | 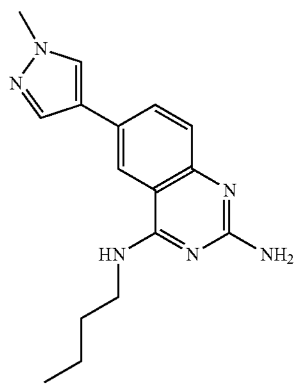 [SMILES: CCCCNc1nc(N)nc2ccc(-c3cnn(C)c3)cc12] | $^1$H NMR (400 MHz, DMSO-$d_6$) δ ppm 0.94 (t, J = 7.40 Hz, 3 H) 1.33-1.45 (m, 2 H) 1.64 (m, J = 7.30, 7.30, 7.30, 7.30 Hz, 2 H) 3.41-3.57 (m, 2 H) 3.88 (s, 3 H) 5.93 (s, 2 H) 7.16 (d, J = 8.78 Hz, 1 H) 7.62-7.74 (m, 2 H) 7.86 (s, 1 H) 8.04 (s, 1 H) 8.18 (d, J = 1.76 Hz, 1H) | B, 4.24 | See experimental section |
| 21 | 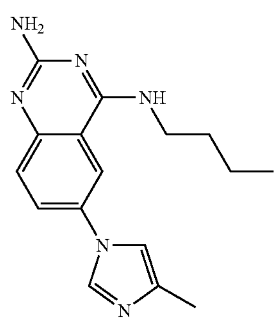 [SMILES: CCCCNc1nc(N)nc2ccc(-n3cnc(C)c3)cc12] | $^1$H NMR (400 MHz, DMSO-$d_6$) δ ppm 0.94 (t, J = 7.4 Hz, 3 H), 1.39 (dq, J = 14.9, 7.4 Hz, 2 H), 1.59-1.67 (m, 2 H), 2.18 (d, J = 0.9 Hz, 3 H), 3.48 (td, J = 7.0, 5.6 Hz, 2 H), 6.11 (s, 2 H), 7.26 (d, J = 8.9 Hz, 1 H), 7.39 (t, J = 1.2 Hz, 1 H), 7.71 (dd, J = 9.0, 2.5 Hz, 1 H), 7.78 (t, J = 5.4 Hz, 1 H), 8.05 (d, J = 1.5 Hz, 1 H), 8.18 (d, J = 2.3 Hz, 1 H) | B, 4.5 | see experimental section |
| 22 | 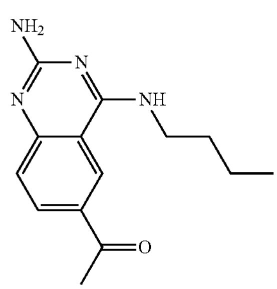 [SMILES: CCCCNc1nc(N)nc2ccc(C(C)=O)cc12] | $^1$H NMR (400 MHz, DMSO-$d_6$) δ ppm 0.94 (t, J = 7.26 Hz, 3 H) 1.26-1.49 (m, 2 H) 1.64 (quin, J = 7.21 Hz, 2 H) 2.58 (s, 3 H) 3.50 (q, J = 6.53 Hz, 2 H) 6.43 (br. s., 2 H) 7.17 (d, J = 8.80 Hz, 1 H) 7.96 (d, J = 8.80 Hz, 1 H) 8.19 (br. s., 1 H) 8.67 (s, 1 H) | C, 0.73 | see experimental section |

TABLE 1-continued

Compounds of formula (I).

| # | STRUCTURE | H NMR | Method, Rt | Synthetic Method |
|---|-----------|-------|------------|------------------|
| 23 | 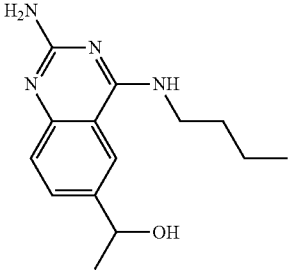 [SMILES: CCCCNc1nc(N)nc2ccc(C(C)O)cc12] | $^1$H NMR (400 MHz, DMSO-d$_6$) δ ppm 0.93 (t, J = 7.37 Hz, 3 H), 1.30-1.42 (m, 5 H) 1.61 (quin, J = 7.32 Hz, 2 H), 3.42-3.50 (m, 2 H) 4.70-4.77 (m, 1 H) 5.07-5.16 (m, 1 H) 5.93 (s, 2 H) 7.15 (d, J = 8.36 Hz, 1 H), 7.48 (dd, J = 8.58, 1.54 Hz, 1 H) 7.79 (t, J = 5.28 Hz, 1 H) 7.91 (d, J = 1.54 Hz, 1 H) | C, 0.66 | see experimental section |
| 24 | 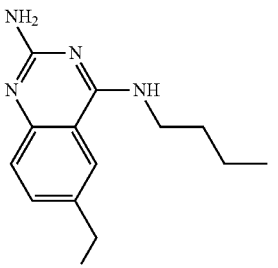 | $^1$H NMR (400 MHz, DMSO-d$_6$) δ ppm 0.92 (t, J = 7.32 Hz, 3 H) 1.25-1.44 (m, 2 H) 1.60 (quin, J = 7.23 Hz, 2 H) 3.38-3.50 (m, 2 H) 4.49 (d, J = 5.12 Hz, 2 H) 5.14 (t, J = 5.49 Hz, 1 H) 5.92 (s, 2 H) 7.14 (d, J = 8.42 Hz, 1 H) 7.43 (d, J = 8.05 Hz, 1 H) 7.74 (t, J = 4.76 Hz, 1 H) 7.90 (s, 1 H) | C, 0.56 | see experimental section |
| 25 | 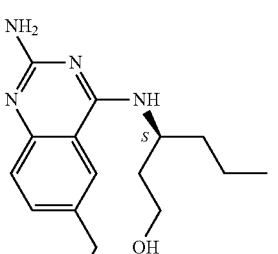 | $^1$H NMR (400 MHz, DMSO-d$_6$) δ ppm 0.89 (t, J = 7.28 Hz, 3 H) 1.17-1.29 (m, 3 H) 1.29-1.39 (m, 2 H) 1.54-1.71 (m, 2 H) 1.76-1.86 (m, 2 H) 2.71 (q, J = 7.61 Hz, 2 H) 3.46 (t, J = 6.65 Hz, 2 H) 4.54-4.63 (m, 1 H) 7.36-7.40 (m, 1 H) 7.66 (dd, J = 8.41, 1.63 Hz, 1 H) 7.81 (br. s., 2 H) 8.21 (s, 1 H) 8.87 (d, J = 8.53 Hz, 1 H) 12.31 (s 1 H) | C, 0.81 | see experimental section |
| 26 | 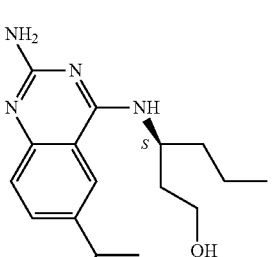 | $^1$H NMR (400 MHz, DMSO-d$_6$) δ ppm 0.90 (t, J = 7.32 Hz, 3 H) 1.27 (d, J = 6.95 Hz, 6 H) 1.29-1.40 (m, 2 H) 1.57-1.74 (m, 2 H) 1.74-1.90 (m, 2 H) 2.93-3.05 (m, 1 H) 3.41-3.53 (m, 2 H) 4.54-4.65 (m, 1 H) 7.38 (d, J = 8.42 Hz, 1 H) 7.70 (dd, J = 8.60, 1.65 Hz, 1 H) 8.27 (s, 1 H) 8.98 (d, J = 8.42 Hz, 1 H) 12.49 (s, 1 H) | C, 0.85 | see experimental section |

TABLE 1-continued

Compounds of formula (I).

| # | STRUCTURE | H NMR | Method, Rt | Synthetic Method |
|---|-----------|-------|------------|------------------|
| 27 | 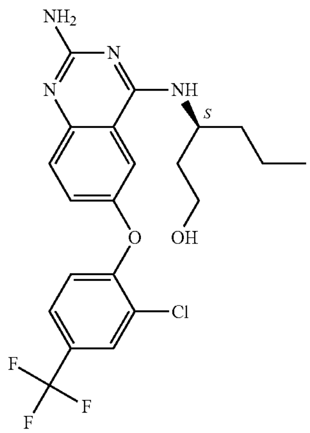 | $^1$H NMR (400 MHz, DMSO-d$_6$) δ ppm 0.87 (t, J = 7.4 Hz, 3 H), 1.23-1.38 (m, 2 H), 1.49-1.62 (m, 2 H), 1.63-1.79 (m, 2 H), 3.44 (t, J = 6.4 Hz, 2 H), 4.33-64.42 (m, 1 H), 4.42-4.52 (m, 1 H), 6.43 (br. s., 2 H), 6.99 (d, J = 8.8 Hz, 1 H), 7.34 (d, J = 9.0 Hz, 1 H), 7.41 (dd, J = 9.0, 2.5 Hz, 1 H), 7.58-7.68 (m, 2 H), 8.02 (d, J = 2.0 Hz, 1 H), 8.06 (d, J = 2.5 Hz, 1 H) | C, 1.1 | see experimental section |
| 28 | 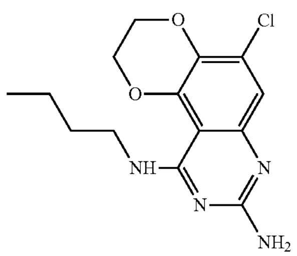 [SMILES: CCCCNc1nc(N)nc2cc(Cl)c3c(c12)OCCO3] | $^1$H NMR (400 MHz, d-DMF) δ ppm 1.36 (t, J = 7.4 Hz, 3 H), 1.79 (dq, J = 14.9, 7.4 Hz, 2 H), 1.97-2.07 (m, 2 H), 3.88 (td, J = 7.0, 5.8 Hz, 2 H), 4.74-4.80 (m, 2 H), 4.86-4.92 (m, 2 H), 6.38 (s, 2 H), 7.25 (s, 1 H), 8.07 (t, J = 5.5 Hz, 1 H) | C, 0.85 | see experimental section |
| 29 | 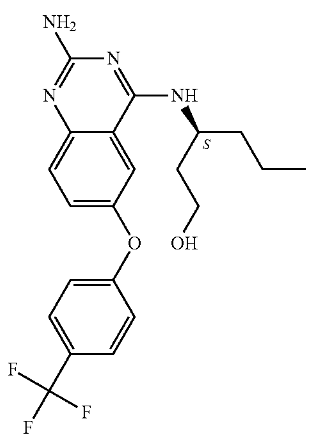 | $^1$H NMR (400 MHz, DMSO-d$_6$) δ ppm 0.87 (t, J = 7.4 Hz, 3 H), 1.22-1.39 (m, 2 H), 1.46-1.61 (m, 2 H), 1.61-1.79 (m, 2 H), 3.43 (t, J = 6.5 Hz, 2 H), 2.48-64.50 (m, 2 H), 6.07 (s, 2 H), 7.10 (d, J = 8.8 Hz, 2 H), 7.24-7.40 (m, 3 H), 7.71 (d, J = 8.5 Hz, 2 H), 7.98 (d, J = 2.3 Hz, 1 H) | C, 1.05 | see experimental section |
| 30 | 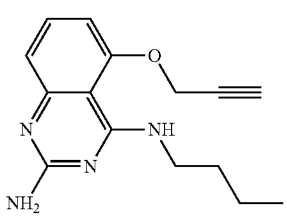 [SMILES: C#CCOc1cccc2nc(N)nc(NCCCC)c12] | $^1$H NMR (400 MHz, DMSO-d$_6$) δ ppm 0.94 (t, J = 7.28 Hz, 3 H) 1.35-1.45 (m, 2 H) 1.56-1.65 (m, 2 H) 3.44-3.53 (m, 2 H) 3.73 (t, J = 2.38 Hz, 1 H) 5.01 (d, J = 2.26 Hz, 2 H) 6.38 (br. s., 2 H) 6.69 (d, J = 8.03 Hz, 1 H) 6.86 (d, J = 7.78 Hz, 1 H) 7.42 (t, J = 8.28 Hz, 1 H) 8.04 (br. s., 1 H) | C, 0.84 | Same method as to prepare 11 |

TABLE 1-continued

Compounds of formula (I).

| # | STRUCTURE | H NMR | Method, Rt | Synthetic Method |
|---|---|---|---|---|
| 31 | 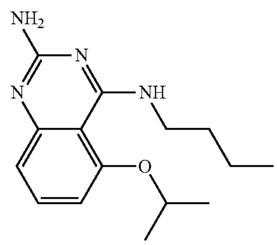 [SMILES: CCCCNc1nc(N)nc2cccc(OC(C)C)c12] | $^1$H NMR (400 MHz, DMSO-$d_6$) δ ppm 0.94 (t, J = 7.40 Hz, 3 H) 1.38 (d, J = 6.02 Hz, 6 H) 1.40-1.47 (m, 2 H) 1.56-1.64 (m, 2 H) 3.43-3.49 (m, 2 H) 4.79-4.85 (m, 1 H) 6.08 (br. s., 2 H) 6.61 (d, J = 8.03 Hz, 1 H) 6.76 (dd, J = 8.28, 0.75 Hz, 1 H) 7.35 (t, J = 8.16 Hz, 1 H) 7.97 (br. s., 1 H) | C, 0.96 | Same method as to prepare 11 |
| 32 | 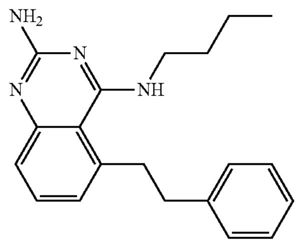 [SMILES: CCCCNc1nc(N)nc2cccc(CCc3ccccc3)c12] | $^1$H NMR (400 MHz, DMSO-$d_6$) δ ppm 0.89 (t, J = 7.40 Hz, 3 H) 1.36 (dq, J = 14.90, 7.41 Hz, 2 H) 1.56-1.66 (m, 2 H) 2.82-2.93 (m, 2 H) 3.34-3.43 (m, 2 H) 3.43-3.52 (m, 2 H) 5.95 (s, 2 H) 6.60 (t, J = 5.14 Hz, 1 H) 6.83-6.89 (m, 1 H) 7.07 (dd, J = 8.28, 1.25 Hz, 1 H) 7.16-7.35 (m, 6 H) | C, 1.1 | Same method as to prepare 12 |
| 33 | 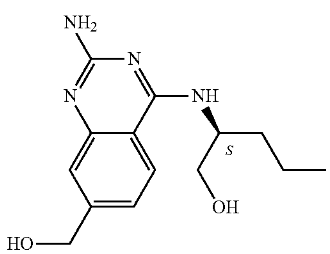 | $^1$H NMR (400 MHz, DMSO-$d_6$) δ ppm 0.89 (t, J = 7.4 Hz, 3 H), 1.21-1.45 (m, 2 H), 1.48-1.71 (m, 2 H), 3.49 (qd, J = 10.4, 5.8 Hz, 2 H), 4.31-4.43 (m, 1 H), 64.54 (s, 2 H), 4.71 (br. s., 1 H), 5.27 (br. s., 1 H), 6.26 (br. s., 2 H), 7.00 (dd, J = 8.4, 1.4 Hz, 1 H), 7.16 (s, 1 H), 7.40 (d, J = 8.0 Hz, 1 H), 8.03 (d, J = 8.5 Hz, 1 H) OH | C, 0.51 | Same method as to prepare 24 |
| 34 | 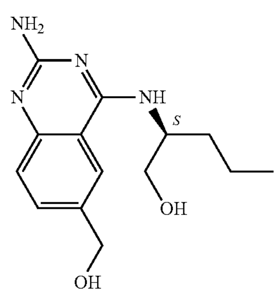 | $^1$H NMR (400 MHz, DMSO-$d_6$) δ ppm 0.89 (t, J = 7.15 Hz, 3 H), 1.34 (td, J = 14.81, 7.78 Hz, 2 H) 1.48-1.74 (m, 2 H) 3.48 (m, J = 11.70, 5.40 Hz, 2 H) 4.38 (m, J = 4.00 Hz, 1 H) 4.50 (d, J = 4.02 Hz, 2 H) 4.68 (t, J = 1.00 Hz, 1 H) 5.12 (t, J = 1.00 Hz, 1 H) 5.87 (br. s., 2 H) 7.15 (d, J = 8.53 Hz, 1 H) 7.26 (d, J = 8.03 Hz, 1 H) 7.44 (dd, J = 8.50 Hz, 1 H) 7.98 (br. s., 1 H) | B, 3.04 | Same method as to prepare 24 |
| 35 | 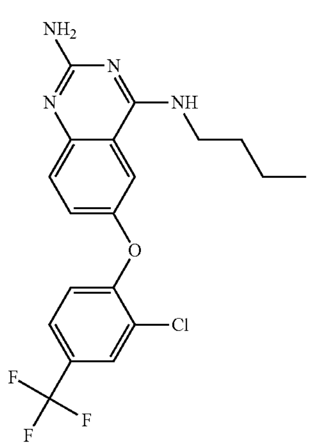 [SMILES: CCCCNc1nc(N)nc2ccc(Oc3ccc(C(F)(F)F)cc3Cl)cc12] | $^1$H NMR (400 MHz, CHLOROFORM-d) δ ppm 0.95 (t, J = 7.4 Hz, 3 H), 1.42 (dq, J = 15.1, 7.4 Hz, 2 H), 1.58-1.70 (m, 2 H), 3.56 (td, J = 7.2, 5.6 Hz, 2 H), 4.96 (s, 2 H), 5.70 (t, J = 4.8 Hz, 1 H), 6.87 (d, J = 8.5 Hz, 1 H), 7.25-7.30 (m, 2 H), 7.38 (dd, J = 8.5, 1.5 Hz, 1 H), 7.43-7.48 (m, 1 H), 7.70 (d, J = 2.0 Hz, 1 H) | C, 1.15 | Same method as to prepare 27 |

TABLE 1-continued

Compounds of formula (I).

| # | STRUCTURE | H NMR | Method, Rt | Synthetic Method |
|---|---|---|---|---|
| 36 | (2-amino-5-methyl-quinazolin-4-yl)-butyl-amine | $^1$H NMR (400 MHz, DMSO-d$_6$) δ ppm 0.94 (t, J = 7.40 Hz, 3 H) 1.30-1.47 (m, 2 H) 1.55-1.70 (m, 2 H), 2.72 (s, 3 H) 3.42-3.53 (m, 2 H) 5.95 (s, 2 H) 6.44-6.60 (m, 1 H) 6.78 (d, J = 7.03 Hz, 1 H) 7.04 (d, J = 7.78 Hz, 1 H) 7.29 (dd, J = 8.28, 7.28 Hz, 1 H) | C, 0.76 | Same method as to prepare 9 |
| 37 | (2-amino-8-fluoro-quinazolin-4-yl)-butyl-amine | $^1$H NMR (400 MHz, DMSO-d$_6$) δ ppm 0.93 (t, J = 7.6 Hz, 3 H), 1.36 (dq, J = 14.9, 7.4 Hz, 2 H), 1.55-1.66 (m, 2 H), 3.42-3.51 (m, 2 H), 6.24 (br. s., 2 H), 66.94 (td, J = 7.9, 5.0 Hz, 1 H), 7.29 (ddd, J = 11.4, 7.8, 1.1 Hz, 1 H), 7.79 (d, J = 8.3 Hz, 1 H), 7.84 (t, J = 5.3 Hz, 1 H) | C, 0.75 | Same method as to prepare 9 |
| 38 | (2-amino-6-fluoro-quinazolin-4-yl)-butyl-amine | $^1$H NMR (400 MHz, DMSO-d$_6$) δ ppm 0.93 (t, J = 7.4 Hz, 3 H), 1.37 (dq, J = 14.9, 7.4 Hz, 2 H), 1.56-1.67 (m, 2 H), 3.43-3.51 (m, 2 H), 6.38 (br. s., 2 H), 67.26 (dd, J = 9.0, 5.3 Hz, 1 H), 7.42 (td, J = 8.8, 3.0 Hz, 1 H), 7.93 (dd, J = 10.2, 2.9 Hz, 1 H), 8.00 (t, J = 5.0 Hz, 1 H) | C, 0.76 | Same method as to prepare 9 |
| 39 | (2-amino-7-methoxy-quinazolin-4-yl)-butyl-amine | $^1$H NMR (400 MHz, DMSO-d$_6$) δ ppm 0.93 (t, J = 7.37 Hz, 3 H) 1.28-1.45 (m, 2 H) 1.50-1.80 (m, 2 H) 3.40-3.53 (m, 2 H) 3.80 (s, 3 H) 6.07 (br. s, 2 H) 6.57-6.70 (m, 1 H) 6.64 (s, 1 H) 7.58 (s, 1 H) 7.81-8.04 (m, 1 H) | C, 0.71 | Same method as to prepare 9 |
| 40 | (2-amino-6-methoxy-quinazolin-4-yl)-butyl-amine | $^1$H NMR (400 MHz, DMSO-d$_6$) δ ppm 0.94 (t, J = 7.3 Hz, 3 H), 1.38 (dq, J = 14.9, 7.4 Hz, 2 H), 1.57-1.69 (m, 2 H), 3.44-3.51 (m, 2 H), 3.56 (s, 3H), 5.87 (s, 2 H), 7.14-67.19 (m, 2 H), 7.50 (s, 1 H), 7.76 (t, J = 5.4 Hz, 1 H) | C, 0.71 | Same method as to prepare 9 |
| 41 | (2-amino-5-chloro-quinazolin-4-yl)-butyl-amine | $^1$H NMR (400 MHz, DMSO-d$_6$) δ ppm 0.93 (t, J = 7.32 Hz, 3 H) 1.29-1.44 (m, 2 H) 1.63 (quin, J = 7.23 Hz, 2 H) 3.47-3.57 (m, 2 H) 6.67 (br. s., 2 H) 7.14 (dd, J = 7.50, 0.91 Hz, 1 H) 7.21 (dd, J = 8.42, 1.10 Hz, 1 H) 7.40-7.51 (m, 1 H) 7.88 (br. s., 1 H) | B, 5.78 | Same method as to prepare 9 |

TABLE 1-continued

Compounds of formula (I).

| # | STRUCTURE | H NMR | Method, Rt | Synthetic Method |
|---|---|---|---|---|
| 42 | 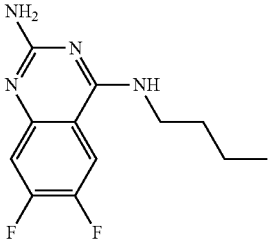 [SMILES: CCCCNc1nc(N)nc2cc(F)c(F)cc12] | $^1$H NMR (400 MHz, DMSO-d$_6$) δ ppm 0.93 (t, J = 7.3 Hz, 2 H), 1.36 (dq, J = 14.9, 7.4 Hz, 2 H), 1.60 (quin, J = 7.3 Hz, 2 H), 3.40-3.48 (m, 2 H), 6.15 (s, 2 H), 67.08 (dd, J = 12.5, 7.8 Hz, 1 H), 7.71 (t, J = 5.3 Hz, 1 H), 8.10 (dd, J = 12.0, 9.0 Hz, 1 H) | C, 0.87 | Same method as to prepare 9 |
| 43 | 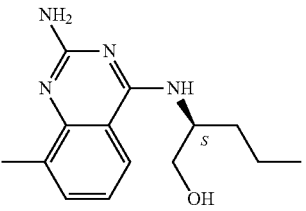 | $^1$H NMR (400 MHz, DMSO-d$_6$) δ ppm 0.78-0.95 (m, 3 H), 1.15-1.42 (m, 2 H), 1.47-1.74 (m, 3 H), 2.37 (s, 3 H), 3.22-3.27 (m, 1 H), 3.42-3.60 (m, 2 H), 4.37 (d, J = 5.3 Hz, 1 H), 4.68 (br. s., 1 H), 6.89 (t, J = 7.5 Hz, 1 H), 7.18 (d, J = 8.3 Hz, 1 H), 7.33 (d, J = 7.0 Hz, 1 H), 7.89 (d, J = 8.0 Hz, 1 H). LC-MS m/z = 261 (M + H) | C, 0.64 | Same method as to prepare 9 |
| 44 | 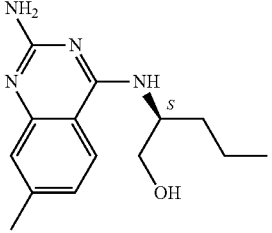 | $^1$H NMR (400 MHz, DMSO-d$_6$) δ ppm 0.89 (t, J = 7.3 Hz, 3 H), 1.20-1.44 (m, 2 H), 1.55 (td, J = 9.1, 4.4 Hz, 1 H), 1.61-1.71 (m, 1 H), 2.33 (s, 3 H), 3.41-3.57 (m, 2 H), 4.24-4.43 (m, 1 H), 4.71 (br. s., 1 H), 5.88 (s, 2 H), 6.84 (dd, J = 8.3, 1.3 Hz, 1 H), 6.98 (s, 1 H), 7.19 (d, J = 8.3 Hz, 1 H), 7.94 (d, J = 8.3 Hz, 1 H) supports structure. LC-MS m/z = 261 (M + H) | C, 0.64 | Same method as to prepare 9 |
| 45 | 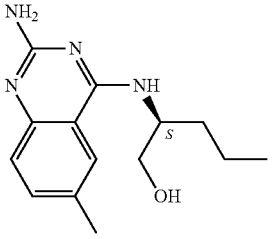 | $^1$H NMR (400 MHz, DMSO-d$_6$) δ ppm 0.80-0.92 (m, 3 H) 1.22-1.43 (m, 2 H) 1.48-1.70 (m, 2 H) 2.34 (s, 3 H) 3.47 (ddt, J = 16.81, 10.98, 5.43, 5.43 Hz, 2 H) 4.30-4.40 (m, 1 H) 4.66 (t, J = 5.40 Hz, 1 H) 5.79 (s, 2 H) 7.09 (d, J = 8.28 Hz, 1 H) 7.15 (d, J = 8.28 Hz, 1 H) 7.30 (dd, J = 8.53, 1.76 Hz, 1 H) 7.86 (s, 1 H) wembrech_1457_2 | C, 0.65 | Same method as to prepare 9 |
| 46 | 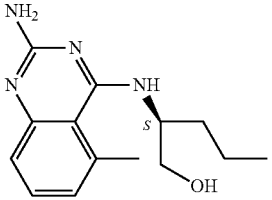 | $^1$H NMR (400 MHz, DMSO-d$_6$) δ ppm 0.85-0.94 (m, 3 H) 1.31-1.45 (m, 2 H) 1.53-1.68 (m, 2 H) 1.90 (s, 3 H) 2.73 (s, 3 H) 3.51-3.56 (m, 2 H) 4.30-4.39 (m, 1 H) 6.00 (s, 2 H) 6.28 (d, J = 8.03 Hz, 1 H) 6.81 (d, J = 7.03 Hz, 1 H) 7.05 (d, J = 8.28 Hz, 1 H) 7.30 (t, J = 8.00 Hz, 1 H) wembrech_1405_2 | C, 0.66 | Same method as to prepare 9 |
| 47 | 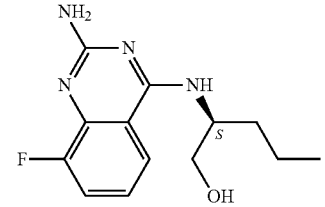 | $^1$H NMR (400 MHz, DMSO-d$_6$) δ ppm 0.89 (t, J = 7.4 Hz, 3 H), 1.20-1.45 (m, 2 H), 1.47-1.72 (m, 2 H), 3.41-3.56 (m, 2 H), 4.31-4.43 (m, 1 H), 4.69 (br. 6 s., 1 H), 6.24 (br. s., 2 H), 6.95 (td, J = 7.9, 5.0 Hz, 1 H), 7.31 (dd, J = 11.3, 7.8 Hz, 1 H), 7.41 (d, J = 8.3 Hz, 1 H), 7.90 (d, J = 8.3 Hz, 1 H) | C, 0.64 | Same method as to prepare 9 |

TABLE 1-continued

Compounds of formula (I).

| # | STRUCTURE | H NMR | Method, Rt | Synthetic Method |
|---|---|---|---|---|
| 48 | (structure with NH$_2$-quinazoline, F substituent, S-configured aminopentanol side chain) | $^1$H NMR (400 MHz, DMSO-d$_6$) δ ppm 0.90 (t, J = 7.3 Hz, 3 H), 1.20-1.45 (m, 2 H), 1.51-1.73 (m, 2 H), 3.54 (br. s., 2 H), 4.45 (td, J = 8.5, 5.5 Hz, 1 H), 4.82 (br. s., 1 H), 7.18 (dd, J = 10.0, 2.5 Hz, 1 H), 7.25 (td, J = 8.8, 2.5 Hz, 1 H), 7.63 (br. s., 2 H), 8.41 (dd, J = 9.0, 5.8 Hz, 1 H), 8.60 (d, J = 8.3 Hz, 1 H) | C, 0.65 | Same method as to prepare 9 |
| 49 | (structure with NH$_2$-quinazoline, F substituent, S-configured aminopentanol side chain) | $^1$H NMR (400 MHz, DMSO-d$_6$) δ ppm 0.90 (t, J = 7.4 Hz, 3 H), 1.22-1.45 (m, 2 H), 1.49-1.72 (m, 2 H), 3.43-3.55 (m, 2 H), 4.36 (td, J = 8.7, 5.0 Hz, 1 H), 64.69 (br. s., 1 H), 5.98 (s, 2 H), 7.22 (dd, J = 9.0, 5.5 Hz, 1 H), 7.27 (d, J = 8.3 Hz, 1 H), 7.37 (td, J = 8.8, 2.8 Hz, 1 H), 7.98 (dd, J = 10.3, 2.8 Hz, 1 H) | C, 0.63 | Same method as to prepare 9 |
| 50 | (structure with NH$_2$-quinazoline, F substituent, S-configured aminopentanol side chain) | $^1$H NMR (400 MHz, DMSO-d$_6$) δ ppm 0.92 (t, J = 7.4 Hz, 3 H), 1.26-1.42 (m, 2 H), 1.59-1.70 (m, 2 H), 3.53-3.67 (m, 3 H), 4.47 (d, J = 5.3 Hz, 1 H), 7.21-7.36 (m, 2 H), 7.80 (td, J = 8.3, 6.0 Hz, 1 H), 7.93 (dd, J = 14.8, 8.5 Hz, 1 H), 8.38 (br. s., 1 H), 13.06 (br. s., 1 H). LC-MS m/z = 265 (M + H) | C, 0.75 | Same method as to prepare 9 |
| 51 | (structure with NH$_2$-quinazoline, methyl substituent, S-configured aminohexanol side chain) | $^1$H NMR (400 MHz, DMSO-d$_6$) δ ppm 0.79-0.92 (m, 3 H), 1.19-1.39 (m, 4 H) 1.55-1.75 (m, 2 H) 2.41 (s, 3 H) 3.46-3.61 (m, 2 H) 4.40-4.51 (m, 1 H) 7.36 (d, J = 8.53 Hz, 1 H) 7.62 (d, J = 8.28 Hz, 1 H) 7.80 (s, 2 H) 8.29 (s, 1 H) 8.87 (d, J = 8.28 Hz, 1 H) 12.51 (s, 1 H) wembrech_1457_1 | C, 0.73 | Same method as to prepare 9 |
| 52 | (structure with NH$_2$-quinazoline, methyl substituent, S-configured aminohexanol side chain) | $^1$H NMR (400 MHz, DMSO-d$_6$) δ ppm 0.78-0.90 (m, 3 H) 1.20-1.39 (m, 4 H) 1.53-1.70 (m, 2 H) 1.90 (s, 3 H) 2.73 (s, 3 H) 3.50-3.57 (m, 2 H) 4.28-4.36 (m, 1 H) 5.98 (s, 2 H) 6.28 (d, J = 8.28 Hz, 1 H) 6.81 (d, J = 7.03 Hz, 1 H) 7.05 (d, J = 7.78 Hz, 1 H) 7.30 (t, J = 8.30 Hz, 1 H) | C, 0.75 | Same method as to prepare 9 |
| 53 | (structure with NH$_2$-quinazoline, methyl substituent, S-configured aminopentanol side chain) | $^1$H NMR (400 MHz, DMSO-d$_6$) δ ppm 0.89 (t, J = 7.3 Hz, 3 H), 1.23-1.39 (m, 2 H), 1.52-1.71 (m, 2 H), 1.74-1.91 (m, 2 H), 2.43 (s, 3 H), 3.45 (t, J = 6.5 Hz, 2 H), 4.48-4.60 (m, 2 H), 7.18-7.29 (m, 2 H), 7.37-8.21 (m, 2 H), 8.35 (d, J = 8.3 Hz, 1 H), 8.99 (d, J = 8.3 Hz, 1 H), 12.78 (br. s., 1 H) | C, 0.69 | Same method as to prepare 9 |

TABLE 1-continued

Compounds of formula (I).

| # | STRUCTURE | H NMR | Method, Rt | Synthetic Method |
|---|---|---|---|---|
| 54 | 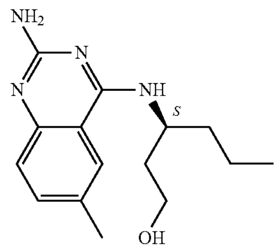 | $^1$H NMR (400 MHz, DMSO-$d_6$) δ ppm 0.00 (s, 1 H) 0.79-0.97 (m, 3 H) 1.19-1.39 (m, 2 H) 1.51-1.74 (m, 2 H) 1.74-1.93 (m, 2 H) 2.40 (s, 3 H) 3.41-3.52 (m, 2 H) 4.51-4.63 (m, 1 H) 7.35 (d, J = 8.53 Hz, 1 H) 7.57-7.65 (m, 1 H) 7.83 (s, 2 H) 8.25 (s, 1 H) 8.91 (d, J = 8.28 Hz, 1 H) 12.57 (s, 1 H) wembrech_1457_4 | C, 0.72 | Same method as to prepare 9 |
| 55 | 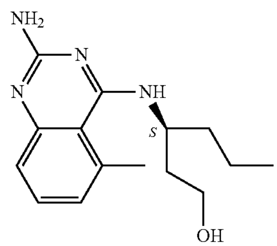 | $^1$H NMR (400 MHz, DMSO-$d_6$) δ ppm 0.85-0.95 (m, 3 H) 1.29-1.42 (m, 2 H) 1.53-1.78 (m, 2 H) 1.79-1.86 (m, 2 H) 2.78 (s, 3 H) 3.50-3.66 (m, 2 H) 4.57-4.70 (m, 1 H) 7.21 (d, J = 7.28 Hz, 1 H) 7.29 (d, J = 8.03 Hz, 1 H) 7.62 (t, J = 7.91 Hz, 1 H) 7.75 (d, J = 8.03 Hz, 2 H) 7.87 (d, J = 8.03 Hz, 1 H) 12.36 (s, 1 H) | C, 0.75 | Same method as to prepare 9 |
| 56 | 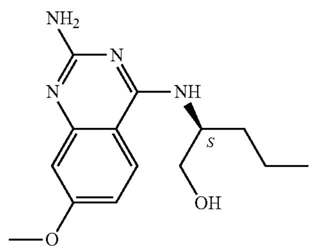 | $^1$H NMR (400 MHz, DMSO-$d_6$) δ ppm 0.88 (t, J = 7.3 Hz, 3 H), 1.18-1.43 (m, 2 H), 1.54 (td, J = 9.1, 4.4 Hz, 1 H), 1.60-1.71 (m, 1 H), 3.39-3.54 (m, 2 H), 3.79 (s, 3 H), 4.33 (td, J = 8.6, 5.1 Hz, 1 H), 4.66 (t, J = 5.4 Hz, 1 H), 5.87 (s, 2 H), 6.56-6.65 (m, 2 H), 7.11 (d, J = 8.3 Hz, 1 H), 7.95 (d, J = 8.8 Hz, 1 H) | C, 0.63 | Same method as to prepare 9 |
| 57 | 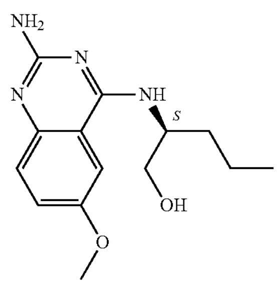 | $^1$H NMR (400 MHz, DMSO-$d_6$) δ ppm 0.90 (t, J = 7.3 Hz, 3 H), 1.25-1.45 (m, 2 H), 1.57 (dtd, J = 13.7, 9.1, 9.1, 5.0 Hz, 1 H), 1.63-1.75 (m, 1 H), 3.44-3.556 (m, 2 H), 3.81 (s, 3 H), 4.39 (td, J = 8.5, 5.3 Hz, 1 H), 4.70 (br. s., 1 H), 5.74 (s, 2 H), 7.11-7.17 (m, 2 H), 7.23 (d, J = 8.3 Hz, 1 H), 7.54 (s, 1 H) | C, 0.64 | Same method as to prepare 9 |
| 58 | 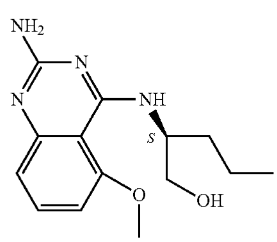 | $^1$H NMR (400 MHz, DMSO-$d_6$) δ ppm 0.92 (t, J = 7.3 Hz, 3 H), 1.29-1.43 (m, 2 H), 1.56-1.71 (m, 2 H), 3.53-3.65 (m, 2 H), 4.04 (s, 3 H), 4.27-4.43 (m, 1 H), 4.66 (br. s., 3 H), 7.02 (d, J = 8.3 Hz, 2 H), 7.71 (t, J = 8.3 Hz, 1 H), 8.90 (d, J = 8.3 Hz, 1 H), 12.85 (s, 1 H) | C, 0.66 | Same method as to prepare 9 |
| 59 | 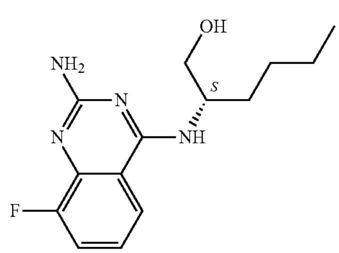 | $^1$H NMR (400 MHz, DMSO-$d_6$) δ ppm 0.85 (t, J = 6.5 Hz, 3 H), 1.19-1.39 (m, 4 H), 1.48-1.62 (m, 1 H), 1.62-1.77 (m, 1 H), 3.40-3.56 (m, 2 H), 4.35 (td, 6 J = 8.7, 5.0 Hz, 1 H), 4.69 (t, J = 5.4 Hz, 1 H), 6.24 (br. s, 2 H), 6.95 (td, J = 8.0, 5.0 Hz, 1 H), 7.31 (dd, J = 11.2, 7.7 Hz, 1 H), 7.41 (d, J = 8.3 Hz, 1 H), 7.90 (d, J = 8.3 Hz, 1 H) | C, 0.74 | Same method as to prepare 9 |

TABLE 1-continued

Compounds of formula (I).

| # | STRUCTURE | H NMR | Method, Rt | Synthetic Method |
|---|-----------|-------|------------|------------------|
| 60 | 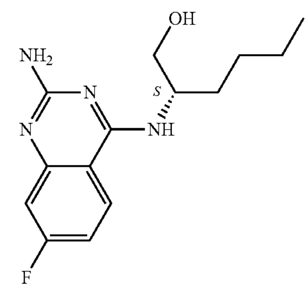 | $^1$H NMR (400 MHz, DMSO-d$_6$) δ ppm 0.86 (t, J = 6.7 Hz, 3 H), 1.20-1.39 (m, 4 H), 1.54-1.76 (m, 2 H), 3.55 (d, J = 5.8 Hz, 4 H), 4.37-4.50 (m, 1 H), 7.26 (dd, J = 9.8, 2.5 Hz, 1 H), 7.30-7.36 (m, 1 H), 8.50-8.57 (m, 1 H), 8.99 (d, J = 8.0 Hz, 1 H), 12.48 (br. s., 1 H) | C, 0.77 | Same method as to prepare 9 |
| 61 | 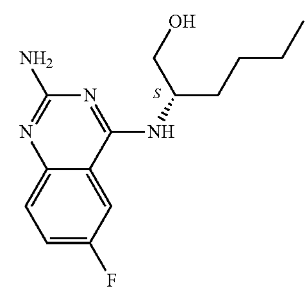 | $^1$H NMR (400 MHz, DMSO-d$_6$) δ ppm 0.86 (t, J = 6.5 Hz, 3 H), 1.17-1.40 (m, 4 H), 1.47-1.62 (m, 1 H), 1.62-1.76 (m, 1 H), 3.42-3.55 (m, 2 H), 4.25-64.42 (m, 1 H), 4.69 (br. s., 1 H), 6.13 (br. s., 2 H), 7.23 (dd, J = 9.2, 5.4 Hz, 1 H), 7.39 (br. s, 1 H), 7.39 (td, J = 8.6, 2.4 Hz, 1 H), 8.00 (dd, J = 10.3, 2.8 Hz, 1 H) | C, 0.73 | Same method as to prepare 9 |
| 62 | 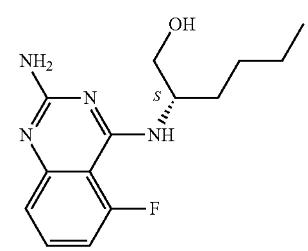 | $^1$H NMR (400 MHz, DMSO-d$_6$) δ ppm 0.82-0.92 (m, 3 H), 1.25-1.40 (m, 4 H), 1.53-1.73 (m, 2 H), 3.51-3.60 (m, 2 H), 4.37 (m, J = 3.5 Hz, 1 H), 4.92 (br. s, 1 H), 6.74 (br. s., 2 H), 6.92 (dd, J = 12.8, 8.0 Hz, 1 H), 7.01-7.08 (m, 1 H), 7.08-7.12 (m, 1 H), 7.54 (td, J = 8.2, 6.5 Hz, 1 H). LC-MS m/z = 279 (M + H). | C, 0.83 | Same method as to prepare 9 |
| 63 | 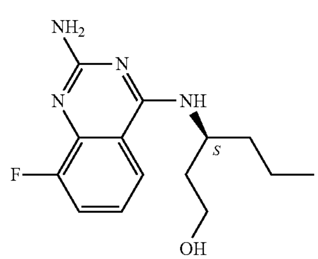 | $^1$H NMR (400 MHz, DMSO-d$_6$) δ ppm 0.88 (t, J = 7.4 Hz, 3 H), 1.22-1.40 (m, 2 H), 1.47-1.66 (m, 2 H), 1.66-1.80 (m, 2 H), 3.41-3.49 (m, 2 H), 4.33-64.52 (m, 2 H), 6.26 (br. s., 2 H), 6.95 (td, J = 8.0, 4.9 Hz, 1 H), 7.31 (dd, J = 11.3, 7.8 Hz, 1 H), 7.48 (d, J = 8.5 Hz, 1 H), 7.87 (d, J = 8.3 Hz, 1 H) | C, 0.69 | Same method as to prepare 9 |
| 64 | 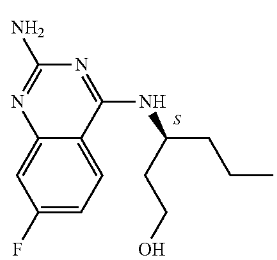 | $^1$H NMR (400 MHz, DMSO-d$_6$) δ ppm 0.88 (t, J = 7.4 Hz, 3 H), 1.21-1.41 (m, 2 H), 1.48-1.66 (m, 2 H), 1.68-1.81 (m, 2 H), 3.42-3.48 (m, 2 H), 4.30-4.55 (m, 2 H), 6.69 (br. s., 2 H), 6.89-7.07 (m, 2 H), 7.86 (d, J = 8.3 Hz, 1 H), 8.21 (dd, J = 8.9, 6.1 Hz, 1 H) | C, 0.73 | Same method as to prepare 9 |

TABLE 1-continued

Compounds of formula (I).

| # | STRUCTURE | H NMR | Method, Rt | Synthetic Method |
|---|---|---|---|---|
| 65 | (structure: 6-fluoro-quinazolin-2-amine with 4-NH-[(S)-1-(2-hydroxyethyl)butyl]) | $^1$H NMR (400 MHz, DMSO-d$_6$) δ ppm 0.88 (t, J = 7.4 Hz, 3 H), 1.25-1.40 (m, 2 H), 1.50-1.65 (m, 2 H), 1.65-1.81 (m, 2 H), 3.45 (t, J = 6.5 Hz, 2 H), 4.32-64.52 (m, 2 H), 6.00 (s, 2 H), 7.22 (dd, J = 9.0, 5.5 Hz, 1 H), 7.28-7.42 (m, 2 H), 7.95 (dd, J = 10.2, 2.9 Hz, 1 H) | C, 0.68 | Same method as to prepare 9 |
| 66 | (structure: 5-fluoro-quinazolin-2-amine with 4-NH-[(S)-1-(2-hydroxyethyl)butyl]) | $^1$H NMR (400 MHz, CHLOROFORM-d) δ ppm 0.95 (t, J = 7.3 Hz, 3 H), 1.34-1.58 (m, 4 H), 1.59-1.72 (m, 2 H), 1.92-2.07 (m, 1 H), 3.55-3.73 (m, 2 H), 4.42-4.59 (m, 1 H), 5.10 (br. s., 2 H), 6.62 (dd, J = 18.7, 8.4 Hz, 1 H), 6.81 (dd, J = 13.1, 8.0 Hz, 1 H), 7.21 (d, J = 8.5 Hz, 1 H), 7.42-7.55 (m, 1 H). LC-MS m/z = 279 (M + H) | C, 0.79 | Same method as to prepare 9 |
| 67 | (structure: 8-fluoro-quinazolin-2-amine with 4-NH-[(2S,3S)-1-hydroxy-3-methylpentan-2-yl]) | $^1$H NMR (400 MHz, DMSO-d$_6$) δ ppm 0.86 (t, J = 7.5 Hz, 3 H), 0.93 (d, J = 6.8 Hz, 3 H), 1.08-1.24 (m, 1 H), 1.43-1.59 (m, 1 H), 1.84 (ddt, J = 11.2, 7.7, 4.0, 64.0 Hz, 1 H), 3.54-3.68 (m, 2 H), 4.20-4.30 (m, 1 H), 4.56 (t, J = 5.4 Hz, 1 H), 6.20 (br. s., 2 H), 6.95 (td, J = 8.0, 5.0 Hz, 1 H), 7.30 (ddd, J = 11.4, 7.7, 0.8 Hz, 1 H), 7.39 (d, J = 8.5 Hz, 1 H), 7.95 (d, J = 8.3 Hz, 1 H) | C, 0.72 | Same method as to prepare 9 |
| 68 | (structure: 6-fluoro-quinazolin-2-amine with 4-NH-[(2S,3S)-1-hydroxy-3-methylpentan-2-yl]) | $^1$H NMR (400 MHz, DMSO-d$_6$) δ ppm 0.86 (t, J = 7.4 Hz, 3 H), 0.92 (d, J = 6.8 Hz, 3 H), 1.11-1.24 (m, 1 H), 1.44-1.59 (m, 1 H), 1.83 (ddt, J = 11.3, 7.7, 3.9, 63.9 Hz, 1 H), 3.53-3.69 (m, 2 H), 4.16-4.28 (m, 1 H), 4.55 (br. s., 1 H), 5.94 (s, 2 H), 7.21 (dd, J = 9.2, 5.4 Hz, 1 H), 7.28 (d, J = 8.3 Hz, 1 H), 7.37 (td, J = 8.8, 2.8 Hz, 1 H), 8.04 (dd, J = 10.3, 2.8 Hz, 1 H) F 6 | C, 0.71 | Same method as to prepare 9 |
| 69 | (structure: 8-chloro-quinazolin-2-amine with 4-NH-[(S)-1-(2-hydroxyethyl)butyl]) | $^1$H NMR (400 MHz, DMSO-d$_6$) δ ppm 0.88 (t, J = 7.28 Hz, 3 H) 1.20-1.43 (m, 2 H) 1.49-1.70 (m, 2 H) 3.40-3.54 (m, 2 H) 4.30-4.42 (m, 1 H) 4.68 (t, J = 5.02 Hz, 1 H) 6.25 (br. s., 2 H) 6.96 (t, J = 7.91 Hz, 1 H) 7.41 (d, J = 8.28 Hz, 1 H) 7.62 (d, J = 7.53 Hz, 1 H) 8.04 (d, J = 8.28 Hz, 1 H) | C, 0.71 | Same method as to prepare 9 |
| 70 | (structure: 7-chloro-quinazolin-2-amine with 4-NH-[(S)-1-(2-hydroxyethyl)butyl]) | $^1$H NMR (400 MHz, DMSO-d$_6$) δ ppm 0.80-0.95 (m, 3 H), 1.16-1.43 (m, 2 H), 1.46-1.74 (m, 2 H), 1.91 (t, J = 5.8 Hz, 0 H), 3.43-3.60 (m, 2 H), 3.50-3.50 (m, 0 H), 4.35 (td, J = 8.4, 5.3 Hz, 1 H), 4.79 (br. s., 1 H), 6.17 (br. s., 2 H), 7.00 (dd, J = 8.8, 2.0 Hz, 1 H), 7.16 (d, J = 2.0 Hz, 1 H), 7.54 (d, J = 8.0 Hz, 1 H), 8.18 (d, J = 8.8 Hz, 1 H). LC-MS m/z = 281 (M + H) supports structure. LC-MS m/z = 281 (M + H) | C, 0.72 | Same method as to prepare 9 |

TABLE 1-continued

Compounds of formula (I).

| # | STRUCTURE | H NMR | Method, Rt | Synthetic Method |
|---|-----------|-------|------------|------------------|
| 71 | 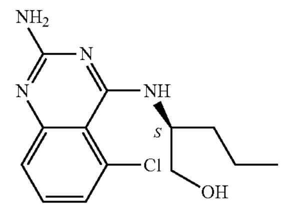 | $^1$H NMR (400 MHz, DMSO-$d_6$) δ ppm 0.91 (t, J = 7.28 Hz, 3 H) 1.23-1.44 (m, 2 H) 1.52-1.68 (m, 2 H) 3.54 (t, J = 4.14 Hz, 2 H) 4.33 (ddt, J = 10.60, 7.22, 3.76, 3.76 Hz, 1 H) 4.90 (t, J = 5.14 Hz, 1 H) 6.22 (br. s., 2 H) 7.05 (dd, J = 7.65, 1.13 Hz, 1 H) 7.15 (dd, J = 8.41, 1.13 Hz, 1 H) 7.33-7.42 (m, 1 H) 7.60 (d, J = 8.03 Hz, 1 H) | B, 4.98 | Same method as to prepare 9 |
| 72 | 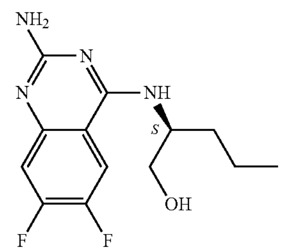 | $^1$H NMR (400 MHz, DMSO-$d_6$) δ ppm 0.89 (t, J = 7.3 Hz, 3 H) 1.22-1.44 (m, 2 H), 1.47-1.59 (m, 1 H), 1.59-1.72 (m, 1 H), 3.41-3.53 (m, 2 H), 4.28-64.40 (m, 1 H), 4.68 (t, J = 5.4 Hz, 1 H), 6.11 (s, 2 H), 7.07 (dd, J = 12.5, 7.8 Hz, 1 H), 7.29 (d, J = 8.3 Hz, 1 H), 8.22 (dd, J = 12.0, 9.0 Hz, 1 H) | C, 0.74 | Same method as to prepare 9 |
| 73 | 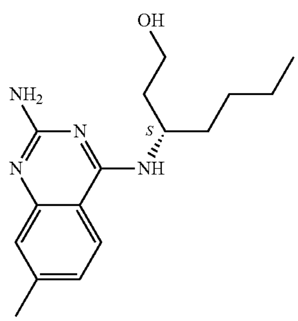 | $^1$H NMR (400 MHz, DMSO-$d_6$) δ ppm 0.85 (t, J = 6.8 Hz, 3 H), 1.19-1.40 (m, 4 H), 1.56-1.72 (m, 2 H), 1.74-1.92 (m, 2 H), 2.44 (s, 3 H), 2.49-2.55 (m, 1 H), 3.46 (t, J = 6.5 Hz, 2 H), 4.47-4.63 (m, 1 H), 7.19-7.28 (m, 2 H), 7.92 (d, J = 8.5 Hz, 2 H), 8.37 (d, J = 8.3 Hz, 1 H), 9.01 (d, J = 8.3 Hz, 1 H), 12.80 (s, 1 H) | C, 0.77 | Same method as to prepare 9 |
| 74 | 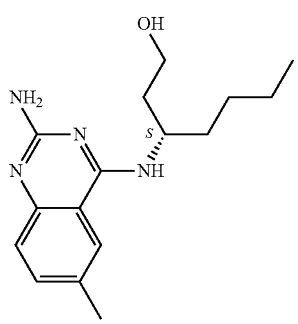 | $^1$H NMR (400 MHz, DMSO-$d_6$) δ ppm 0.82-0.90 (m, 3 H) 1.22-1.37 (m, 4 H) 1.60-1.68 (m, 2 H) 1.75-1.83 (m, 2 H) 2.42 (s, 3 H) 3.43-3.48 (m, 2 H) 4.51-4.59 (m, 1 H) 7.36 (d, J = 8.53 Hz, 1 H) 7.62 (d, J = 8.53 Hz, 1 H) 7.74 (br. s., 2 H) 8.19 (s, 1 H) 8.84 (d, J = 8.28 Hz, 1 H) 12.27 (s, 1 H) wembrech_1457_3 | C, 0.75 | Same method as to prepare 9 |
| 75 | 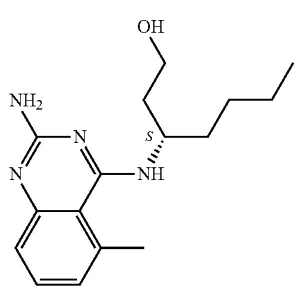 | $^1$H NMR (400 MHz, DMSO-$d_6$) δ ppm 0.82-0.91 (m, 3 H) 1.28-1.40 (m, 4 H) 1.59-1.77 (m, 2 H) 1.83 (q, J = 5.94 Hz, 2 H) 2.78 (s, 3 H) 3.50-3.66 (m, 2 H) 4.55-4.66 (m, 1 H) 7.21 (d, J = 7.53 Hz, 1 H) 7.29 (d, J = 8.28 Hz, 1 H) 7.62 (t, J = 7.91 Hz, 1 H) 7.77 (br. s., 2 H) 7.88 (d, J = 8.03 Hz, 1 H) 12.38 (s, 1 H) | C, 0.83 | Same method as to prepare 9 |

TABLE 1-continued

Compounds of formula (I).

| # | STRUCTURE | H NMR | Method, Rt | Synthetic Method |
|---|---|---|---|---|
| 76 | 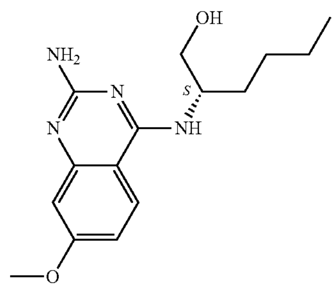 | $^1$H NMR (400 MHz, DMSO-d$_6$) δ ppm 0.85 (t, J = 6.40 Hz, 3 H) 1.17-1.38 (m, 4 H) 1.45-1.58 (m, 1 H) 1.62-1.73 (m, 1 H) 3.37-3.52 (m, 2 H) 3.79 (s, 3 H) 4.30 (dd, J = 8.53, 5.02 Hz, 1 H) 4.60-4.68 (m, 1 H) 5.87 (s, 2 H) 6.59-6.60 (m, 1 H) 6.60-6.65 (m, 1 H) 7.12 (d, J = 8.28 Hz, 1 H) 7.96 (d, J = 8.78 Hz, 1 H) wembrech_1505_1 | C, 0.72 | Same method as to prepare 9 |
| 77 | 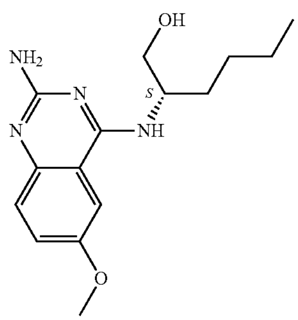 | $^1$H NMR (400 MHz, DMSO-d$_6$) δ ppm 0.86 (t, J = 6.5 Hz, 3 H), 1.22-1.40 (m, 4 H), 1.49-1.63 (m, 1 H), 1.65-1.80 (m, 1 H), 3.44-3.56 (m, 2 H), 3.81 (s, 36 H), 4.37 (td, J = 8.5, 5.3 Hz, 1 H), 4.70 (br. s., 1 H), 5.73 (s, 2 H), 7.12-7.17 (m, 2 H), 7.23 (d, J = 8.3 Hz, 1 H), 7.54 (s, 1 H) | C, 0.73 | Same method as to prepare 9 |
| 78 | 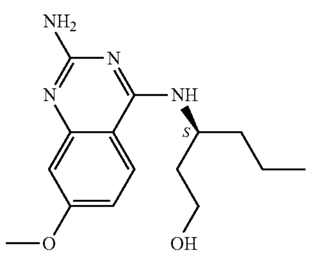 | $^1$H NMR (400 MHz, DMSO-d$_6$) δ ppm 0.87 (t, J = 7.40 Hz, 3 H) 1.22-1.39 (m, 2 H) 1.48-1.78 (m, 4 H) 3.37-3.50 (m, 2 H) 3.78 (s, 3 H) 4.34-4.49 (m, 1 H) 4.34-4.49 (m, 1 H) 5.92 (s, 2 H) 6.60 (d, J = 2.51 Hz, 1 H) 6.61-6.66 (m, 1 H) 7.21 (d, J = 8.53 Hz, 1 H) 7.94 (d, J = 8.78 Hz, 1 H) wembrech_1505_4 | C, 0.67 | Same method as to prepare 9 |
| 79 | 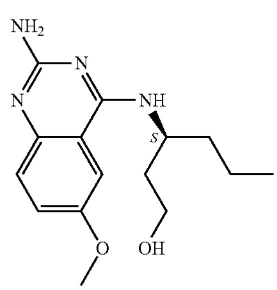 | $^1$H NMR (400 MHz, DMSO-d$_6$) δ ppm 0.89 (t, J = 7.3 Hz, 3 H), 1.26-1.41 (m, 2 H), 1.51-1.66 (m, 2 H), 1.66-1.83 (m, 2 H), 3.42-3.47 (m, 1 H), 3.81 (s, 3 H), 4.38-4.52 (m, 2 H), 5.87 (s, 2 H), 7.14-7.19 (m, 2 H), 7.35 (d, J = 8.5 Hz, 1 H), 7.53 (s, 1 H) | C, 0.67 | Same method as to prepare 9 |
| 80 | 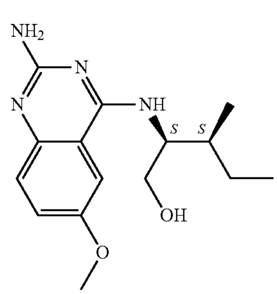 | $^1$H NMR (400 MHz, DMSO-d$_6$) δ ppm 0.86 (t, J = 7.4 Hz, 3 H), 0.94 (d, J = 6.4 Hz, 3 H), 1.11-1.24 (m, 1 H), 1.53 (ddd, J = 13.4, 7.5, 3.9 Hz, 1 H), 1.87 (ddt, 6 J = 11.2, 7.7, 4.0, 4.0 Hz, 1 H), 3.58-3.66 (m, 2 H), 3.82 (s, 3 H), 4.20-4.31 (m, 1 H), 4.58 (br. s., 1 H), 5.69 (s, 2 H), 7.12-7.17 (m, 2 H), 7.24 (d, J = 8.5 Hz, 1 H), 7.59 (s, 1 H) | C, 0.7 | Same method as to prepare 9 |

TABLE 1-continued

Compounds of formula (I).

| # | STRUCTURE | H NMR | Method, Rt | Synthetic Method |
|---|---|---|---|---|
| 81 | (structure: 8-fluoro-2-aminoquinazoline with 4-NH linked to (S)-hexyl chain bearing CH₂CH₂OH) | ¹H NMR (400 MHz, DMSO-d₆) δ ppm 0.84 (t, J = 6.5 Hz, 3 H), 1.20-1.37 (m, 4 H), 1.52-1.65 (m, 2 H), 1.65-1.80 (m, 2 H), 3.44 (q, J = 6.2 Hz, 2 H), 4.35-64.49 (m, 2 H), 6.25 (br. s., 2 H), 6.95 (td, J = 7.9, 5.0 Hz, 1 H), 7.31 (dd, J = 11.3, 7.8 Hz, 1 H), 7.48 (d, J = 8.3 Hz, 1 H), 7.87 (d, J = 8.3 Hz, 1 H) | C, 0.79 | Same method as to prepare 9 |
| 82 | (structure: 7-fluoro-2-aminoquinazoline with 4-NH linked to (S)-hexyl chain bearing CH₂CH₂OH) | ¹H NMR (400 MHz, DMSO-d₆) δ ppm 0.79-0.89 (m, 3 H), 1.19-1.37 (m, 4 H), 1.59 (d, J = 6.5 Hz, 2 H), 1.65-1.79 (m, 2 H), 3.43 (t, J = 6.3 Hz, 2 H), 4.31-4.53 (m, 2 H), 6.24 (s, 2 H), 6.80-6.98 (m, 2 H), 7.51 (d, J = 8.5 Hz, 1 H), 8.14 (dd, J = 8.8, 6.5 Hz, 1 H) | C, 0.81 | Same method as to prepare 9 |
| 83 | (structure: 6-fluoro-2-aminoquinazoline with 4-NH linked to (S)-hexyl chain bearing CH₂CH₂OH) | ¹H NMR (400 MHz, DMSO-d₆) δ ppm 0.85 (t, J = 6.3 Hz, 3 H), 1.20-1.37 (m, 4 H), 1.53-1.64 (m, 2 H), 1.64-1.82 (m, 2 H), 3.45 (t, J = 6.4 Hz, 2 H), 4.34-64.48 (m, 2 H), 6.01 (s, 2 H), 7.22 (dd, J = 9.2, 5.4 Hz, 1 H), 7.29-7.42 (m, 2 H), 7.95 (dd, J = 10.3, 2.8 Hz, 1 H) | C, 0.77 | Same method as to prepare 9 |
| 84 | (structure: 5-fluoro-2-aminoquinazoline with 4-NH linked to (S)-hexyl chain bearing CH₂CH₂OH) | ¹H NMR (400 MHz, CHLOROFORM-d) δ ppm 0.89 (t, J =7.0 Hz, 3 H), 1.19-1.46 (m, 4 H), 1.50-1.79 (m, 4 H), 1.92-2.12 (m, 1 H), 3.59-3.75 (m, 2 H), 3.96 (br. s., 2 H), 4.40-4.56 (m, 1 H), 6.72 (dd, J = 18.6, 8.5 Hz, 1 H), 6.81 (ddd, J = 12.8, 8.0, 0.8 Hz, 1 H), 7.19 (d, J = 8.5 Hz, 1 H), 7.48 (td, J = 8.2, 6.4 Hz, 1 H). LC-MS m/z = 2.93 (M + H) | C, 0.88 | Same method as to prepare 9 |
| 85 | (structure: 6-bromo-2-aminoquinazoline with 4-NH linked to n-butyl) | ¹H NMR (400 MHz, METHANOL-d₄) δ ppm 0.99 (t, J = 7.3 Hz, 3 H), 1.38-1.50 (m, 2 H), 1.71 (quin, J = 7.4 Hz, 2 H), 3.66 (t, J = 7.3 Hz, 2 H), 7.33 (d, J = 8.8 Hz, 1 H), 7.87 (dd, J = 8.8, 1.8 Hz, 1 H), 8.00 (br. s., 1 H), 8.35 (d, J = 2.0 Hz, 1 H), exchangeable protons not seen | C, 0.9 | Same method as to prepare 9 |

TABLE 1-continued

Compounds of formula (I).

| # | STRUCTURE | H NMR | Method, Rt | Synthetic Method |
|---|---|---|---|---|
| 86 | 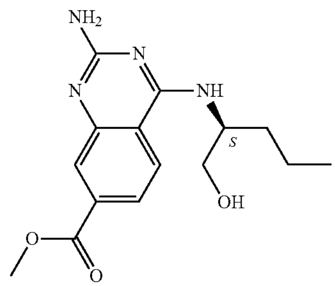 | $^1$H NMR (400 MHz, DMSO-d$_6$) δ ppm 0.89 (t, J = 7.3 Hz, 3 H), 1.24-1.44 (m, 2 H), 1.50-1.73 (m, 2 H), 3.50 (tq, J = 11.1, 5.3 Hz, 2 H), 3.88 (s, 3 H), 4.386 (td, J = 8.6, 5.1 Hz, 1 H), 4.69 (t, J = 5.1 Hz, 1 H), 6.17 (br. s., 2 H), 7.50 (dd, J = 8.5, 1.8 Hz, 2 H), 7.74 (d, J = 1.8 Hz, 1 H), 8.19 (d, J = 8.5 Hz, 1 H) | C, 0.68 | Same method as to prepare 9 |
| 87 | 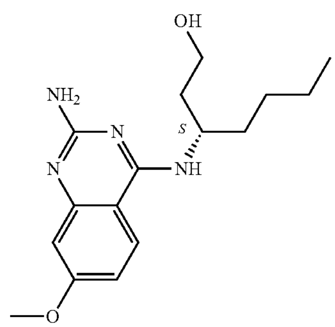 | $^1$H NMR (400 MHz, DMSO-d$_6$) δ ppm 0.76-0.89 (m, 3 H) 1.28 (d, J = 5.02 Hz, 4 H) 1.48-1.78 (m, 4 H) 3.36-3.48 (m, 2 H) 3.69-3.84 (m, 3 H) 4.32-4.46 (m, 1 H) 4.32-4.46 (m, 1 H) 5.90 (s, 2 H) 6.60 (d, J = 2.51 Hz, 1 H) 6.63 (s, 1 H) 7.20 (d, J = 8.53 Hz, 1 H) 7.94 (d, J = 9.03 Hz, 1 H) | C, 0.74 | Same method as to prepare 9 |
| 88 | 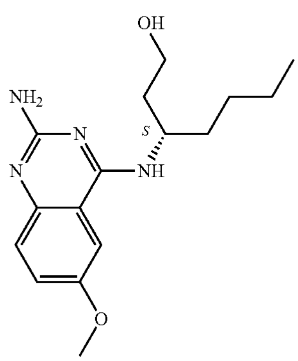 | $^1$H NMR (400 MHz, DMSO-d$_6$) δ ppm 0.85 (t, J = 6.7 Hz, 2 H), 1.22-1.36 (m, 4 H), 1.56-1.65 (m, 2 H), 1.65-1.84 (m, 2 H), 3.40-3.50 (m, 2 H), 3.81 (s, 36 H), 4.38-4.49 (m, 2 H), 5.74 (s, 2 H), 7.15 (s, 2 H), 7.27 (d, J = 8.5 Hz, 1 H), 7.51 (s, 1 H) | C, 0.76 | Same method as to prepare 9 |
| 89 | 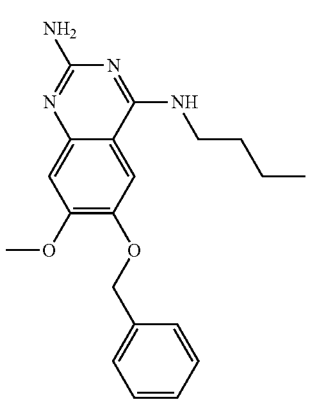 [SMILES: CCCCNc1nc(N)nc2cc(OC)c(OCc3ccccc3)cc12] | $^1$H NMR (400 MHz, DMSO-d$_6$) δ ppm 0.94 (t, J = 7.4 Hz, 3 H), 1.31-1.44 (m, 2 H), 1.55-1.66 (m, 2 H), 3.40-3.50 (m, 2 H), 3.80 (s, 3 H), 5.05 (s, 2 H), 5.67 (s, 2 H), 6.66 (s, 1 H), 7.32-7.46 (m, 4 H), 7.48-7.50 (m, 1 H), 7.51 (m, J = 1.5 Hz, 1 H), 7.59 (s, 1 H) | C, 0.94 | Same method as to prepare 9 |

TABLE 1-continued

Compounds of formula (I).

| # | STRUCTURE | H NMR | Method, Rt | Synthetic Method |
|---|---|---|---|---|
| 90 | 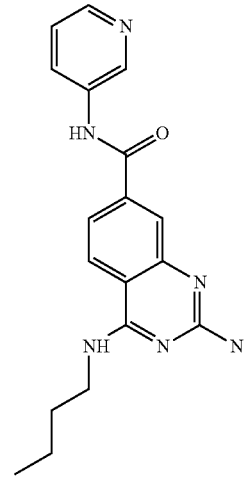 | $^1$H NMR (400 MHz, DMSO-d$_6$) δ ppm 0.94 (t, J = 7.4 Hz, 3 H), 1.38 (dq, J = 15.0, 7.3 Hz, 2 H), 1.63 (quin, J = 7.4 Hz, 2 H), 3.43-3.54 (m, 2 H), 6.19 (s, 2 H), 67.37-7.44 (m, 1 H), 7.52 (dd, J = 8.4, 1.8 Hz, 1 H), 7.82 (d, J = 1.5 Hz, 1 H), 7.93 (t, J = 5.4 Hz, 1 H), 8.12 (d, J = 8.6 Hz, 1 H), 8.19-8.25 (m, 1 H), 8.32 (dd, J = 4.7, 1.4 Hz, 1 H), 8.97 (d, J = 2.2 Hz, 1 H), 10.54 (s, 1 H) | C, 0.73 | See experimental |
| 91 | 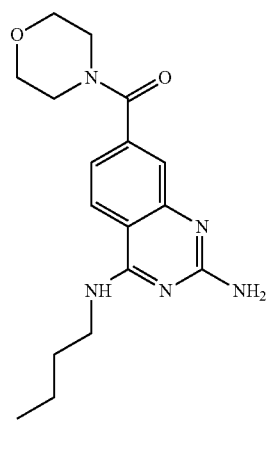 [SMILES: CCCCNc1nc(N)nc2cc(C(=O)N3CCOCC3)ccc12] | $^1$H NMR (400 MHz, DMSO-d$_6$) δ ppm 0.93 (t, J = 7.4 Hz, 3 H), 1.36 (dq, J = 14.9, 7.4 Hz, 2 H), 1.55-1.66 (m, 2 H), 3.43-3.50 (m, 2 H), 3.50-3.74 (m, 4 H), 66.21 (br. s., 2 H), 6.99 (dd, J = 8.3, 1.7 Hz, 1 H), 7.12 (d, J = 1.5 Hz, 1 H), 7.88 (t, J = 5.4 Hz, 1 H), 8.04 (d, J = 8.4 Hz, 1 H) | C, 0.65 | Same as to prepare 90 |
| 92 | 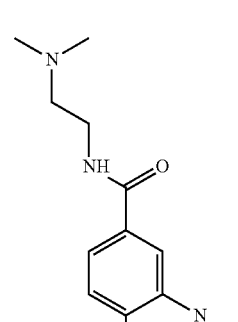 | $^1$H NMR (400 MHz, DMSO-d$_6$) δ ppm 0.93 (t, J = 7.4 Hz, 3 H), 1.37 (dq, J = 15.0, 7.4 Hz, 2 H), 1.62 (quin, J = 7.3 Hz, 2 H), 2.19 (s, 6 H), 2.41 (t, J = 6.8 Hz, 2 H), 3.30-3.42 (m, 2 H), 3.42-3.51 (m, 2 H), 6.13 (s, 2 H), 7.40 (dd, J = 8.4, 1.8 Hz, 1 H), 7.64 (d, J = 1.8 Hz, 1 H), 7.85 (t, J = 5.4 Hz, 1 H), 8.03 (d, J = 8.6 Hz, 1 H), 8.45 (t, J = 5.6 Hz, 1 H) | C, 0.8 | Same as to prepare 90 |

TABLE 1-continued

Compounds of formula (I).

| # | STRUCTURE | H NMR | Method, Rt | Synthetic Method |
|---|---|---|---|---|
| 93 | 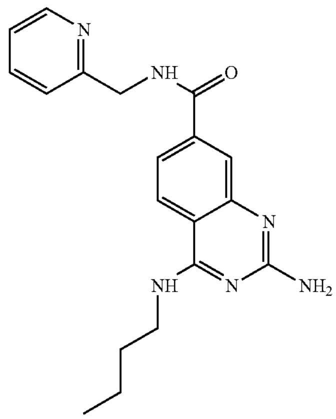 [SMILES: CCCCNc1nc(N)nc2cc(C(=O)NCc3ccccn3)ccc12] | $^1$H NMR (400 MHz, DMSO-$d_6$) δ ppm 0.93 (t, J = 7.4 Hz, 3 H), 1.37 (dq, J = 14.9, 7.4 Hz, 2 H), 1.62 (quin, J = 7.3 Hz, 2 H), 3.44-3.52 (m, 2 H), 4.58 (d, J = 5.96 Hz, 2 H), 6.16 (br. s., 2 H), 7.27 (dd, J = 7.2, 5.0 Hz, 1 H), 7.34 (d, J = 7.9 Hz, 1 H), 7.49 (dd, J = 8.5, 1.7 Hz, 1 H), 7.71-7.80 (m, 2 H), 7.88 (t, J = 5.4 Hz, 1 H), 8.07 (d, J = 8.4 Hz, 1 H), 8.52 (dd, J = 4.8, 0.7 Hz, 1 H), 9.18 (t, J = 5.9 Hz, 1 H) | C, 0.71 | Same as to prepare 90 |
| 94 | 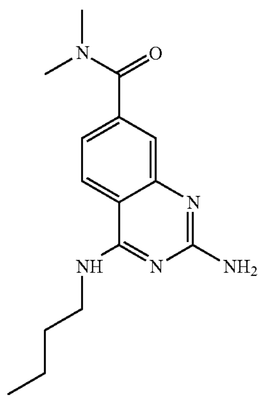 [SMILES: CCCCNc1nc(N)nc2cc(C(=O)N(C)C)ccc12] | $^1$H NMR (400 MHz, DMSO-$d_6$) δ ppm 0.93 (t, J = 7.4 Hz, 3 H), 1.37 (dq, J = 14.9, 7.4 Hz, 2 H), 1.55-1.67 (m, 2 H), 2.90 (s, 3 H), 2.99 (s, 3 H), 3.43-3.52 (m, 2 H), 6.26 (br. s., 2 H), 6.99 (dd, J = 8.3, 1.7 Hz, 1 H), 7.12 (d, J = 1.5 Hz, 1 H), 7.93 (t, J = 5.2 Hz, 1 H), 8.04 (d, J = 8.4 Hz, 1 H) | C, 0.65 | Same as to prepare 90 |
| 95 | 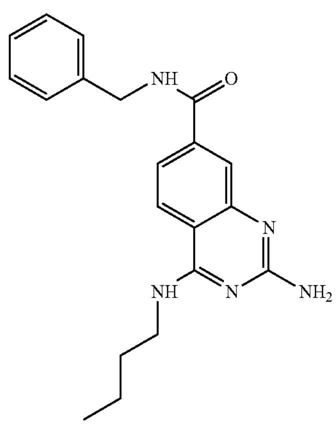 [SMILES: CCCCNc1nc(N)nc2cc(C(=O)NCc3ccccc3)ccc12] | $^1$H NMR (400 MHz, DMSO-$d_6$) δ ppm 0.93 (t, J = 7.4 Hz, 3 H), 1.31-1.43 (m, 2 H), 1.62 (quin, J = 7.3 Hz, 2 H), 3.43-3.51 (m, 2 H), 4.49 (d, J = 5.9 Hz, 2 H), 66.22 (br. s., 2 H), 7.20-7.29 (m, 1 H), 7.30-7.35 (m, 4 H), 7.48 (dd, J = 8.4, 1.8 Hz, 1 H), 7.72 (d, J = 1.8 Hz, 1 H), 7.93 (t, J = 5.3 Hz, 1 H), 8.07 (d, J = 8.6 Hz, 1 H), 9.13 (t, J = 5.9 Hz, 1 H) | C, 0.87 | Same as to prepare 90 |
| 96 | 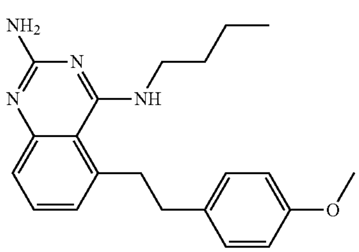 [SMILES: CCCCNc1nc(N)nc2cccc(CCc3ccc(OC)cc3)c12] | $^1$H NMR (400 MHz, DMSO-$d_6$) δ ppm 0.90 (t, J = 7.37 Hz, 3 H) 1.31-1.41 (m, 2 H) 1.57-1.65 (m, 2 H) 2.78-2.84 (m, 2 H) 3.36-3.37 (m, 2 H) 3.43-3.51 (m, 2 H) 3.72 (s, 3 H) 6.03 (br. s., 2 H) 6.63 (br. s., 1 H) 6.82-6.88 (m, 3 H) 7.05-7.14 (m, 3 H) 7.30-7.34 (m, 1 H) | C, 1.08 | Same as to prepare 12 |

TABLE 1-continued

Compounds of formula (I).

| # | STRUCTURE | H NMR | Method, Rt | Synthetic Method |
|---|---|---|---|---|
| 97 | (structure: 2-amino-quinazoline with NH-propyl chain and benzyl-methoxyphenyl substituent) | $^1$H NMR (400 MHz, DMSO-$d_6$) δ ppm 0.89 (t, J = 7.37 Hz, 3 H) 1.32-1.39 (m, 2 H) 1.58-1.64 (m, 2 H) 2.82-2.87 (m, 2 H) 3.35-3.41 (m, 2 H) 3.45-3.51 (m, 2 H) 3.72 (s, 3 H) 6.03 (br. s., 2 H) 6.67 (br. s., 1 H) 6.74-6.80 (m, 3 H) 6.89 (d, J = 7.04 Hz, 1 H) 7.08 (d, J = 7.26 Hz, 1 H) 7.19 (t, J = 8.03 Hz, 1 H) 7.33 (t, J = 7.70 Hz, 1 H) | C, 1.06 | Same as to prepare 12 |
| 98 | (structure: 2-amino-quinazoline with NH-propyl chain and O-CH2-C(O)-O-methyl substituent) | $^1$H NMR (400 MHz, DMSO-$d_6$) δ ppm 0.94 (t, J = 7.37 Hz, 3 H) 1.34-1.47 (m, 2 H) 1.60-1.71 (m, 2 H) 3.42-3.56 (m, 2 H) 3.79 (s, 3 H) 4.93 (s, 2 H) 6.03 (s, 2 H) 6.48-6.57 (m, 1 H) 6.81 (dd, J = 8.36, 0.66 Hz, 1 H) 7.33 (t, J = 8.25 Hz, 1 H) 8.25-8.34 (m, 1 H) | C, 0.84 | Same as to prepare 11 |

Analytical Methods.

All compounds were characterized by LC-MS. The following LC-MS methods were used:

Method A.

Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 mL/min. Two mobile phases (10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.7 minutes. An injection volume of 0.75 μl was used. Cone voltage was 30 V for positive ionization mode and 30 V for negative ionization mode.

Method B.

Reversed phase HPLC was carried out on an Xterra MS C18 column (3.5 μm, 4.6×100 mm) with a flow rate of 1.6 mL/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute, 100% B for 1 minute and reequilibrate with 100% A for 1.5 minutes. An injection volume of 10 μl was used.

Method C.

Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 mL/min. Two mobile phases (mobile phase A: 10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.2 minutes. An injection volume of 0.5 μl was used.

Biological Activity of Compounds of Formula (I)
Description of Biological Assays
Assessment of TLR7 and TLR8 Activity The ability of compounds to activate human TLR7 and/or TLR8 was assessed in a cellular reporter assay using HEK293 cells transiently transfected with a TLR7 or TLR8 expression vector and NFκB-luc reporter construct. In one instance the TLR expression construct expresses the respective wild type sequence or a mutant sequence comprising a deletion in the second leucine-rich repeat of the TLR. Such mutant TLR proteins have previously been shown to be more susceptible to agonist activation (U.S. Pat. No. 7,498,409).

Briefly, HEK293 cells were grown in culture medium (DMEM supplemented with 10% FCS and 2 mM Glutamine). For transfection of cells in 10 cm dishes, cells were detached with Trypsin-EDTA, transfected with a mix of CMV-TLR7 or TLR8 plasmid (750 ng), NFκB-luc plasmid (375 ng) and a transfection reagent and incubated 24 hours at 37° C. in a humidified 5% $CO_2$ atmosphere. Transfected cells were then detached with Trypsin-EDTA, washed in PBS and resuspended in medium to a density of $1.67 \times 10^5$ cells/mL. Thirty microliters of cells were then dispensed into each well in 384-well plates, where 10 μL of compound in 4% DMSO was already present. Following 6 hours incubation at 37° C., 5% $CO_2$, the luciferase activity was determined by adding 15 μl of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

Compound toxicity was determined in parallel using a similar dilution series of compound with 30 μL per well of cells transfected with the CMV-TLR7 construct alone ($1.67 \times 10^5$ cells/mL), in 384-well plates. Cell viability was measured after 6 hours incubation at 37° C., 5% $CO_2$ by adding 15 μL of ATP lite (Perkin Elmer) per well and reading on a ViewLux ultraHTS microplate imager (Perkin Elmer). Data was reported as $CC_{50}$.

Suppression of HCV Replicon Replication

Activation of human TLR7 results in robust production of interferon by plasmacytoid dendritic cells present in human blood. The potential of compounds to induce interferon was evaluated by looking at the antiviral activity in the HCV replicon system upon incubation with conditioned media from peripheral blood mononuclear cells (PBMC). The HCV replicon assay is based on a bicistronic expression construct, as described by Lohmann et al. (Science (1999) 285: 110-113; Journal of Virology (2003) 77: 3007-15 3019) with modifications described by Krieger et al. (Journal of Virology (2001) 75: 4614-4624). The assay utilized the stably transfected cell line Huh-7 luc/neo harboring an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter gene (Firefly-luciferase) and a selectable marker gene (neoR, neomycine phosphotransferase). The construct is flanked by 5' and 3' NTRs (non-translated regions) from HCV type 1b. Continued culture of the replicon cells in the presence of G418 (neoR) is dependent on the replication of the HCV RNA. The stably transfected replicon cells that replicate HCV RNA autonomously and to high levels, encoding inter alia luciferase, were used for profiling of the conditioned cell culture media.

Briefly, PBMCs were prepared from buffy coats of at least two donors using a standard Ficoll centrifugation protocol. Isolated PBMCs were resuspended in RPMI medium supplemented with 10% human AB serum and $2\times10^5$ cells/well were dispensed into 384-well plates containing compounds (70 µL total volume). After overnight incubation, 10 µL of supernatant was transferred to 384-well plates containing $2.2\times10^3$ replicon cells/well in 30 µL (plated the day before). Following 24 hours of incubation, replication was measured by assaying luciferase activity using 40 µL/well Steady Lite Plus substrate (Perkin Elmer) and measured with ViewLux ultraHTS microplate imager (Perkin Elmer). The inhibitory activity of each compound on the Huh7-luc/neo cells were reported as $EC_{50}$ values, defined as the compound concentration applied to the PBMCs resulting in a 50% reduction of luciferase activity which in turn indicates the degree of replication of the replicon RNA on transfer of a defined amount of PBMC culture medium. Recombinant interferon α-2a (Roferon-A) was used as a standard control compound.

Biological activity of compounds of formula (I). All compounds showed CC50 of >24 µM in the HEK 293 TOX assay described above.

Activation of ISRE Promoter Elements

The potential of compounds to induce IFN-I was also evaluated by measuring the activation of interferon-stimulated responsive elements (ISRE) by conditioned media from PBMC. The ISRE element of sequence GAAACTGAAACT is highly responsive to the STAT1-STAT2-IRF9 transcription factor, activated upon binding of IFN-I to their receptor IFNAR (Clontech, PT3372-5W). The plasmid pISRE-Luc from Clontech (ref. 631913) contains 5 copies of this ISRE element, followed by the firefly luciferase ORF. A HEK293 cell line stably transfected with pISRE-Luc (HEK-ISREluc) was established to profile of the conditioned PBMC cell culture media.

Briefly, PBMCs were prepared from buffy coats of at least two donors using a standard Ficoll centrifugation protocol. Isolated PBMCs were resuspended in RPMI medium supplemented with 10% human AB serum and $2\times10^5$ cells/well were dispensed into 384-well plates containing compounds (70 µL total volume). After overnight incubation, 10 µL of supernatant was transferred to 384-well plates containing $5\times10^3$ HEK-ISREluc cells/well in 30 µL (plated the day before). Following 24 hours of incubation, activation of the ISRE elements was measured by assaying luciferase activity using 40 µL/well Steady Lite Plus substrate (Perkin Elmer) and measured with ViewLux ultraHTS microplate imager (Perkin Elmer). The stimulating activity of each compound on the HEK-ISREluc cells was reported as LEC value, defined as the compound concentration applied to the PBMCs resulting in a luciferase activity at least two fold above the standard deviation of the assay. The LEC in turn indicates the degree of ISRE activation on transfer of a defined amount of PBMC culture medium. Recombinant interferon α-2a (Roferon-A) was used as a standard control compound.

For a given compound, the LEC value obtained from this assay were in the same range as the $EC_{50}$ values obtained from the "suppression of HCV replication assay." Thus, it is possible to compare the potential of compounds to induce IFN-I by PBMC, measured by either of the 2 assays.

| # | STRUCTURE | TLR7-wt_LEC | TLR7-dIRR2_LEC | TLR8-wt_LEC | TLR8-dIRR2_LEC | PBMC-HUH7_EC50 |
|---|-----------|-------------|----------------|-------------|----------------|----------------|
| 1 | 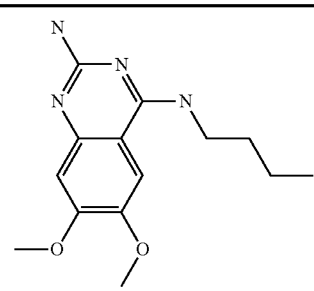 | 5.0 | 0.4 | 1.1 | 0.6 | 1.9 |
| 2 | 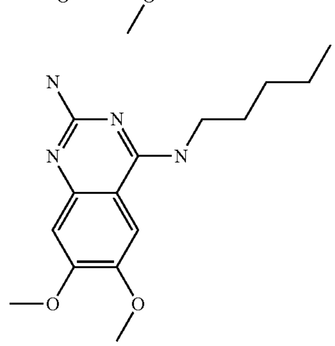 [SMILES: CCCC[C@@H](CCO)Nc1nc(N)nc2cc(OC)c(OC)cc12] | NA | 1.2 | 1.5 | 0.6 | 4.4 |

-continued

| # | Structure | | | | | |
|---|---|---|---|---|---|---|
| 3 | (quinazoline with 6,7-dimethoxy, 2-amino, 4-NH-CH(Bu)-CH2CH2OH) | 4.0 * | 0.9 | 5.5 | 2.4 | 0.6 |
| 4 | (quinazoline with 6,7-dimethoxy, 2-amino, 4-NH-CH(Bu)-CH2OH) | NA | 2.4 | 2.6 | 1.7 | 3.0 |
| 5 | (quinazoline with 6,7-dimethoxy, 2-amino, 4-NH-CH(Pr)-CH2CH2OH) | NA | 2.6 | 6.7 | 2.6 | 3.3 |
| 6 | (quinazoline with 6,7-dimethoxy, 2-amino, 4-NH-CH(Pr)-CH2OH) | NA | 3.4 | 4.4 | 2.3 | 3.0 |
| 7 | (quinazoline with 6,7-dimethoxy, 2-amino, 4-NH-CH(CH(Me)Et)-CH2OH) | NA | 3.8 | 13.8 | 9.0 | 12.4 |

| # | Structure | TLR7-wt (LEC) | TLR8-wt (LEC) | | HEK-ISRE luc (LEC) |
|---|---|---|---|---|---|
| 8 | | 0.1 | 0.02 | 0.1 0.02 | NA |

| # | Structure | TLR7-wt (LEC) | TLR8-wt (LEC) | HEK-ISRE luc (LEC) |
|---|---|---|---|---|
| 9 | 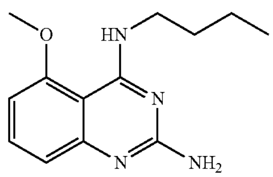 [SMILES: CCCCNc1nc(N)nc2cccc(OC)c12] | 0.41 | 0.13 | 0.10 |
| 10 | 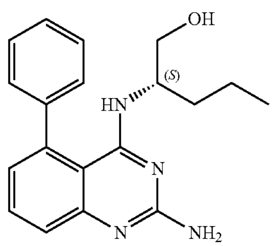 | 6.08 | >25 | 2.14 |
| 11 | 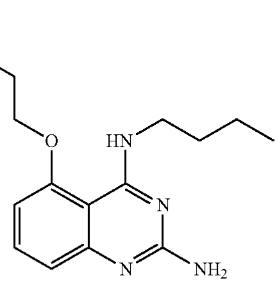 | 0.08 | 0.17 | 0.12 |
| 12 | 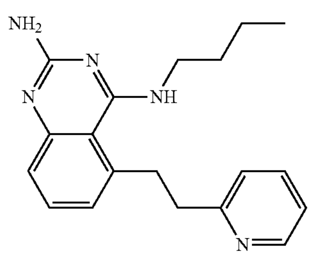 [SMILES: CCCCNc1nc(N)nc2cccc(CCc3ccccn3)c12] | 1.66 | 0.79 | NA |
| 13 | 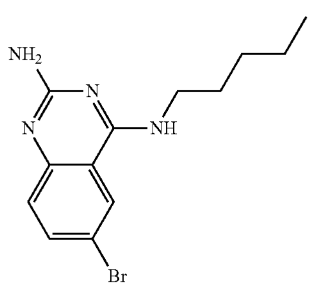 [SMILES: CCCCCNc1nc(N)nc2ccc(Br)cc12] | 0.76 | 0.30 | 0.57 |

-continued
| 14 | 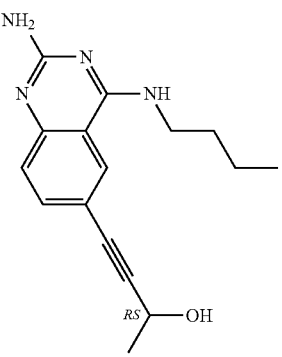 [SMILES: CCCCNc1nc(N)nc2ccc(C#CC(C)O)cc12] | 0.65 | 4.77 | NA |
| 15 | 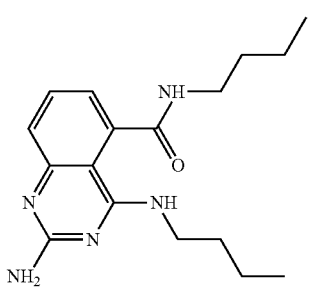 [SMILES: CCCCNC(=O)c1cccc2nc(N)nc(NCCCC)c12] | 0.49 | 3.27 | NA |
| 16 | 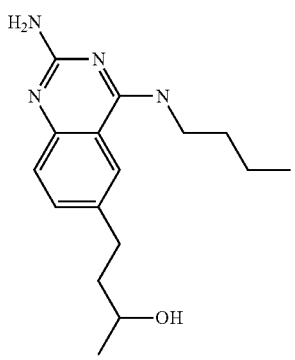 [SMILES: CCCCNc1nc(N)nc2ccc(CCC(C)O)cc12] | 0.57 | 0.73 | NA |
| 17 | 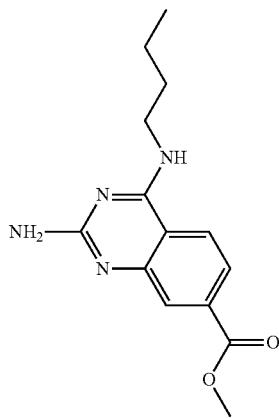 [SMILES: CCCCNc1nc(N)nc2cc(C(=O)OC)ccc12] | 5.10 | 1.66 | 0.75 |

-continued

| | | | | |
|---|---|---|---|---|
| 18 | [2-amino-7-(hydroxymethyl)quinazolin-4-yl]-butylamine structure | 0.13 | 0.13 | 0.05 |
| 19 | 2-amino-4-(butylamino)quinazoline-6-carbonitrile structure | >25 | 7.05 | NA |
| 20 | 2-amino-4-(butylamino)-6-(1-methyl-1H-pyrazol-4-yl)quinazoline structure | >25 | 2.55 | NA |
| 21 | 2-amino-4-(butylamino)-6-(4-methyl-1H-imidazol-1-yl)quinazoline structure | >25 | 2.55 | 12.06 |
| 22 | 1-[2-amino-4-(butylamino)quinazolin-6-yl]ethanone structure | 6.07 | 1.95 | NA |

-continued
| | | | | |
|---|---|---|---|---|
| 23 | 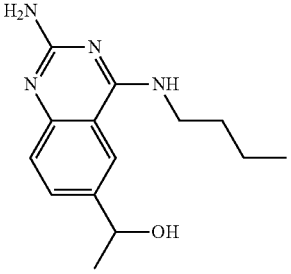 [SMILES: CCCCNc1nc(N)nc2ccc(C(C)O)cc12] | 10.23 | 5.05 | NA |
| 24 | 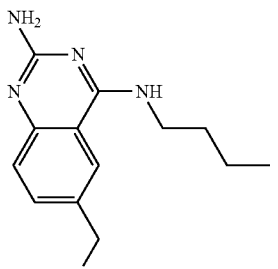 | 0.93 | 0.22 | 0.14 |
| 25 | 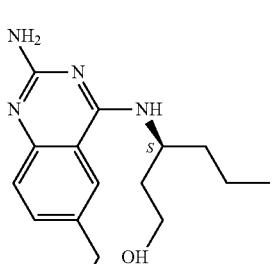 | 0.57 | 0.45 | 0.16 |
| 26 | 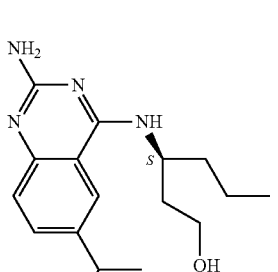 | 3.60 | 1.97 | 3.07 |
| 27 | 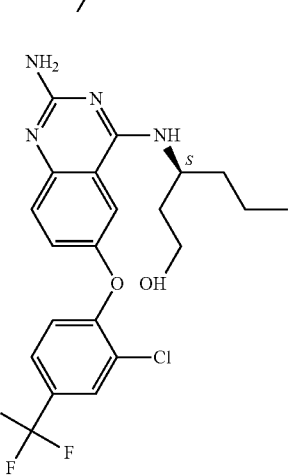 | 12.95 | >25 | 14.21 |

-continued
| | | | | |
|---|---|---|---|---|
| 28 | 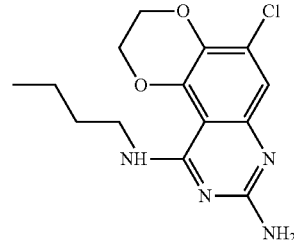 | 2.06 | 0.88 | 1.11 |
| 29 | 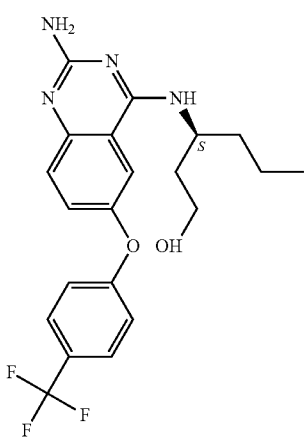 | 11.13 | >25 | >23.81 |
| 30 | 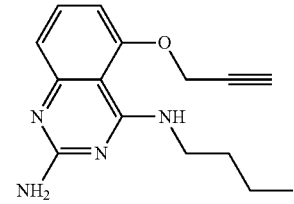 | 0.05 | 0.10 | 0.04 |
| 31 | 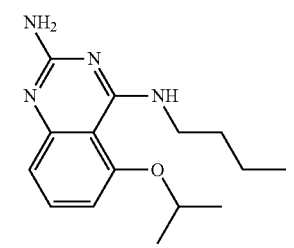 [SMILES: CCCCNc1nc(N)nc2cccc(OC(C)C)c12] | 0.09 | 0.24 | 0.04 |
| 32 | 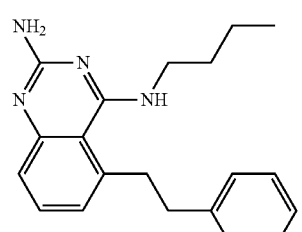 | 0.13 | 0.47 | 0.27 |
| 33 | 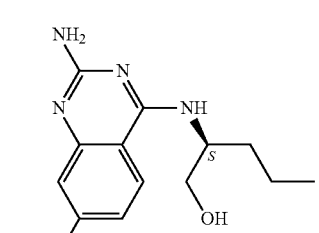 | 1.88 | 0.15 | 0.14 |

-continued

| # | Structure | | | |
|---|---|---|---|---|
| 34 | (2-amino-quinazolin-4-yl)-[(S)-pentyl-1-ol] with 6-CH2OH | 10.77 | 0.27 | 0.39 |
| 35 | 2-amino-4-(butylamino)quinazoline, 6-O-(2-chloro-4-trifluoromethylphenyl) | 4.15 | >25 | >23.81 |
| 36 | 2-amino-4-(butylamino)-5-methylquinazoline | 0.47 | 0.26 | 0.32 |
| 37 | 2-amino-4-(butylamino)-8-fluoroquinazoline | 0.16 | 0.25 | 0.07 |
| 38 | 2-amino-4-(butylamino)-6-fluoroquinazoline | 0.29 | 0.10 | 0.11 |

-continued

| # | Structure | | | |
|---|---|---|---|---|
| 39 | 2-amino-7-methoxy-N-butyl-quinazolin-4-amine | 0.94 | 0.31 | 0.15 |
| 40 | 2-amino-6-methoxy-N-butyl-quinazolin-4-amine | 5.64 | 1.83 | 2.44 |
| 41 | 2-amino-5-chloro-N-butyl-quinazolin-4-amine | 0.99 | 0.13 | 0.17 |
| 42 | 2-amino-6,7-difluoro-N-butyl-quinazolin-4-amine | 1.81 | 0.14 | 0.26 |
| 43 | 2-amino-8-methyl-N-[(S)-1-hydroxymethylpropyl]-quinazolin-4-amine | 4.54 | 0.12 | 0.59 |
| 44 | 2-amino-7-methyl-N-[(S)-1-hydroxymethylpropyl]-quinazolin-4-amine | 0.43 | 0.03 | 0.09 |

| | | | | |
|---|---|---|---|---|
| 45 | 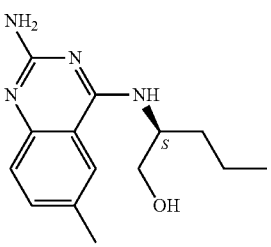 | 0.41 | 0.03 | 0.04 |
| 46 | 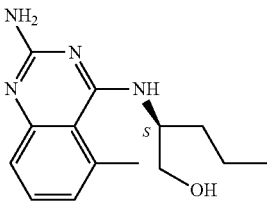 | 0.77 | 0.04 | 0.07 |
| 47 | 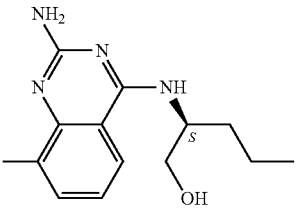 | 0.67 | 0.03 | 0.05 |
| 48 | 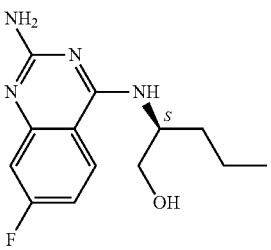 | 0.54 | 0.01 | 0.02 |
| 49 | 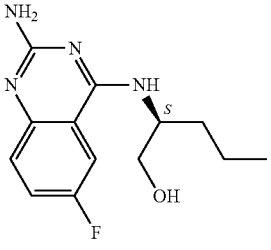 | 2.09 | 0.03 | 0.13 |
| 50 | 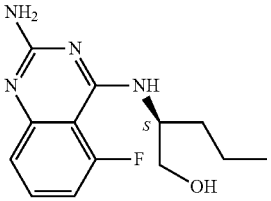 | 0.32 | 0.00 | 0.01 |

-continued

| # | Structure | | | |
|---|---|---|---|---|
| 51 | (2-amino-6-methylquinazolin-4-yl)-NH-[(S)-1-(hydroxymethyl)pentyl] | 0.60 | 0.04 | 0.09 |
| 52 | (2-amino-5-methylquinazolin-4-yl)-NH-[(S)-1-(hydroxymethyl)pentyl] | 0.41 | 0.03 | 0.03 |
| 53 | (2-amino-7-methylquinazolin-4-yl)-NH-[(S)-1-(2-hydroxyethyl)butyl] | 0.06 | 0.05 | 0.02 |
| 54 | (2-amino-6-methylquinazolin-4-yl)-NH-[(S)-1-(2-hydroxyethyl)butyl] | 0.54 | 0.43 | 0.18 |
| 55 | (2-amino-5,6-dimethylquinazolin-4-yl)-NH-[(S)-1-(2-hydroxyethyl)butyl] | 0.22 | 0.14 | 0.06 |
| 56 | (2-amino-7-methoxyquinazolin-4-yl)-NH-[(S)-1-(hydroxymethyl)butyl] | 0.39 | 0.04 | 0.09 |

-continued

| | | | | | |
|---|---|---|---|---|---|
| 57 | [structure] | 10.77 | 0.53 | 2.08 | |
| 58 | [structure] | 0.18 | 0.03 | 0.04 | |
| 59 | [structure] | 0.29 | 0.04 | 0.05 | |
| 60 | [structure] | 0.23 | 0.01 | 0.02 | |
| 61 | [structure] | 0.57 | 0.05 | 0.12 | |
| 62 | [structure] | 0.75 | 0.01 | 0.03 | |

-continued
| | | | | |
|---|---|---|---|---|
| 63 | 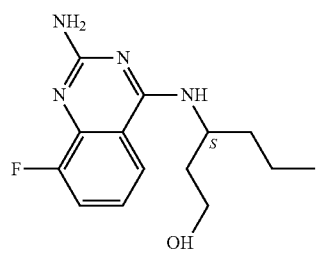 | 0.29 | 0.15 | 0.04 |
| 64 | 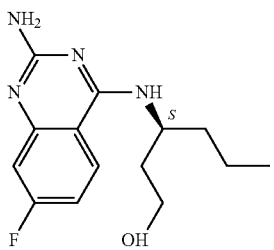 | 0.11 | 0.03 | 0.04 |
| 65 | 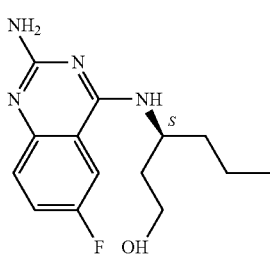 | 0.94 | 0.44 | 0.56 |
| 66 | 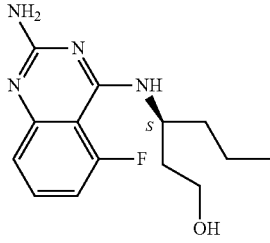 | 0.22 | 0.02 | 0.06 |
| 67 | 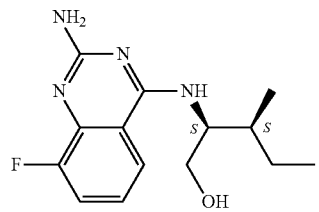 | 2.50 | 0.11 | 0.21 |
| 68 | 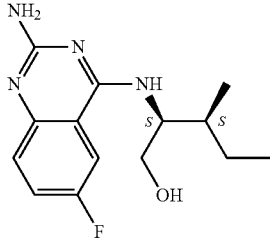 | 4.57 | 0.33 | 0.64 |

-continued

| | | | | |
|---|---|---|---|---|
| 69 | (structure) | 7.48 | 0.38 | 0.73 |
| 70 | (structure) | 0.41 | 0.01 | 0.01 |
| 71 | (structure) | 1.02 | 0.01 | 0.03 |
| 72 | (structure) | 2.59 | 0.02 | 0.05 |
| 73 | (structure) | 0.03 | 0.06 | 0.02 |
| 74 | (structure) | 0.44 | 0.25 | 0.14 |

-continued
| | | | | |
|---|---|---|---|---|
| 75 | 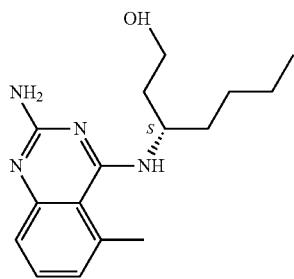 | 0.14 | 0.06 | 0.02 |
| 76 | 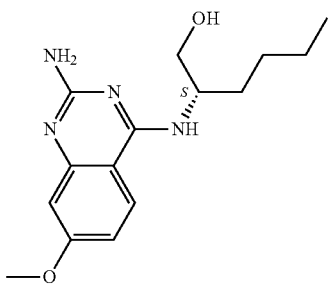 | 0.26 | 0.04 | 0.09 |
| 77 | 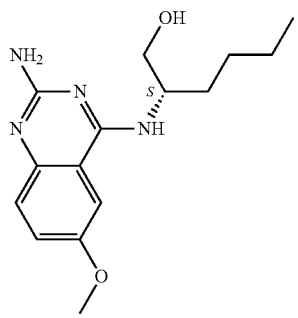 | 3.48 | 0.62 | 1.93 |
| 78 | 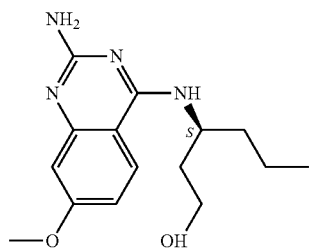 | 0.20 | 0.13 | 0.04 |
| 79 | 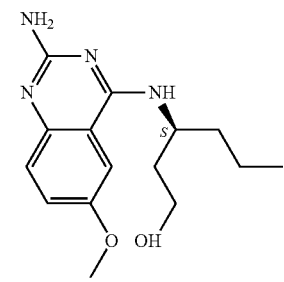 | 11.87 | 2.97 | 2.07 |

-continued
| | | | | |
|---|---|---|---|---|
| 80 | 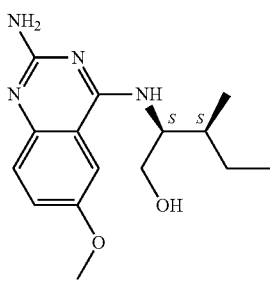 | >25 | 4.10 | >24 |
| 81 | 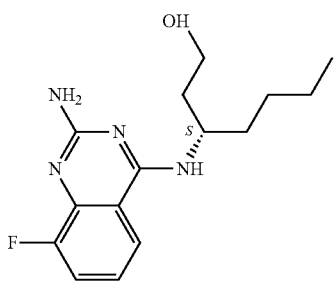 | 0.11 | 0.16 | 0.05 |
| 82 | 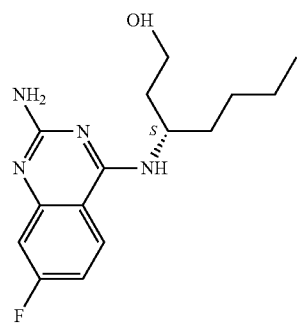 | 0.04 | 0.03 | 0.04 |
| 83 | 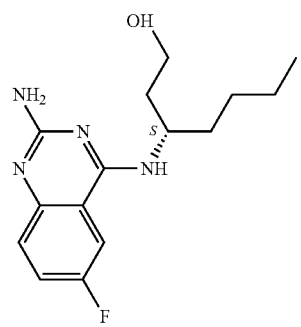 | 1.59 | 0.42 | 0.37 |
| 84 | 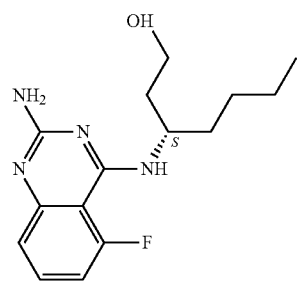 | 0.44 | 0.10 | 0.09 |

-continued

| # | Structure | | | |
|---|---|---|---|---|
| 85 | 2-amino-6-bromo-4-(butylamino)quinazoline | 0.51 | 0.10 | 0.21 |
| 86 | methyl 2-amino-4-[((S)-1-hydroxypentan-2-yl)amino]quinazoline-7-carboxylate | 2.01 | 0.22 | 0.28 |
| 87 | 2-amino-4-[((S)-1-hydroxyheptan-3-yl)amino]-7-methoxyquinazoline | 0.16 | 0.16 | 0.04 |
| 88 | 2-amino-4-[((S)-1-hydroxyheptan-3-yl)amino]-6-methoxyquinazoline | 1.85 | 2.81 | 0.88 |
| 89 | 2-amino-6-benzyloxy-4-(butylamino)-7-methoxyquinazoline | 1.84 | 2.22 | >24 |

-continued
| | | | | |
|---|---|---|---|---|
| 90 | 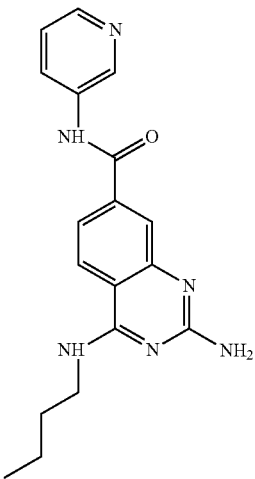 [SMILES: CCCCNc1nc(N)nc2cc(C(=O)Nc3cccnc3)ccc12] | 0.42 | NA | NA |
| 91 | 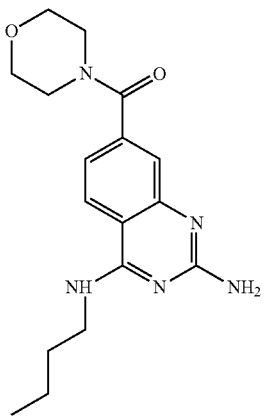 [SMILES: CCCCNc1nc(N)nc2cc(C(=O)N3CCOCC3)ccc12] | 0.13 | 0.53 | NA |
| 92 | 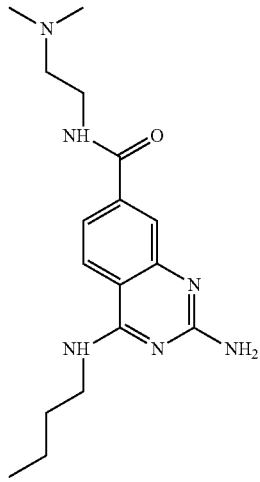 [SMILES: CCCCNc1nc(N)nc2cc(C(=O)NCCN(C)C)ccc12] | 1.53 | 5.87 | NA |

| | | | | |
|---|---|---|---|---|
| 93 | 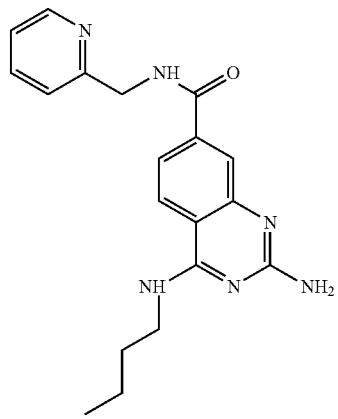 [SMILES: CCCCNc1nc(N)nc2cc(C(=O)NCc3ccccn3)ccc12] | 0.77 | 1.69 | NA |
| 94 | 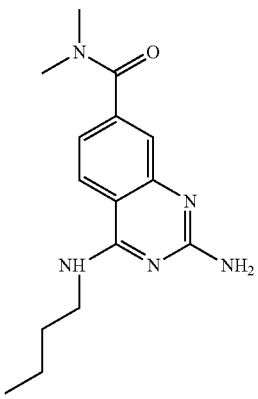 [SMILES: CCCCNc1nc(N)nc2cc(C(=O)N(C)C)ccc12] | 0.07 | 0.48 | NA |
| 95 | 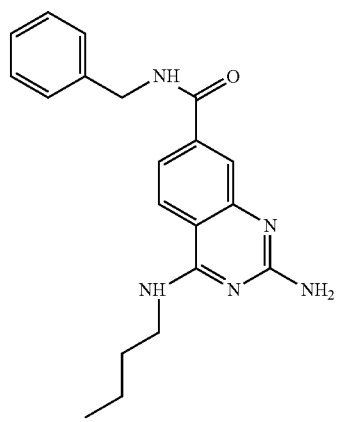 [SMILES: CCCCNc1nc(N)nc2cc(C(=O)NCc3ccccc3)ccc12] | 0.54 | 0.42 | NA |
| 96 | 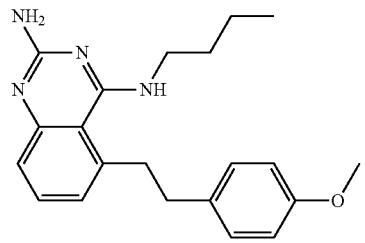 | 2.7 | 16 | NA |

| | | | | |
|---|---|---|---|---|
| 97 | 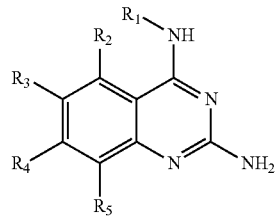 | 0.6 | 0.83 | NA |
| 98 | | 0.21 | 0.31 | NA |

* Assay run at 48 hours

The invention claimed is:

1. A compound of formula (I)

(I)

or a pharmaceutically acceptable salt wherein $R_1$ is one of the following:

$R_2$ is hydrogen, halogen, hydroxyl, amine, $C_{1-7}$alkyl, $C_{1-7}$alkylamino, $C_{1-6}$alkoxy, or $(C_{1-4})$alkoxy-$(C_{1-4})$alkyl, $R_3$ is hydrogen, halogen, hydroxyl, amine, $C_{1-7}$alkyl, $C_{1-7}$alkenyl, $C_{1-7}$alkynyl, $C_{1-7}$alkylamino, $C_{1-6}$alkoxy, or $(C_{1-4})$alkoxy-$(C_{1-4})$alkyl, $R_4$ is hydrogen, halogen, hydroxyl, amine, $C_{1-7}$alkyl, $C_{1-7}$alkylamino, $C_{1-6}$alkoxy, or $(C_{1-4})$alkoxy-$(C_{1-4})$alkyl, and $R_5$ is hydrogen, fluorine, chlorine or methyl with the proviso that $R_2$, $R_3$, $R_4$, and $R_5$ cannot all be H.

2. A compound of formula (I) according to claim 1 wherein $R_5$ is hydrogen or fluorine.

3. A compound of claim 1 selected from the group consisting of

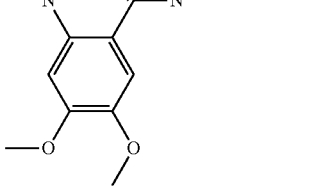

,

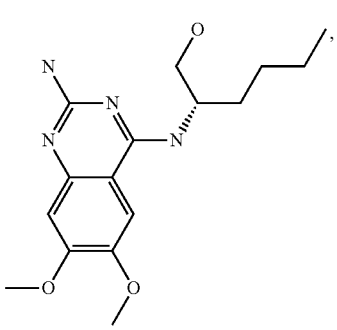

,

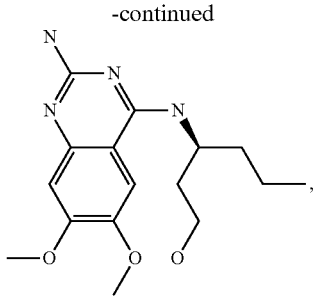
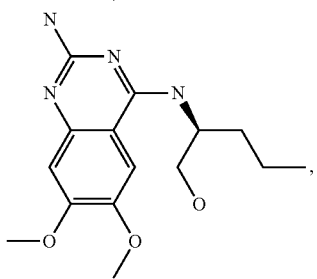
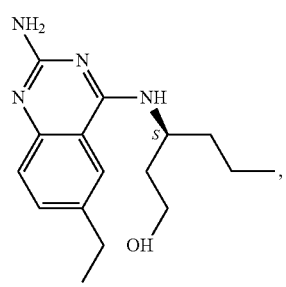
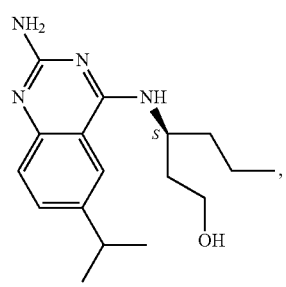
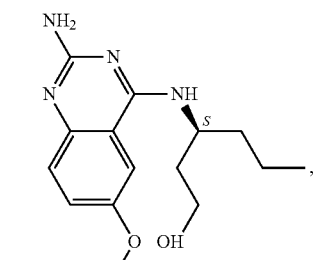
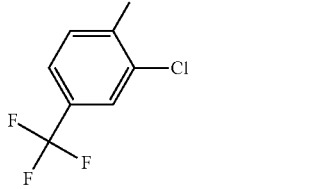
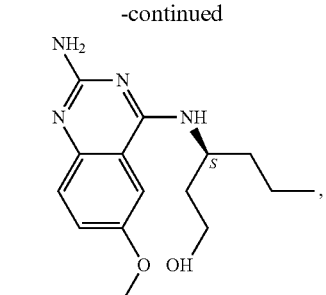
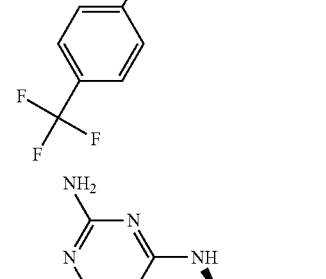
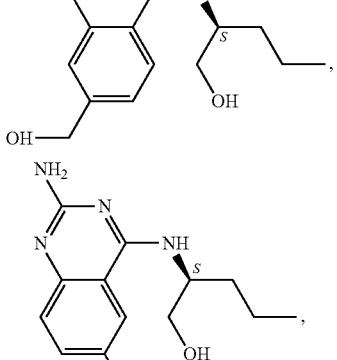
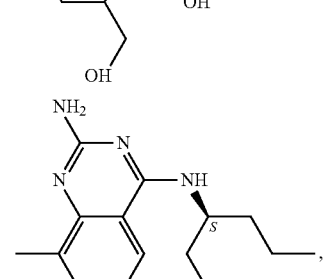
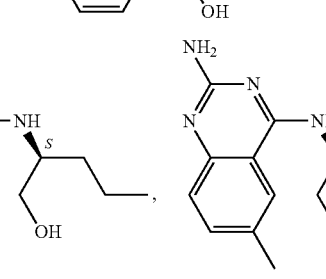
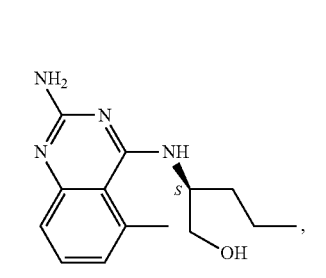

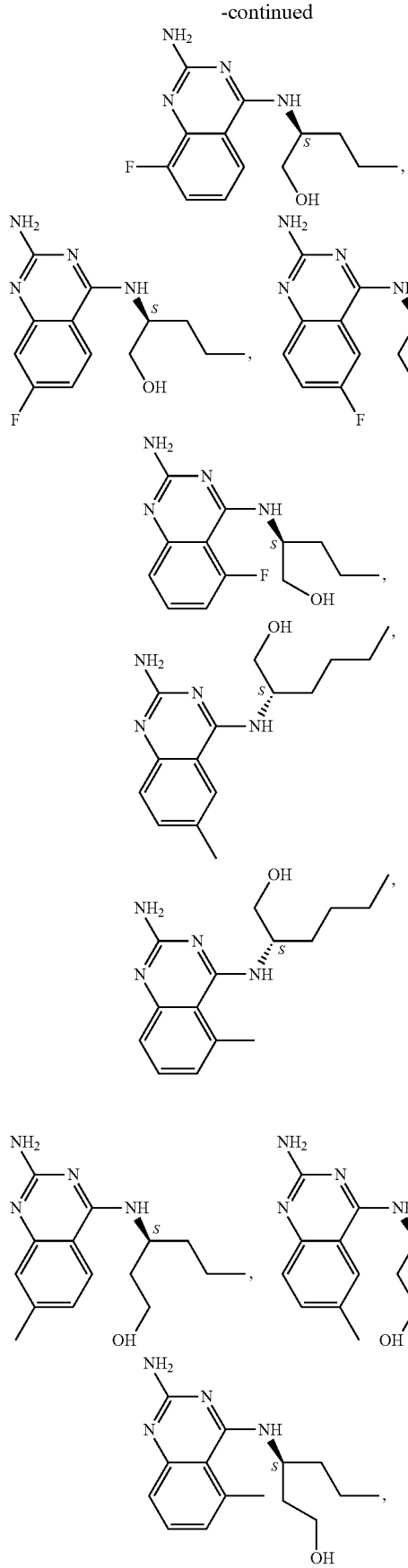
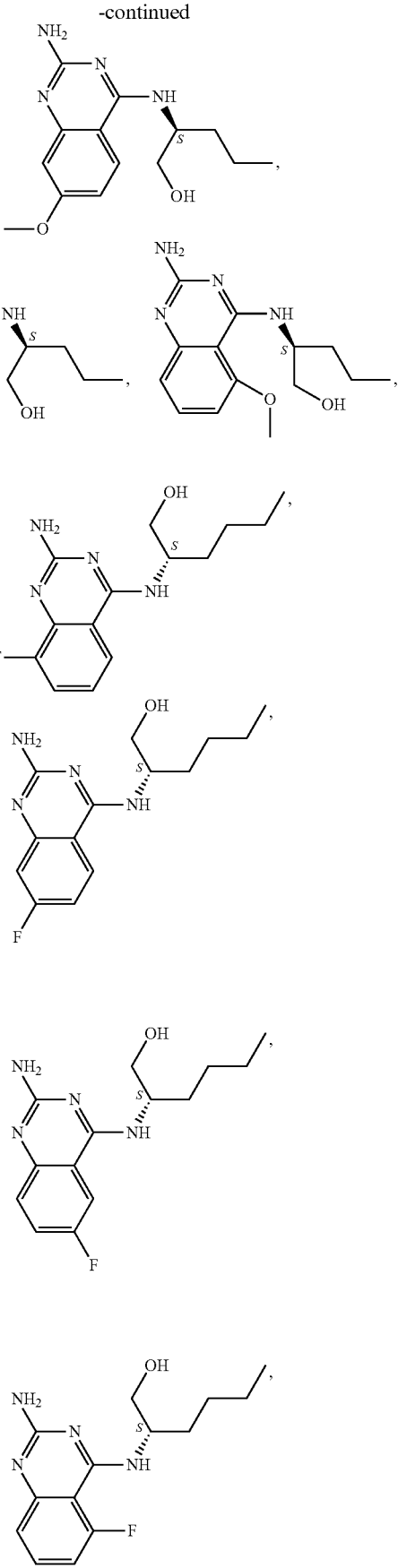

123
-continued
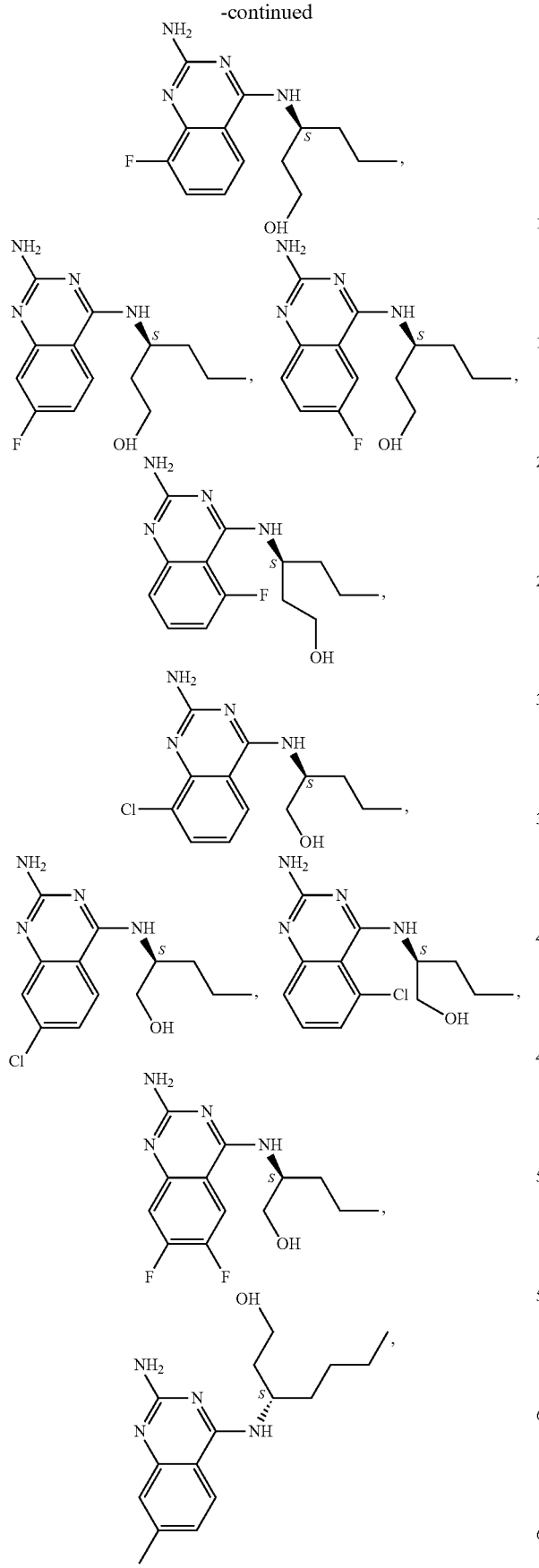
124
-continued
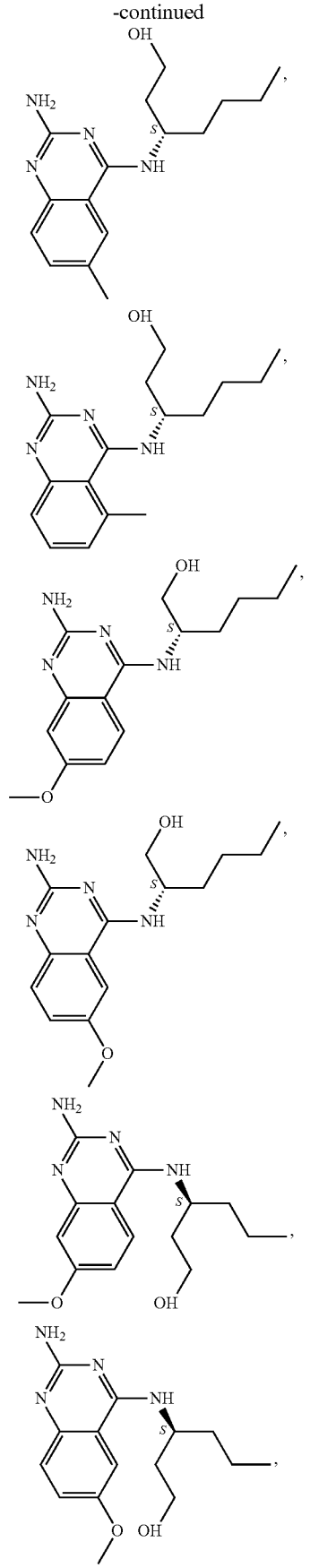

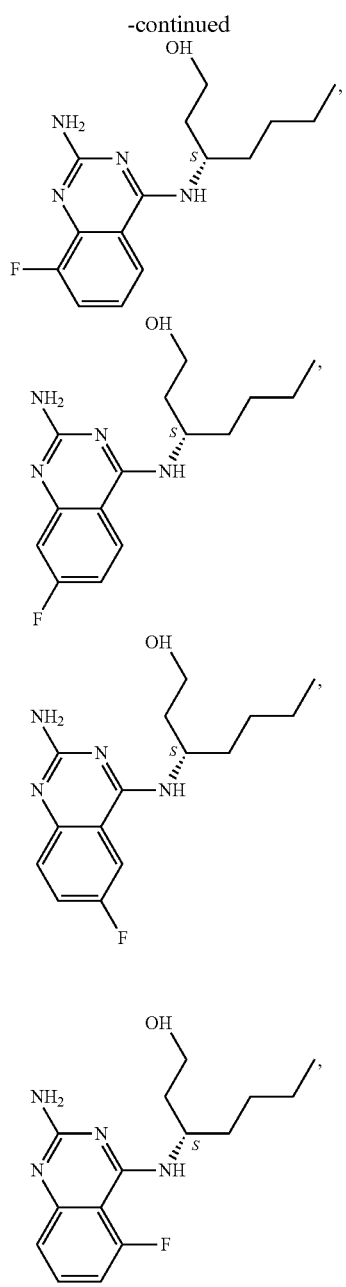
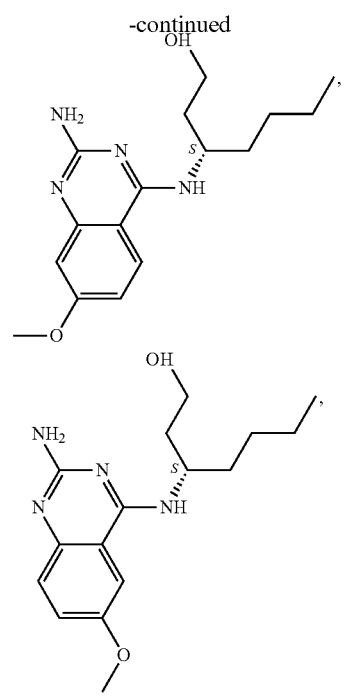
and a pharmaceutically acceptable salt thereof.
4. A compound of claim 1 having the structure:
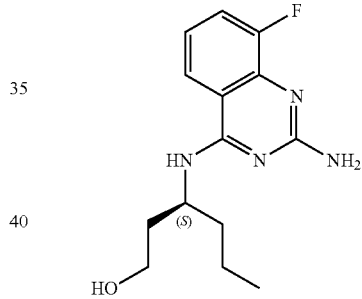
or a pharmaceutically acceptable salt thereof.
5. A pharmaceutical composition comprising a compound of claim 1 or a pharmaceutically acceptable salt thereof and one or more pharmaceutically acceptable excipients, diluents or carriers.
\* \* \* \* \*